United States Patent
McBride

(10) Patent No.: US 11,724,106 B2
(45) Date of Patent: *Aug. 15, 2023

(54) SYSTEMS AND APPARATUS FOR GAIT MODULATION AND METHODS OF USE

(71) Applicant: Bioness Inc., Valencia, CA (US)

(72) Inventor: Keith Sean McBride, Ventura, CA (US)

(73) Assignee: Bioness Inc., Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/391,504

(22) Filed: Aug. 2, 2021

(65) Prior Publication Data

US 2022/0054831 A1    Feb. 24, 2022

Related U.S. Application Data

(63) Continuation of application No. 16/031,721, filed on Jul. 10, 2018, now Pat. No. 11,077,300, which is a
(Continued)

(51) Int. Cl.
*A61N 1/36* (2006.01)
*A61B 5/00* (2006.01)
(Continued)

(52) U.S. Cl.
CPC ........ *A61N 1/36003* (2013.01); *A61B 5/1038* (2013.01); *A61B 5/112* (2013.01);
(Continued)

(58) Field of Classification Search
CPC .............. A61N 1/36003; A61N 1/0452; A61N 1/0484; A61N 1/36014; A61B 5/1038;
(Continued)

(56) References Cited

U.S. PATENT DOCUMENTS 3,204,637 A    9/1965  Frank et al.
3,344,792 A   10/1967  Offner et al.
(Continued)

FOREIGN PATENT DOCUMENTS

CA    2863933 A1   6/2006
DE   19830359 A1   1/2000
(Continued)

OTHER PUBLICATIONS

Extended European Search Report for European Application No. 17738843.6, dated Oct. 8, 2017, 7 pages.
(Continued)

*Primary Examiner* — Catherine M Voorhees
(74) *Attorney, Agent, or Firm* — Cooley LLP

(57) ABSTRACT

The embodiments and methods described herein relate to an improved functional electrical stimulation (FES) orthosis. An apparatus can include a frame assembly, an electrode assembly, and an electric stimulator. The frame assembly is removably coupleable to a portion of a limb. The electrode assembly is configured to be in electrical communication with a portion of a neuromuscular system of the limb, and includes first and second sets of electrodes. The electric stimulator is in electrical communication with the electrode assembly. The electric stimulator is configured to send a first signal substantially during a first time period and via a first channel to the first set of electrodes for stimulation of a neuromuscular system of the limb, and is configured to send a second signal, during at least one of the first time period or a subsequent second time period, via a second channel to the second set of electrodes for stimulation of the neuromuscular system of the limb.

16 Claims, 45 Drawing Sheets

Related U.S. Application Data continuation of application No. PCT/US2017/012977, filed on Jan. 11, 2017.

(60) Provisional application No. 62/277,259, filed on Jan. 11, 2016.

(51) Int. Cl.
  *A61B 5/11* (2006.01)
  *A61N 1/04* (2006.01)
  *A61B 5/103* (2006.01)
  *A61F 5/01* (2006.01)

(52) U.S. Cl.
  CPC .......... *A61B 5/6811* (2013.01); *A61B 5/6828* (2013.01); *A61N 1/0452* (2013.01); *A61N 1/0484* (2013.01); *A61N 1/36014* (2013.01); *A61B 5/0002* (2013.01); *A61B 5/4836* (2013.01); *A61B 5/6807* (2013.01); *A61F 5/01* (2013.01)

(58) Field of Classification Search
  CPC ..... A61B 5/112; A61B 5/6811; A61B 5/6828; A61B 5/0002; A61B 5/4836; A61B 5/6807; A61F 5/01
  See application file for complete search history.

(56) References Cited

U.S. PATENT DOCUMENTS

| | | |
|---|---|---|
| 3,426,748 A | 2/1969 | Bowers |
| 3,881,496 A | 5/1975 | Vredenbregt et al. |
| 3,941,137 A | 3/1976 | Vredenbregt et al. |
| 4,117,846 A | 10/1978 | Williams |
| 4,381,012 A | 4/1983 | Russek |
| 4,432,368 A | 2/1984 | Russek |
| 4,528,984 A | 7/1985 | Morawetz et al. |
| 4,558,704 A | 12/1985 | Petrofsky |
| 4,569,352 A | 2/1986 | Petrofsky et al. |
| 4,580,569 A | 4/1986 | Petrofsky |
| 4,586,495 A | 5/1986 | Petrofsky |
| 4,647,918 A | 3/1987 | Goforth |
| 4,697,808 A | 10/1987 | Larson et al. |
| 4,745,930 A | 5/1988 | Confer |
| 4,777,954 A | 10/1988 | Keusch et al. |
| 4,832,033 A | 5/1989 | Maher et al. |
| 4,976,264 A | 12/1990 | Petrofsky |
| 4,982,732 A | 1/1991 | Morris |
| 4,996,987 A | 3/1991 | Petrofsky |
| 5,016,635 A | 5/1991 | Graupe |
| 5,081,989 A | 1/1992 | Graupe et al. |
| 5,112,296 A | 5/1992 | Beard et al. |
| 5,116,296 A | 5/1992 | Watkins et al. |
| 5,121,747 A | 6/1992 | Andrews |
| 5,167,229 A | 12/1992 | Peckham et al. |
| 5,253,654 A | 10/1993 | Thomas et al. |
| 5,263,481 A | 11/1993 | Axelgaard |
| 5,277,697 A | 1/1994 | France et al. |
| 5,285,781 A | 2/1994 | Brodard |
| 5,300,096 A | 4/1994 | Hall et al. |
| 5,318,597 A | 6/1994 | Hauck et al. |
| 5,323,650 A | 6/1994 | Fullen et al. |
| 5,330,516 A | 7/1994 | Nathan |
| 5,350,414 A | 9/1994 | Kolen |
| 5,357,696 A | 10/1994 | Gray et al. |
| 5,408,873 A | 4/1995 | Schmidt et al. |
| 5,433,737 A | 7/1995 | Aimone |
| 5,437,619 A | 8/1995 | Malewicz et al. |
| 5,476,441 A | 12/1995 | Durfee et al. |
| 5,487,759 A | 1/1996 | Bastyr et al. |
| 5,540,735 A | 7/1996 | Wingrove |
| 5,562,707 A | 10/1996 | Prochazka et al. |
| 5,566,479 A | 10/1996 | Gray et al. |
| 5,628,722 A | 5/1997 | Solomonow et al. |
| 5,643,332 A | 7/1997 | Stein |
| 5,664,346 A | 9/1997 | Barker |
| 5,724,996 A | 3/1998 | Piunti |
| 5,748,845 A | 5/1998 | Labun et al. |
| 5,775,332 A | 7/1998 | Goldman |
| 5,814,093 A | 9/1998 | Stein |
| 5,843,142 A | 12/1998 | Sultan |
| 5,851,191 A | 12/1998 | Gozani |
| 5,861,017 A | 1/1999 | Smith et al. |
| 5,916,159 A | 6/1999 | Kelly et al. |
| 5,951,598 A | 9/1999 | Bishay et al. |
| 5,980,472 A | 11/1999 | Seyl |
| 5,983,140 A | 11/1999 | Smith et al. |
| 6,002,965 A | 12/1999 | Katz et al. |
| 6,019,877 A | 2/2000 | Dupelle et al. |
| 6,064,912 A | 5/2000 | Kenney |
| 6,126,355 A | 10/2000 | Clover, Jr. |
| 6,129,695 A | 10/2000 | Peters et al. |
| 6,174,294 B1 | 1/2001 | Crabb et al. |
| 6,195,921 B1 | 3/2001 | Truong |
| 6,233,476 B1 | 5/2001 | Strommer et al. |
| 6,236,890 B1 | 5/2001 | Oldham |
| 6,240,323 B1 | 5/2001 | Calenzo et al. |
| 6,246,863 B1 | 6/2001 | Kampel |
| 6,261,247 B1 | 7/2001 | Ishikawa et al. |
| 6,282,448 B1 | 8/2001 | Katz et al. |
| 6,308,102 B1 | 10/2001 | Sieracki et al. |
| 6,349,126 B2 | 2/2002 | Ogawa et al. |
| 6,379,313 B1 | 4/2002 | Gozani |
| 6,438,428 B1 | 8/2002 | Axelgaard et al. |
| 6,445,955 B1 | 9/2002 | Michelson et al. |
| 6,456,884 B1 | 9/2002 | Kenney |
| 6,456,885 B1 | 9/2002 | Shiba et al. |
| 6,496,739 B2 | 12/2002 | Arbel |
| 6,507,757 B1 | 1/2003 | Swain et al. |
| 6,516,500 B2 | 2/2003 | Ogino et al. |
| 6,564,103 B2 | 5/2003 | Fischer et al. |
| 6,567,706 B2 | 5/2003 | Bar-Or et al. |
| 6,571,115 B2 | 5/2003 | Axelgaard et al. |
| 6,587,728 B2 | 7/2003 | Fang et al. |
| 6,607,500 B2 | 8/2003 | Da Silva et al. |
| 6,618,624 B2 | 9/2003 | Elias |
| 6,651,352 B2 | 11/2003 | McGorry et al. |
| 6,700,499 B2 | 3/2004 | Kubo et al. |
| 6,701,189 B2 | 3/2004 | Fang et al. |
| D494,273 S | 8/2004 | Haugland et al. |
| 6,829,510 B2 | 12/2004 | Nathan et al. |
| 6,836,744 B1 | 12/2004 | Asphahani et al. |
| 6,978,684 B2 | 12/2005 | Nurse |
| 6,988,005 B2 | 1/2006 | McGraw et al. |
| 7,146,220 B2 | 12/2006 | Dar et al. |
| 7,162,305 B2 | 1/2007 | Tong et al. |
| 7,200,517 B2 | 4/2007 | Darley et al. |
| 7,257,448 B2 | 8/2007 | Crowe et al. |
| 7,337,007 B2 | 2/2008 | Nathan et al. |
| 7,359,751 B1 | 4/2008 | Erickson et al. |
| 7,403,821 B2 | 7/2008 | Haugland et al. |
| 7,410,471 B1 | 8/2008 | Campbell et al. |
| 7,416,537 B1 | 8/2008 | Stark et al. |
| 7,537,573 B2 | 5/2009 | Horst |
| 7,632,239 B2 | 12/2009 | Dar et al. |
| 7,713,217 B2 | 5/2010 | Ikeuchi et al. |
| 7,756,585 B2 | 7/2010 | Embrey et al. |
| 7,785,279 B2 | 8/2010 | Sankai |
| 7,899,556 B2 * | 3/2011 | Nathan ............... A61N 1/36003 607/144 |
| 8,070,703 B2 | 12/2011 | Skahan et al. |
| 8,209,022 B2 | 6/2012 | Dar et al. |
| 8,209,036 B2 | 6/2012 | Nathan et al. |
| 8,382,688 B2 | 2/2013 | Dar et al. |
| 8,694,110 B2 | 4/2014 | Nathan et al. |
| 8,788,049 B2 | 7/2014 | Lasko et al. |
| 8,868,217 B2 * | 10/2014 | Dar ..................... A61N 1/0452 600/386 |
| 8,972,017 B2 | 3/2015 | Dar et al. |
| 9,095,417 B2 | 8/2015 | Dar et al. |
| 9,415,205 B2 | 8/2016 | Lasko et al. |
| 9,867,985 B2 | 1/2018 | Glukhovsky et al. |
| 10,016,598 B2 | 7/2018 | Lasko et al. |
| 10,076,656 B2 | 9/2018 | Dar et al. |

(56) References Cited

U.S. PATENT DOCUMENTS

| | | |
|---|---|---|
| 10,080,885 B2 | 9/2018 | Nathan et al. |
| 10,086,196 B2 | 10/2018 | Glukhovsky et al. |
| 11,058,867 B2 | 7/2021 | Nathan et al. |
| 11,077,300 B2* | 8/2021 | McBride ............... A61B 5/112 |
| 11,247,048 B2 | 2/2022 | Lasko et al. |
| 2001/0039444 A1 | 11/2001 | Bar-Or et al. |
| 2002/0016618 A1 | 2/2002 | Da Silva et al. |
| 2002/0077688 A1 | 6/2002 | Kirkland |
| 2003/0014087 A1 | 1/2003 | Fang et al. |
| 2003/0050673 A1 | 3/2003 | Yamakazi et al. |
| 2003/0065368 A1 | 4/2003 | Van Der Hoeven |
| 2003/0083596 A1 | 5/2003 | Kramer et al. |
| 2003/0093133 A1* | 5/2003 | Crowe ............... A61N 1/36021 607/72 |
| 2003/0114892 A1 | 6/2003 | Nathan et al. |
| 2003/0114893 A1 | 6/2003 | Nathan et al. |
| 2003/0114894 A1 | 6/2003 | Dar et al. |
| 2003/0144710 A1 | 7/2003 | Haugland et al. |
| 2004/0011366 A1 | 1/2004 | Schulman et al. |
| 2004/0015203 A1 | 1/2004 | McGraw et al. |
| 2004/0015204 A1 | 1/2004 | Whitehurst et al. |
| 2004/0015205 A1 | 1/2004 | Whitehurst et al. |
| 2004/0044381 A1 | 3/2004 | Duncan et al. |
| 2004/0122483 A1 | 6/2004 | Nathan et al. |
| 2004/0133081 A1 | 7/2004 | Teller et al. |
| 2004/0147975 A1 | 7/2004 | Popovic et al. |
| 2004/0172097 A1 | 9/2004 | Brodard et al. |
| 2004/0173220 A1 | 9/2004 | Harry et al. |
| 2004/0236384 A1 | 11/2004 | Dar et al. |
| 2004/0243197 A1 | 12/2004 | Demian |
| 2004/0249316 A1 | 12/2004 | Ashihara et al. |
| 2004/0254624 A1 | 12/2004 | Johnson |
| 2005/0010265 A1 | 1/2005 | Baru Fassio et al. |
| 2005/0043660 A1 | 2/2005 | Stark et al. |
| 2005/0049652 A1 | 3/2005 | Tong |
| 2005/0085704 A1 | 4/2005 | Schulz et al. |
| 2005/0085706 A1 | 4/2005 | Perrault et al. |
| 2005/0085743 A1* | 4/2005 | Hacker ............... A61B 5/389 600/554 |
| 2005/0131317 A1 | 6/2005 | Oddsson et al. |
| 2005/0192645 A1 | 9/2005 | Stein et al. |
| 2005/0261609 A1 | 11/2005 | Collings et al. |
| 2006/0015470 A1 | 1/2006 | Lauer et al. |
| 2006/0020421 A1 | 1/2006 | Darley et al. |
| 2006/0111756 A1 | 5/2006 | Chang |
| 2006/0211956 A1 | 9/2006 | Sankai |
| 2006/0276704 A1 | 12/2006 | McGinnis et al. |
| 2006/0282017 A1 | 12/2006 | Avni et al. |
| 2006/0282018 A1 | 12/2006 | Balzano |
| 2007/0021689 A1 | 1/2007 | Stergiou et al. |
| 2007/0106343 A1 | 5/2007 | Monogue et al. |
| 2007/0123756 A1 | 5/2007 | Kitajima et al. |
| 2007/0130893 A1 | 6/2007 | Davies |
| 2007/0179560 A1 | 8/2007 | Tong et al. |
| 2007/0197946 A1 | 8/2007 | Gilmour |
| 2007/0203533 A1 | 8/2007 | Goren et al. |
| 2008/0033505 A1 | 2/2008 | Davis et al. |
| 2008/0045872 A1 | 2/2008 | Bauerfeind et al. |
| 2008/0046036 A1 | 2/2008 | King et al. |
| 2008/0140154 A1 | 6/2008 | Loeb et al. |
| 2008/0154113 A1 | 6/2008 | Zilberman |
| 2008/0154335 A1 | 6/2008 | Thrope et al. |
| 2008/0177355 A1 | 7/2008 | Miesel et al. |
| 2008/0294080 A1 | 11/2008 | Adarraga |
| 2008/0319349 A1 | 12/2008 | Zilberman |
| 2009/0012436 A1 | 1/2009 | Lanfermann et al. |
| 2009/0043357 A1 | 2/2009 | Tong et al. |
| 2009/0099627 A1* | 4/2009 | Molnar ............... A61B 5/4082 604/66 |
| 2009/0149917 A1 | 6/2009 | Whitehurst et al. |
| 2011/0137375 A1 | 6/2011 | McBride |
| 2012/0059432 A1 | 3/2012 | Emborg et al. |
| 2012/0203156 A1 | 8/2012 | Dar et al. |
| 2013/0131555 A1 | 5/2013 | Hook et al. |
| 2014/0135858 A1* | 5/2014 | Ahmed ............... A61N 1/36171 607/3 |
| 2014/0180361 A1 | 6/2014 | Burdick et al. |
| 2015/0148866 A1* | 5/2015 | Bulsen ............... A61N 1/36003 607/48 |
| 2015/0265834 A1* | 9/2015 | Glukhovsky ...... A61N 1/36003 607/49 |
| 2015/0321000 A1 | 11/2015 | Rosenbluth et al. |
| 2016/0129248 A1* | 5/2016 | Creasey ............... A61N 1/0452 607/40 |
| 2019/0009086 A1 | 1/2019 | Lasko et al. |
| 2019/0151649 A1 | 5/2019 | Dar et al. |
| 2019/0167975 A1 | 6/2019 | Nathan et al. |
| 2019/0167986 A1 | 6/2019 | Glukhovsky et al. |
| 2020/0155842 A1 | 5/2020 | Lasko et al. |

FOREIGN PATENT DOCUMENTS

| | | | |
|---|---|---|---|
| EP | 1508302 | | 2/2005 |
| GB | 2474239 | A | 4/2011 |
| JP | S60-119949 | | 6/1985 |
| JP | H06-501854 | | 3/1994 |
| JP | 2002-191580 | A | 7/2002 |
| JP | 2002-200104 | | 7/2002 |
| JP | 2004-503266 | T | 2/2004 |
| JP | 2004-215735 | A | 8/2004 |
| JP | 2004-313555 | A | 11/2004 |
| JP | 2005-514143 | T | 5/2005 |
| JP | 2006-192276 | | 7/2006 |
| JP | 2008-264088 | | 11/2008 |
| JP | 2009-530064 | | 8/2009 |
| JP | 2014-519949 | A | 8/2014 |
| WO | WO 2002/074109 | | 9/2002 |
| WO | WO 2003/051453 | | 6/2003 |
| WO | WO 2004/098703 | | 11/2004 |
| WO | WO 2006/113801 | | 10/2006 |
| WO | WO 2007/083275 | | 7/2007 |
| WO | WO 2008/005865 | | 1/2008 |
| WO | WO 2014/030295 | | 2/2014 |
| WO | WO 2015/188889 | A1 | 12/2015 |
| WO | WO-2015188889 | A1 * | 12/2015 ............... A61B 5/11 |

OTHER PUBLICATIONS

Office Action for Japanese Application No. 2018-534781, dated Oct. 30, 2020 and English translation, 11 pages.
Office Action for Japanese Application No. 2018-534781, dated Aug. 4, 2021 and English translation, 7 pages.
International Search Report and Written Opinion for International Application No. PCT/US2017/012977, dated Mar. 17, 2017, 12 pages.
Alon, G. et al., "Persons with C5 or C6 tetraplegia achieve selected functional gains using a neuroprosthesis," Arch. Phys. Med. Rehabil., 84:119-124 (Jan. 2003).
Bajd, et al., "Funcational Electrical Stimulation: standing and walking after spinal cord injury," CRC Press, Boca Raton, Florida, 1989 (Table of Contents).
Bogataj, U. et al., "Preliminary testing of a dual-channel electrical stimulator for correction of gait," Journal of Rehabilitation Research and Development, vol. 24, No. 3, pp. 75-80, Summer 1987. Retrieved from the Internet: Dec. 29, 2016, <URL: http://www.rehab.research.va.gov/jour/87/24/3/pdf/bogataj.pdf>.
Burridge, et al., "Two-channel stimulation for hemiplegic gait. Control Algorithms, selection of muscle groups and the result of preliminary clinical trial," 6th Internet World Congress for Biomedical Sciences, INABIS 2000.
Chen et al., "Applying Fuzzy Logic to Control Cycling Movement Induced by Functional Electrical Stimulation," IEEE Transactions on Rehabilitation Engineering, vol. 5, No. 2, Jun. 1997, pp. 158-169.
"Clinical evaluation of the ljubljana functional electrical peroneal brace," Subcommittee on Evaluation, Committee on Prosthetics Research and Development Division of Medical Sciences—National Research Council, National Academy of Sciences, Washington, D.C., Report E-7 (1973).

(56) References Cited

OTHER PUBLICATIONS

Daly, W. K., "Electrodes installed in roll-on suspension sleeves," From "MEC '02 The Next Generation," Proceedings of the 2002 MyoElectric Controls/Powered Prosthetics Symposium, Fredericton, New Brunswick, Canada: Aug. 21-23, 2002, University of New Brunswick, 3 pages.

Davis, R. et al., "Evaluation of electrical stimulation as a treatment for the reduction of spasticity," Bulletin of Prosthetics Research, Department of Medicine and Surgery Veterans Administration, Washington, D.C., pp. 302-309 (1974).

Doucet, B. M. et al., "Neuromuscular Electrical Stimulation for Skeletal Muscle Function," Yale Journal of Biology and Medicine, 85:201-215 (2012).

Duncan, R. M., "Basic principles of splinting the hand," Journal of the American Physical Therapy Association, 69(12):1104-1116 (1989).

Feng, C. J. et al., "Three-Dimensional Motion Analysis of the Voluntary Elbow Movement in Subjects with Spasticity," IEEE Transactions on Rehabilitation Engineering, 5(3):253-262, 1997.

Hart, R. L. et al., "A comparison between control methods for implanted FES hand-grasp systems," IEEE Transactions on Rehabilitation Engineering, 6(2):208-218 (Jun. 1998).

Hendricks, H. T. et al., "Functional electrical stimulation by means of the 'Ness Handmaster Orthosis' in chronic stroke patients: an exploratory study," Clinical Rehabilitation, 15:217-220 (2001).

Home Medical Supplies and Equipments XFT, "The Latest G3 Foot Drop System, XFT-2001" accessed Mar. 2, 2015, 3 pages, retrieved from http://www.xft-china.com/product/detail_62_The_Latest_Foot_Drop_System.html.

Innovative Neurotronics, "How WalkAide Works," accessed Mar. 2, 2015, 1 page, retrieved from http://www.walkaide.com/patients/Pages/HowWalkAideWorks.aspx.

Innovative Neurotronics, "WalkAide as RehabilitationTool, The New WalkAide System: The Dynamic FES for Neuro Rehabilitation," accessed Mar. 2, 2015, 4 pages, retrieved from http://www.walkaide.com/medicalprofessionals/Pages/WalkAideforRehab.aspx.

Kralj, A. et al., "Functional electrical stimulation of the extremities: part 1," Journal of Medical Engineering and Technology, pp. 12-15 (Jan. 1977).

Kralj, A. et al., "Functional electrical stimulation of the extremities: part 2," Journal of Medical Engineering and Technology, pp. 75-80 (Mar. 1977).

Kralj, A. R. et al., "Functional Electrical Stimulation: Standing and Walking after Spinal Cord Injury," CRC Press, Boca Raton, FL., pp. 1-15 (1989).

Liberson, W. T. et al., "Functional Electrotherapy: Stimulation of the Peroneal Nerve Synchronized with the Swing Phase of the Gait of Hemiplegic Patients," 3rd International Congress of Physical Medicine, Session on Neuromuscular Diseases, Washington DC, Aug. 25, 1960, pp. 101-105.

NDI Medical, "About ODFS Dropped Foot Stimulator," [online] 2005 [retrieved on Jun. 5, 2006]. Retrieved from the Internet: URL: <http://www.odfs.com/About_ODFS/about_odfs.html>.

Ness H200 Product Specifications "H200™ Overviews Product Specifications," [online] 2006 [retrieved on Jun. 5, 2007]. Retrieved from the Internet: URL: <http://www.bionessinc.com/products/h200/htm>.

Neurodan, "ActiGait® An implantable drop foot correction system," Neurodan A/S—Products—ActiGait® [online] [retrieved on Jun. 5, 2007]. Retrieved from the Internet: URL: <http://www.neurodan.com/actigait.asp>.

NMES Guidelines for Treatment "Gait Training," [online] [retrieved on May 30, 2007]. Retrieved from the Internet: URL: <http://www.empi.com/products1nmes/gait.pdf>.

Odstock Medical Ltd, Datasheet for ODFS QF/120/Pace v1.0, accessed Sep. 12, 2019, 1 page, retrieved from https://www.odstockmedical.com/sites/default/files/datasheet_for_odfs_pace_v1.0_qf120_doc_iss6_web.pdf.

Odstock Medical Ltd, Product Data Sheet for ODFS Leg Cuff V1.0, accessed Sep. 12, 2019, 2 pages, retrieved from https://www.odstockmedical.com/sites/default/files/product_data_sheet_-_leg_cuff_v1.0.pdf.

Odstock Medical Ltd, "Walking," accessed Sep. 12, 2019, 2 pages, retrieved from https://www.odstockmedical.com/walking.

Popovic, M. R. et al., "Neuroprostheses for grasping," Neurological Research, 24:443-452 (Jul. 2002).

Popovic, M. R. et al., "Functional electrical therapy: retraining grasping in spinal cord injury," Spinal Cord, 44:143-151 (2006).

Popovic, et al., "Functional Electrical Stimulation for Grasping and Walking: Indications and Limitations," Spinal Cord, (Jun. 2001), 22 pages.

Popovic, et al., "Surface Stimulation Technology for Grasping and Walking Neuroprostheses—Improving Quality of Life in Stroke/Spinal Cord Injury Subjects with Rapid Prototyping and Portable FES Systems," IEEE Engineering in Medicine and Biology, Jan./Feb. 2001.

Prochazka, A. et al., "The bionic glove: An electrical stimulator garment that provides controlled grasp and hand opening in quadriplegia," Arch. Phys. Med. Rehabil., 78:608-614 (Jun. 1997).

Senelick, R. C., "Technological Advances in Stroke Rehabilitation-High Tech Marries High Touch," US Neurology, 6(2):102-104 (2010), Extract (Touch Group PLC, 4 pages).

Shenzhen XFT Electronics Co., Ltd., Foot Drop System, XFT-2001 User Manual, 16 pages. Retrieved from the Internet: Aug. 10, 2016, <URL: http://www.stressnomore.co.uk/downloads/instructions/91846-IFUS_1.pdf>.

Sowerbutt, C., "Restoring Gait in Stroke Patients Using Functional Neuromuscular Stimulation," [online] Sep. 1, 2006 [retrieved on May 30, 2007]. Retrieved from the Internet: URL: <http://appneurology.com/showArticle.jhtml?print=true&articleID=193104432>.

Springer, S. et al., "Dual-channel functional electrical stimulation improvements in speed-based gait classifications," Clinical Interventions in Aging, 8:271-277 (2013).

Springer, S. et al., "The effects of dual-channel functional electrical stimulation on stance phase sagittal kinematics in patients with hemiparesis," Journal of Electromyography and Kinesiology (2012), 7 pages, http://dx.doi.org/10.1016/j.jelekin.2012.10.017.

Stanic, U., "History of functional electrical stimulation," International Functional Electrical Stimulation Society, INS & IFESS Joint Congress, Sep. 16-20, 1998, Lucerne, Switzerland, 37 pages.

Stopar, M. et al., "New stimulators for cutaneous stimulation," Advances in External Control of Human Extremities, Proceedings of the Seventh International Symposium on External Control of Human Extremities, pp. 267-272 (1981).

Stralka, "Gait Training (by Stimulating Dorsiflexors)," NM III™ Neuromuscular Stimulation System Suggested Protocol, NM III Program Set #2 Program F, Rehabilicare® 920080 Rev. C.

Strojnik, P. et al., "Treatment of drop foot using an implantable peroneal underknee stimulator," Scandanavian J. of Rehabil. Med. 19:37-43 (1987).

Strojnik, P. et al., "Implantable stimulators for neuromuscular control," Chapter 78 in The Biomedical Engineering Handbook: Second Edition, Bronzino, J. D. (ed.), Boca Raton: CRC Press LLC (2000), 15 pages.

Uellendahl, J. E. et al., "Custom silicone sockets for myoelectric prostheses," Journal of Prosthetics and Orthotics, 18(2):35-40 (2006).

Uellendahl, J. E. et al., "Custom silicone sockets for myoelectric prostheses," From "MEC '05 Intergrating Prosthetics and Medicine," Proceedings of the 2005 MyoElectric Controls/Powered Prosthetics Symposium, held in Fredericton, New Brunswick, Canada, Aug. 17-19, 2005, 6 pages.

Vodovnik, L. et al., "Functional electrical stimulation for control of locomotor systems," CRC Critical Reviews in Bioengineering, 6(2):63-131 (Sep. 1981).

Ward, A. R. et al., "Russian electrical stimulation: The early experiments," Physical Therapy, 82(10):1019-1030 (Oct. 2002).

Waters, R. L. et al., "Effectiveness of selected surface electrodes for motor stimulation," Advances in External Control of Human Extremities, Proceedings of the Sixth International Symposium on External Control of Human Extremities, pp. 31-38 (1978).

(56) References Cited

OTHER PUBLICATIONS

Waters, R. L. et al., "Experimental correction of footdrop by electrical stimulation of the peroneal nerve," J Bone Joint Surg Am., vol. 38, No. 8 (Dec. 1975), pp. 1047-1054.

Waters, R. et al., "Treatment of the hemiplegic upper extremity using electrical stimulation and biofeedback training," Report to the Veterans Administration, Contract V600P-1064-79, Funding Period Sep. 27, 1979-Sep. 30, 1980, pp. 251-266.

Wood, D.E., "Spatial sensitivity comparisons between an implanted and surface dropped foot neuromuscular stimulator," 9th Annual Conference of the International FES Society, Sep. 2004.

Office Action for Canadian Application No. 3,010,880, dated Sep. 21, 2022, 4 pages.

* cited by examiner

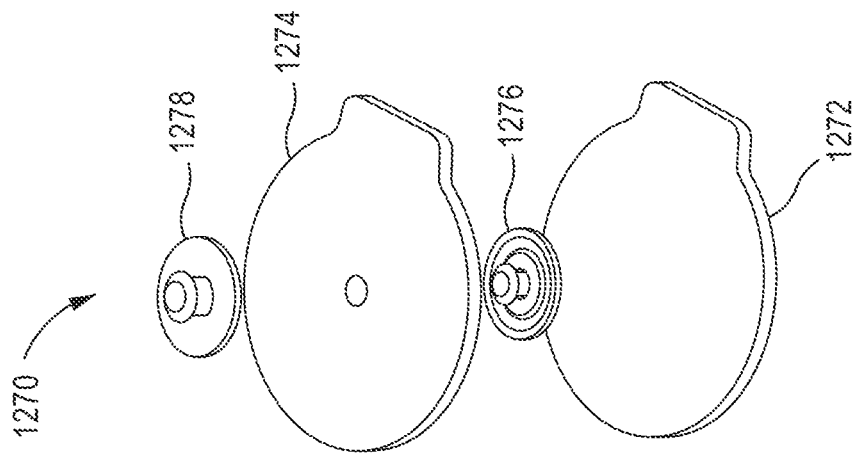
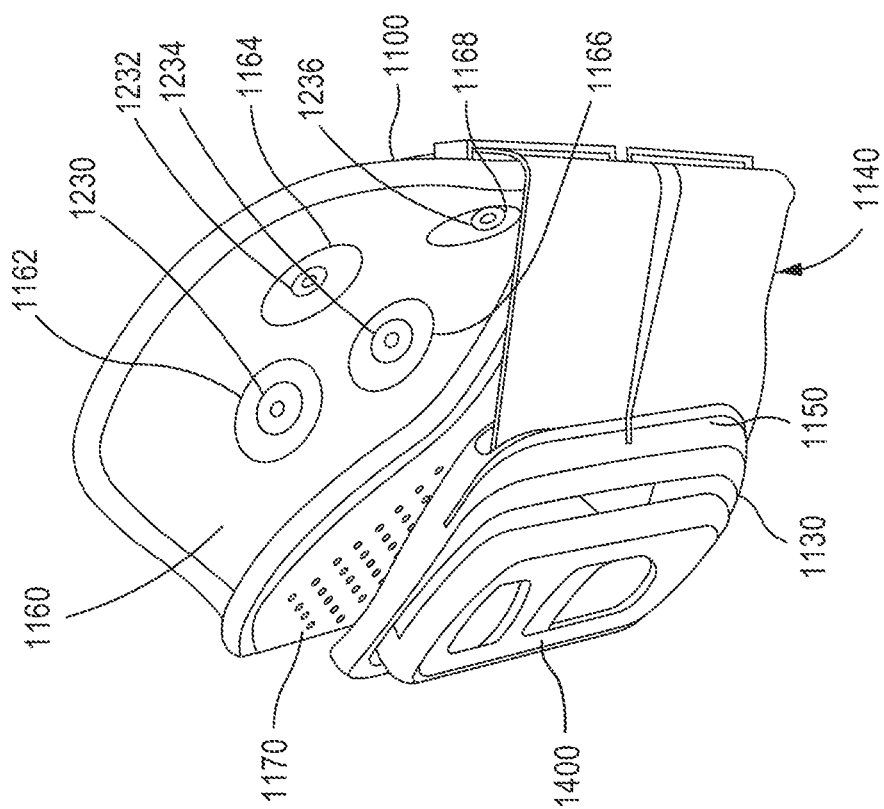

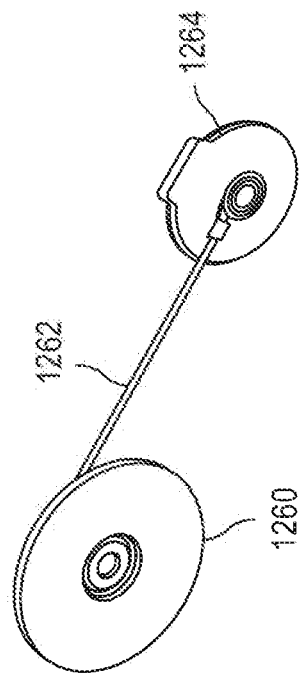
FIG. 20B
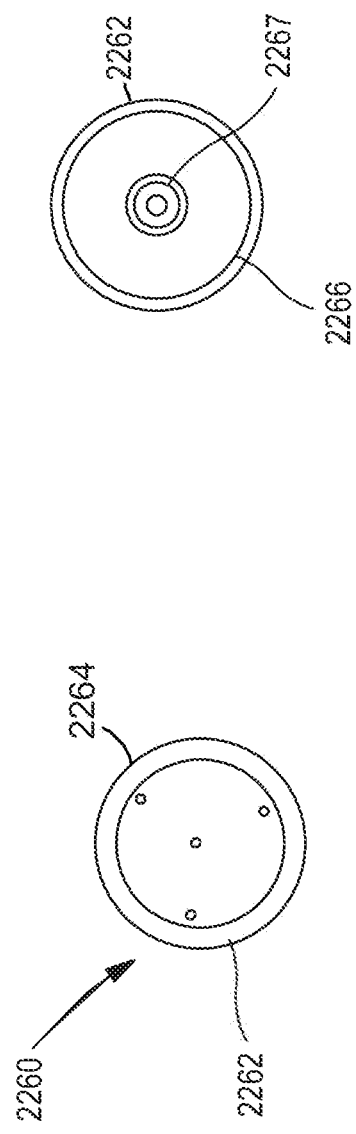
FIG. 20A
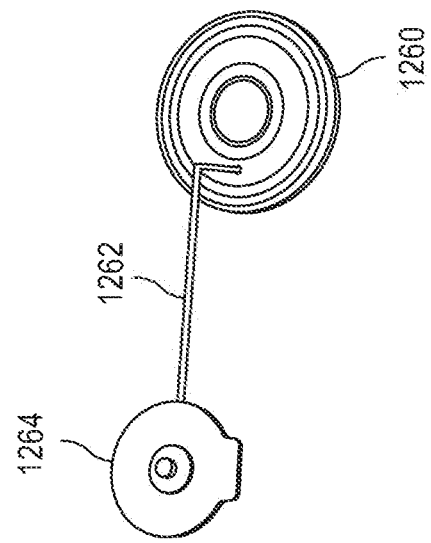
FIG. 20D
FIG. 20C

SYSTEMS AND APPARATUS FOR GAIT MODULATION AND METHODS OF USE

CROSS-REFERENCE TO RELATED APPLICATION(S)

This application is a continuation of U.S. application Ser. No. 16/031,721, entitled "Systems and Apparatus for Gait Modulation and Methods of Use," filed Jul. 10, 2018, now U.S. Pat. No. 11,077,300, which is a continuation of International application No. PCT/US2017/012977, entitled "Systems and Apparatus for Gait Modulation and Methods of Use," filed Jan. 11, 2017, which claims priority to and the benefit of U.S. provisional patent application No. 62/277,259, filed Jan. 11, 2016, entitled "Systems and Apparatus for Gait Modulation and Methods of Use," the disclosure of each of which is incorporated by reference herein in its entirety.

BACKGROUND

The embodiments described herein relate generally to gait modulation systems, and more particularly, to a functional electrical stimulation (FES) system or orthosis for gait modulation and methods of using the same.

It is known that pathologies of the neuromuscular system due to disease or trauma to the central nervous system, such as for example, stroke, spinal cord injury, head injury, traumatic brain injury, cerebral palsy, and multiple sclerosis can impede limb function of the arms or legs (or portions thereof). Gait, the biomechanical description of walking, can suffer static and dynamic parameter variations due to neuromuscular impairments, which can cause non-symmetrical walking, reduced walking speed, and/or reduced walking stability. For example, drop foot describes a gait characteristic attributable to weak or uncoordinated activation of the ankle dorsiflexors due to disease or trauma to the central nervous system. Patients suffering from drop foot tend to drag the foot during the swing phase of walking and usually try to compensate for this dragging by hiking the corresponding hip or swinging the corresponding leg in a circular motion. These patients tend to have reduced stability, are prone to frequent falls, and their walking movements are unaesthetic and energy consuming.

Limb muscles, however, can generally be activated with functional electrical stimulation (FES). In FES, precisely timed bursts of short electrical pulses (e.g., from a neuroprosthetic, an FES orthosis, and/or the like) are applied to motor nerves to generate muscle contraction, which can be applied to enhancing limb function. Although neuroprosthetic systems are known, some such systems suffer from drawbacks that prevent the systems from being widely used by potential patients. For example, in instances in which stroke or brain injury results in problems with arm movement or gait, such problems are often accompanied by hand impairment on the same side of the body as the problematic limb. Thus, donning an FES orthosis is often carried out using solely the contra-lateral, unaffected hand. Moreover, the posture of the plegic limb is often problematic, especially in cases where spasticity results in reduced voluntary movements and/or limited passive range of motion of the limb joints. Consequently, objective biomechanical problems exist in donning some known orthotic devices, as well as in locating the electrodes in exact positions onto the limb, which is essential for activating the desired movement pattern. As such, some known neuroprosthetic devices fail to enable facile, quick, and accurate donning of the device by an impaired patient using a single hand, and particularly, when the least effected hand is shaky or otherwise unstable.

FES devices typically utilize a stimulator unit to create and control the electrical pulses being applied to motor nerves that is physically separate from the FES orthosis. The external stimulator unit, which is connected to the FES orthosis by several electrical wires, is located on the body of the user and/or is otherwise worn or held by the user. These devices can be inconvenient for the user. Specifically, the wiring, which is usually arranged to run along the leg under the clothing to connect the device components, can be difficult to operate, cumbersome and uncomfortable.

In other instances, an FES orthosis can be a self-contained device. For example, some known orthoses can include a stimulator unit coupled to a narrow band that is made of a thermoplastic material, which is molded to the limb anatomy of an individual user by heating and softening the thermoplastic material and subsequently fitting the band to the contour of the underlying limb segment. Thus, the shape and size of the device and the electrode positioning is custom-fitted to the leg of one user and individualized for the user. This procedure is carried out by a medical professional trained, for example, to accurately identify the stimulation points that cause contraction of the muscles, positioning and locking the electrodes thereto.

Activation of the leg muscles by electrical stimulation typically includes transferring high stimulation currents through one or more electrodes to the skin surface of the patient, which activates skin sensory receptors in addition to underlying excitable motor nerve and muscle tissue. As a result, the intensity of sensory activation often depends on the intensity of the current density passing through the skin surface. The level of muscle activation, therefore, is often limited to the patient's individual tolerance to activation of such skin pain sensors. Thus, the stimulation parameters tolerable by the patient may be insufficient to promote optimal movement of the impaired limb in response to the FES. Additionally, although some known systems provide FES to promote movement of an impaired limb (e.g., dorsiflexion of a foot), one or more electrodes of such systems must be moved to various locations on the patient's skin until a desirable movement of the impaired limb is achieved.

Therefore, a need exists for improved systems and apparatus for a neuroprosthetic system that can be easily and accurately donned on the limb by patient. A need also exists for improved systems and apparatus for a neuroprosthetic system that includes a stimulation unit that can provide electrical stimulation in a manner such that a lower intensity stimulation can achieve increased corrective movement of an impaired limb. A need further exists for improved systems and apparatus for a neuroprosthetic system that can provide electrical stimulation to promote movement of the impaired limb without the need for moving one or more electrodes to multiple locations on the patient's skin.

SUMMARY

The embodiments and methods described herein relate to an improved functional electrical stimulation (FES) orthosis for users suffering from an impaired limb. In some embodiments, an apparatus includes a frame assembly, an electrode assembly, and an electric stimulator. The frame assembly is configured to be removably coupled to a portion of a limb such that the portion of the limb is substantially enveloped by the frame. The electrode assembly is configured to be in electrical communication with a portion of a neuromuscular system of the limb. The electrode assembly is removably coupled to the frame assembly. The electrode assembly includes a first set of electrodes and a second set of electrodes. The electric stimulator is removably coupled to the frame assembly and is in electrical communication with the electrode assembly. The electric stimulator is configured to send a first signal substantially during a first time period and via a first channel to the first set of electrodes to provide an electrical stimulation to a neuromuscular system of the limb. The electric stimulator is configured to send a second signal via a second channel to the second set of electrodes to provide electrical stimulation to the neuromuscular system of the limb. The electric stimulator is configured to send the second signal substantially during at least one of the first time period or a second time period subsequent the first time period.

BRIEF DESCRIPTION OF THE DRAWINGS

FIGS. 4-6 are side, front, and perspective views, respectively, of a FES orthosis for gait modulation according to an embodiment.

FIG. 6A is an exploded view of a connector cover according to an embodiment.

FIGS. 20A-20B are top and bottom views, respectively, of an electrode configured for use with the FES orthosis of FIG. 4 according to an embodiment.

FIGS. 20C-20D are perspective views of an electrode base configured for use with the FES orthosis of FIG. 4 according to an embodiment.

DETAILED DESCRIPTION

Figure 1:
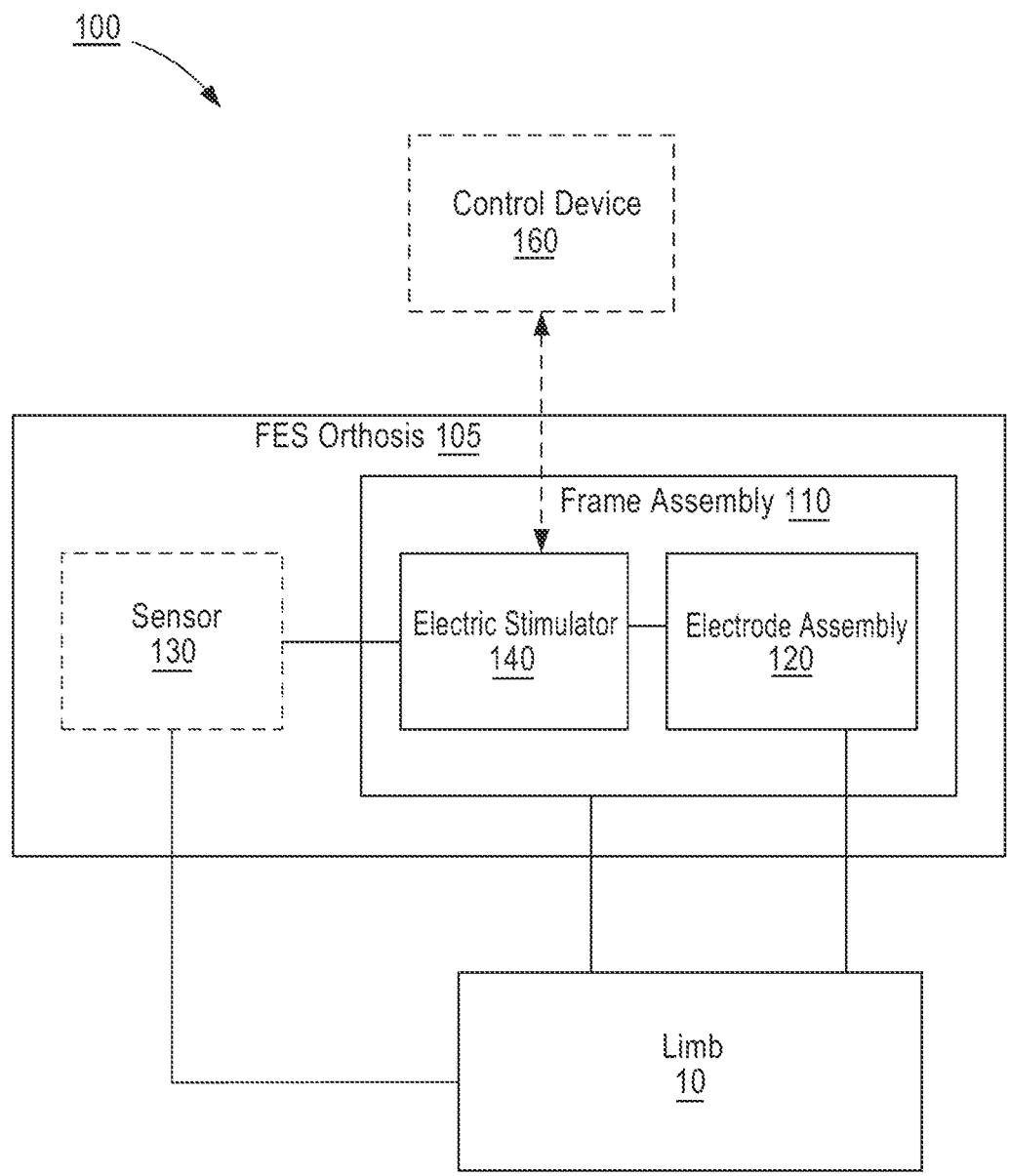
FIG. 1 is a schematic illustration of a system for functional electrical stimulation of a limb according to an embodiment.

The embodiments and methods described herein relate to an improved functional electrical stimulation (FES) orthosis for users suffering from an impaired limb. More particularly, the embodiments and methods described herein relate to an improved FES orthosis for users suffering from gait problems such as drop foot. In some embodiments, an apparatus includes a frame assembly, an electrode assembly, and an electric stimulator. The frame assembly is configured to be removably coupled to a portion of a limb such that the portion of the limb is substantially enveloped by the frame. The electrode assembly is configured to be in electrical communication with a portion of a neuromuscular system of the limb. The electrode assembly is at least partially disposed between the frame assembly and the limb when the limb is substantially enveloped by the frame. The electrode assembly includes a first set of electrodes and a second set of electrodes. The electric stimulator is in electrical communication with the electrode assembly. The electric stimulator is configured to send a first signal substantially during a first time period and via a first channel to the first set of electrodes operable to provide an electrical stimulation to a neuromuscular system of the limb. The electric stimulator is configured to send a second signal via a second channel to the second set of electrodes operable to provide electrical stimulation to the neuromuscular system of the limb. The electric stimulator is configured to send the second signal substantially during at least one of the first time period or a second time period subsequent the first time period.

In some embodiments, an apparatus includes a frame assembly, an electrode assembly and an electric stimulator. The frame assembly is configured to be removably coupled to a portion of a limb such that the portion of the limb is substantially enveloped by the frame. The electrode assembly is configured to be in electrical communication with a portion of a neuromuscular system of the limb. The electrode assembly is removably coupled to an inner surface of the frame assembly and includes a panel of flexible material and a plurality of surface electrodes coupled to the panel. The plurality of surface electrodes includes a set of cathodic electrodes and a set of anodic electrodes. The electric stimulator is removably coupled to the frame assembly. The electric stimulator is configured to apply a first electrical current to the electrode assembly such that the first electrical current is transmitted through bodily tissue between a first cathodic electrode from the set of cathodic electrodes and a first anodic electrode from the set of anodic electrodes. The electric stimulator is configured to apply a second electrical current to the electrode assembly such that the second electrical current is transmitted through bodily tissue between a second cathodic electrode from the set of cathodic electrodes and at least one of the first anodic electrode or a second anodic electrode from the set of anodic electrodes.

In some embodiments, a method includes sending a first signal via a first channel from an electric stimulator to an electrode assembly to cause a first set of electrodes from the electrode assembly to provide an electric stimulation having a first set of parameters substantially during a time period to a neuromuscular system of a limb. The first set of electrodes includes a first cathodic electrode and a first anodic electrode. The method also includes sending a second signal via a second channel from the electric stimulator to the electrode assembly to cause a second set of electrodes from the electrode assembly to provide an electric stimulation having a second set of parameters to the neuromuscular system of a limb. The electric stimulation is provided substantially during at least one of the first time period or a second time period subsequent the first time period. The second set of electrodes includes a second cathodic electrode and at least one of the first anodic electrode or a second anodic electrode.

As used in this specification and the appended claims, the singular forms "a," "an" and "the" include plural referents unless the context clearly dictates otherwise. Thus, for example, the term "a member" is intended to mean a single member or a combination of members, "a material" is intended to mean one or more materials, or a combination thereof.

As used herein, the terms "limb" and "limb segment" refer to at least a portion of a mammalian appendage. For example, the embodiments described herein can be coupled to and/or otherwise placed in contact with a limb segment that can include a portion of the arm (e.g., the shoulder, upper arm, lower arm, or hand), or a portion of the leg (e.g., the hip, upper leg, lower leg, or foot) of a human body.

As used herein, the terms "envelop," "enveloping," and/or the like, with regard to a limb segment and an article or device coupled thereto, refer to an article or device that substantially surrounds and/or covers at least one half the circumference of a limb segment when coupled thereto. For example, if when coupled to a limb, an article or device substantially circumscribes a portion of the limb, the article or device can be said to envelop the portion of the limb.

As used herein, the terms "FES orthosis," "orthosis," "neuroprosthetic," "FES system," "FES device," "device," and/or the like can be used interchangeably and refer generally to a medical apparatus that is selectively placed in contact with a portion of a patient or user. As described herein, such devices can include one or more electrodes that can transmit a flow of electrical current to a portion of a neuromuscular system associated with the portion of the patient or user, thereby providing functional electrical stimulation to, for example, an impaired limb.

As used herein, the terms "reversible," "reversibly," and/or the like when used to described a process and/or procedure generally refer to a non-destructive process or procedure that can be subsequently undone by a similar yet substantially opposed, inverse, and/or opposite non-destructive process or procedure. When used herein with respect to attachment and/or detachment of an element or assembly, a reversible attachment refers to a non-destructive, repeatable attachment and/or detachment of the element or assembly.

As used herein, the term "set" can refer to multiple features or a singular feature with multiple parts. For example, when referring to a set of walls, the set of walls can be considered as one wall with multiple portions, or the set of walls can be considered as multiple, distinct walls. Thus, a monolithically constructed item can include a set of walls. Such a set of walls may include multiple portions that are either continuous or discontinuous from each other. A set of walls can also be fabricated from multiple items that are produced separately and are later joined together (e.g., via a weld, an adhesive, or any suitable method).

As used herein, the terms "about" and/or "approximately" when used in conjunction with numerical values and/or ranges generally refer to those numerical values and/or ranges near to a recited numerical value and/or range. For example, in some instances, "about 40 [units]" can mean within ±25% of 40 (e.g., from 30 to 50). In some instances, the terms "about" and "approximately" can mean within ±10% of the recited value. In other instances, the terms "about" and "approximately" can mean within ±9%, ±8%, ±7%, ±6%, ±5%, ±4%, ±3%, ±2%, ±1%, less than ±1%, or any other value or range of values therein or therebelow. The terms "about" and "approximately" may be used interchangeably. In some instances, such as when assessing a gait phase of a stimulation parameter and/or the like, the terms "about" and "approximately" can generally mean less than plus or minus 10% of the value stated. Furthermore, although a numerical value modified by the term "about" or "approximately" can allow for and/or otherwise encompass a tolerance of the stated numerical value, it is not intended to exclude the exact numerical value stated.

In a similar manner, term "substantially" when used in connection with, for example, a geometric relationship, a numerical value, and/or a range is intended to convey that the geometric relationship (or the structures described thereby), the number, and/or the range so defined is nominally the recited geometric relationship, number, and/or range. For example, two structures described herein as being "substantially parallel" is intended to convey that, although a parallel geometric relationship is desirable, some nonparallelism can occur in a "substantially parallel" arrangement. By way of another example, a structure defining a volume that is "substantially 0.50 milliliters (mL)" is intended to convey that, while the recited volume is desirable, some tolerances can occur when the volume is "substantially" the recited volume (e.g., 0.50 mL). Such tolerances can result from manufacturing tolerances, measurement tolerances, and/or other practical considerations (such as, for example, minute imperfections, age of a structure so defined, a pressure or a force exerted within a system, and/or the like). As described above, a suitable tolerance can be, for example, of ±1%, ±2%, ±3%, ±4%, ±5%, ±6%, ±7%, ±8%, ±9%, ±10%, or more of the stated geometric construction, numerical value, and/or range. Furthermore, although a numerical value modified by the term "substantially" can allow for and/or otherwise encompass a tolerance of the stated numerical value, it is not intended to exclude the exact numerical value stated.

As used herein, the terms "communication channel," "communication mode," and/or "modality" can be used interchangeably and refer generally to one or more modes of communication using, for example, one or more electronic devices. Such modes of communication can be associated with a specific format (e.g., a data unit format) that, in some instances, can be unique to that mode of communication (e.g., a different protocol, a different data unit structure or arrangement, etc.). For example, a cellular telephone (e.g., a smart phone) can send a communication to another electronic device such as an electric stimulator via a modality and/or via a network that is associated with the cellular telephone (e.g., a short message service (SMS) modality, a multimedia message service (MMS) modality, a Bluetooth® modality, a wireless fidelity (WiFi®) modality, etc.). Thus, when referring to a channel and/or modality, the channel and/or modality includes, defines, and/or otherwise is associated with a data unit format suitable for transmission of data via that communication mode.

As used herein, the term "module" refers to any assembly and/or set of operatively-coupled electrical components that can include, for example, a memory, a processor, electrical traces, optical connectors, software (executing in hardware), and/or the like. For example, a module executed in the processor can be any combination of hardware-based modules (e.g., a field-programmable gate array (FPGA), an application specific integrated circuit (ASIC), a digital signal processor (DSP)) and/or software-based modules (e.g., a module of computer code stored in memory and/or executed at the processor) capable of performing one or more specific functions associated with that module.

As used herein, and unless the context clearly indicates otherwise, the words "proximal" and "distal" refer to the direction closer to and away from, respectively, the torso of a user or wearer of a medical device.

FIG. 1 is a schematic illustration of a system 100 used for gait modulation according to an embodiment. For example, in some instances, the system 100 can be used by a human patient who has one or more impaired limbs as a result of injury and/or disease (e.g., stroke, spinal cord injury, head injury, traumatic brain injury, cerebral palsy, multiple sclerosis, etc.). More specifically, the system 100 includes a functional electrical stimulation (FES) orthosis 105 (also referred to herein as "orthosis" and/or "device") that is placed in physical and electrical contact with a limb 10 of the patient such as, for example, a lower limb segment of an impaired leg. As such, the patient and/or a health care professional (e.g., doctor, nurse, technician, physician, physical therapist, etc.) can engage the system 100 in such a manner as to cause the orthosis 105 to selectively provide electrical stimulation to a portion of a neuromuscular system of the limb 10, which can, in turn, facilitate gait of the patient who might otherwise experience, for example, drop foot or the like, as described in further detail herein.

More particularly, the orthosis 105 can be configured for multiple channel stimulation of the portion of the neuromuscular system of the limb 10, as described in more detail herein. In this manner, the orthosis 105 can direct or steer a stimulation current within the portion of the neuromuscular system of the limb 10 to achieve more targeted stimulation therein to achieve improvements in the patient's gait over that which is possible using known single channel FES systems with known electrode configurations. In some embodiments, the orthosis 105 is selectively operable to provide single channel stimulation, dual channel stimulation, and optionally three channel stimulation, to the portion of the neuromuscular system of the limb 10, as described in more detail herein. In some embodiments, the orthosis 105 is selectively operable to provide up to six channel stimulation. In some embodiments, the orthosis 105 is selectively operable to provide monopolar and/or bipolar stimulation to the portion of the neuromuscular system of the limb.

The orthosis 105 includes a frame assembly 110, an electrode assembly 120, and an electric stimulator 140. In some embodiments, at least a portion of the orthosis 105 can be substantially similar in form and function as those described in U.S. Pat. No. 7,899,556 entitled, "Gait Modulation System and Method," filed Apr. 27, 2006 (referred to henceforth as the "'556 patent"), U.S. Pat. No. 8,209,036 entitled, "Gait Modulation System and Method," filed Nov. 12, 2006 (referred to henceforth as the "'036 patent"), U.S. Pat. No. 8,694,110 entitled, "Orthosis for Gait Modulation," filed Jun. 25, 2012 (referred to henceforth as the "'110 patent"), and U.S. patent application Ser. No. 14/223,340 entitled "Systems and Apparatus for Gait Modulation and Methods of Use," filed Mar. 24, 2014 (referred to henceforth as the "'340 application"), the disclosures of which are incorporated herein by reference in their entireties.

The frame assembly 110 is configured to be removably coupled to a portion of a limb such that the portion of the limb is substantially enveloped by the frame assembly. In some embodiments, a portion of the frame assembly 110 includes one or more locators configured to facilitate proper positioning of the orthosis 105 with respect to the limb of the patient. The locator can be formed by a recess or concavity along an edge of the frame assembly 110 such that the recess or concavity is configured to be aligned with a predetermined location of the patient's anatomy (e.g., a lower end of a patella of the patient's leg, a ridge of the tibial crest, or the like). In some embodiments, an orthosis 105 includes a locator configured to provide a visual indication of the position of the orthosis, such as a line or arrow disposed thereon that should be aligned with a predetermined portion of the patient's anatomy.

The frame assembly 110 can include one or more layers. In some embodiments, at least a portion of the frame assembly 110, such as a first layer, can be formed from a semi-rigid material such as, for example, a relatively thin metal, a thermoplastic, a polymer, and/or the like, which can enable the frame assembly 110 to provide structural support for the orthosis 105. Such a first layer of the frame assembly 110 is also referred to herein as a "frame". At least a portion of the frame assembly 110, such as a second or inner layer, can be formed from a soft and/or flexible material, such as a nylon. At least a portion of the frame assembly 110, such as the second or inner layer, can be formed from a brushed fabric, a hook and/or loop material, or the like, such as those offered commercially by Nam Liong Enterprise Co., Ltd. In some embodiments, the frame assembly 110 includes a third or outer layer, which can be formed, at least in part, from a flexible and/or elastic material such as elastane or spandex (such as Lycra®) or any other suitable material. In some embodiments, the first layer (or frame) is disposed between the second (or inner) layer and the third (or outer) layer of the frame assembly 110. In some embodiments, the frame assembly 110 is devoid of a rigid or semi-rigid layer. In other words, in some embodiments, the frame assembly 110 can include one or more soft and/or flexible layers configured to be removably coupled to (or disposed about) a portion of the limb such that the portion of the limb is substantially enveloped by the frame assembly and such that the one or more soft and/or flexible layers provide the structural support for the orthosis 105. The layers of the frame assembly can be coupled together using any suitable coupling mechanism including, but not limited to an adhesive, welding, stitching or the like.

The frame assembly 110 can have any suitable shape and/or size that can be, for example, associated with a segment of the limb 10 (e.g., a lower segment of a patient's leg, an upper segment of a patient's leg, a lower segment of a patient's arm, an upper segment of a patient's arm, a patient's hand). Moreover, at least a portion of the frame assembly 110 can be transitioned between a first configuration and a second configuration to couple the frame assembly 110 to the limb 10. For example, in some embodiments, the frame assembly 110 can include a coupling portion or the like that can be transitioned between a first (e.g., open) configuration and a second (e.g., closed) configuration to at least temporarily couple the frame assembly 110 to the limb 10. Expanding further, when the orthosis 105 is coupled to the limb 10, the frame assembly 110 can be configured to substantially envelop and/or circumscribe the limb 10. In some embodiments, the coupling portion can include one or more straps, clips, ratchets, and/or the like that can allow for facile placement and coupling of the frame assembly 110 to the limb 10, as described in further detail herein.

The electrode assembly 120 of the orthosis 105 is coupled to an inner surface of the frame assembly 110. As such, when the frame assembly 110 is coupled to the limb 10 (e.g., moved from its first configuration to its second configuration), at least a portion of the electrode assembly 120 is placed in contact with a surface of the limb 10, as described in further detail herein. The electrode assembly 120 can be any suitable arrangement of hardware and/or software. For example, in some embodiments, the electrode assembly 120 can include one or more electrodes that are each electrically coupled to a wire, electrical trace, and/or the like that are operable in electrically coupling the one or more electrodes to the electric stimulator 140. In some embodiments, at least a portion of the electrode assembly 120 can be disposed within a portion of the frame assembly 110. For example, in such embodiments, the electrode assembly can include a set of wires that are substantially enclosed by a portion of the frame assembly 110. In some embodiments, at least a portion of the set of wires is disposed within or otherwise extended through an opening defined by the frame assembly 110. The wires can include end portions that each include a connector or the like that can, for example, be electrically coupled to the electric stimulator 140 at a first end portion and that can, for example, be electrically coupled to the electrodes at a second end portion.

Although the connectors are described with respect to orthosis 105 as being included in the electrode assembly 120, in some embodiments, the electrode assembly 120 is electrically coupled to the electric stimulator 140 by a connector assembly, as described in more detail herein. For example, in such embodiments, the connector assembly can include a set of wires that are substantially enclosed by a portion of the frame assembly 110. The wires can include end portions that each include a connector or the like that can, for example, be electrically coupled to the electric stimulator 140 at a first end portion and that can, for example, be electrically coupled to the electrodes at a second end portion. In some embodiments, a second end portion of each wire is electrically coupled to a connector, electrode base, or the like, configured to couple an electrode of the electrode assembly to the frame assembly 110. In some embodiments, at least a portion of the connector assembly is disposed within or otherwise extended through an opening defined by the frame assembly 110. In some embodiments, the electrode assembly 120 can be substantially similar in many respects in form and/or function as those described in the '556 patent, the '036 patent, the '110 patent, and/or the '340 application.

In some embodiments, the electrode assembly 120 includes at least one electrode configured to provide an electric stimulation to at least a portion of a neuromuscular system of the limb. As described in more detail herein, each electrode can be engaged by the system 100, and the electric stimulator 140 particularly, to promote desired movement of the limb, such as dorsiflexion, plantarflexion, inversion, and/or eversion of the foot. Selective electrode activation and selective flow of electrical current via one or more channels affects the flow of the electrical current through the portion of the neuromuscular system of the limb 10, and thus can be referred to as "steering" or directing the current, or more simply "current steering".

More specifically, as described in more detail herein, the orthosis 105 is configured for multi-channel stimulation of the neuromuscular system of the limb. As such, the electrode assembly 120 can include any suitable number of electrodes to provide such multi-channel stimulation. In some embodiments, the electrode assembly 120 includes at least three electrodes. For example, the electrode assembly 120 can include two cathodic electrodes and one anodic electrode. In such an embodiment, an electrical current can flow via a first channel (e.g., from the electric stimulator 140) such that stimulation is provided to the portion of the neuromuscular system of the limb 10 between a first cathodic electrode and the anodic electrode, and electrical current can flow via a second channel such that stimulation is provided to the portion of the neuromuscular system of the limb 10 between a second cathodic electrode and the anodic electrode, as described in more detail herein. In other embodiments, the electrode assembly 120 can include two anodic electrodes and one cathodic electrode, which can similarly provide electrical stimulation via two channels. In other words, the orthosis 105 can be configured for multi-channel stimulation such that at least one electrode of the electrode assembly 120 is used to deliver stimulation via at least two different channels. In this manner, the electrode assembly 120 can include at least one electrode that is shared between two or more stimulation channels during FES using the orthosis 105.

In some embodiments, the electrode assembly 120 includes four, five, six, or more electrodes. For example, the electrode assembly 120 can include two cathodic electrodes and two anodic electrodes. In such an embodiment, an electrical current can flow via a first channel (e.g., from the electric stimulator 140) such that stimulation is provided to the portion of the neuromuscular system of the limb 10 between a first cathodic electrode and a first anodic electrode, and electrical current can flow via a second channel to the portion of the neuromuscular system of the limb 10 between a second cathodic electrode and a second anodic electrode, as described in more detail herein. In some embodiments, the electrical current can flow via the first channel substantially concurrently with the flow of electrical current via the second channel. In some embodiments, the electrical current can flow via the first channel before or after the flow of electrical current via the second channel. In some embodiments, electrical current can be provided by the first channel and the second channel in an alternating pattern.

In another example, the electrode assembly 120 can include three cathodic electrodes and one anodic electrode. In such an embodiment, an electrical current can flow via a first channel (e.g., from the electric stimulator 140) such that stimulation is provided to the portion of the neuromuscular system of the limb 10 between a first cathodic electrode and the anodic electrode, electrical current can flow via a second channel such that stimulation is provided to the portion of the neuromuscular system of the limb 10 between a second cathodic electrode and the anodic electrode, and electrical current can flow via a third channel such that stimulation is provided to the portion of the neuromuscular system of the limb 10 between a third cathodic electrode and the anodic electrode. In this manner, the anodic electrode is a shared electrode between the three stimulation channels. In some embodiments, the electrode assembly 120 can include three anodic electrodes and one cathodic electrode, which can similarly provide electrical stimulation via three channels In still another example, the electrode assembly 120 can include three cathodic electrodes and two anodic electrodes. In such an embodiment, an electrical current can flow via a first channel (e.g., from the electric stimulator 140) such that stimulation is provided to the portion of the neuromuscular system of the limb 10 between a first cathodic electrode and a first anodic electrode, electrical current can flow via a second channel such that stimulation is provided to the portion of the neuromuscular system of the limb 10 between a second cathodic electrode and the first anodic electrode, and electrical current can flow via a third channel such that stimulation is provided to the portion of the neuromuscular system of the limb 10 between a third cathodic electrode and a second anodic electrode, as described in more detail herein. In yet another example, the electrode assembly 120 can include three cathodic electrodes and three anodic electrodes.

In some embodiments, the electrode assembly 120 includes a set of electrodes configured to provide stimulation to a portion of the neuromuscular system of the limb that results in dorsiflexion of a foot of the patient. In some embodiments, the electrode assembly 120 includes a set of electrodes configured to provide stimulation to a portion of the neuromuscular system of the limb that results in inversion or eversion of the foot such that a sole of the foot is moved towards a neutral position with respect to a midline of the patient's body and away from an everted or inverted position, respectively (referred to herein as a "balanced" or "neutral" position). In some embodiments, the electrode assembly 120 includes a set of electrodes configured to provide stimulation to a portion of the neuromuscular system of the limb that causes plantarflexion of the foot. One or more electrodes from the electrode assembly can be included in one or more of the foregoing sets of electrodes. In other words, in some embodiments, at least one electrode is "common" to or "shared" by at least two of the foregoing sets of electrodes. In other words, one or more electrodes can provide stimulation that results in both dorsiflexion and movement of the foot towards a neutral position. Any one or more of the foregoing sets can be selectively and concurrently operable, for example, to promote a desired degree of dorsiflexion of the foot concurrently with a desired degree of inversion or eversion of the foot towards a neutral position, or a desired degree of plantarflexion of the foot concurrently with a desired degree of inversion or eversion of the foot towards a neutral position.

In some embodiments, the electrode assembly 120 includes a set of electrodes coupled to, disposed on, or otherwise formed on a panel configured to be coupled to an inner surface of the frame assembly 110. The panel can be coupled to the frame assembly 110 using any suitable coupling mechanism, such as one or more mechanical fasteners (e.g., snaps, hook-and-loop, or the like).

The panel can be constructed of a flexible material to facilitate placement of the electrodes on the skin of the patient when the orthosis 105 is donned. In some embodiments, the panel is formed of a non-conductive material. In some embodiments, the panel includes non-conductive regions separating each electrode from the set of electrodes. In some embodiments, the set of electrodes is coupled to or included in a single panel. For example, at least two, three, four, five, or six electrodes can be coupled to or included in the panel.

In other embodiments, the set of electrodes can be distributed among more than one panel. Such an arrangement can be beneficial for use with an orthosis configured to provide FES to promote plantarflexion, in addition to dorsiflexion, of the foot, because the separate panels permit the placement of electrodes on opposing, or otherwise spaced apart, locations of the inner surface of the frame assembly such that the electrode assembly can be positioned on opposing sides of the patient's limb. For example, in some embodiments, the electrode assembly includes a first panel and a second panel, each of which includes multiple electrodes. The first panel can include one, two, three, four, five or more electrodes, and the second panel can include one, two, three, four, five or more electrodes. More specifically, in some embodiments, the first panel can include three electrodes and the second panel can include two electrodes. In other embodiments, the first panel can include four electrodes and the second panel can include two electrodes. In other embodiments, however, a single panel can include two, three, four, five or more electrodes positioned or disposed thereon such that at least one electrode is spaced a distance from at least another electrode that the electrode assembly is positioned on opposing sides of the patient's limb when the orthosis 100 is donned for FES.

A position of one or more electrodes with respect to the panel can be fixed. In other words, one or more of the electrodes can be fixedly coupled to the panel, which facilitates repeatable placement of the electrode with respect to the frame assembly when the electrode assembly 120 is coupled to the frame assembly 110. At least a first electrode can be positioned with respect to the panel such that, when the panel is coupled to the frame assembly 110 and donned on the limb 10, the first electrode is disposed over or proximate to a target nerve (e.g., a tibial nerve or a peroneal nerve) or muscle of the neuromuscular system of the limb 10. For example, at least one cathodic electrode of the electrode assembly can be positioned on the panel such that, in use, the at least one cathodic electrode provides or facilitates steering of electrical stimulation at least to the target nerve or muscle of the neuromuscular system of the limb 10. At least a second electrode can be coupled to the panel in a position such that, when coupled to the frame assembly 110 and donned on the limb 10, the second electrode is disposed over or proximate to a target nerve or muscle of the neuromuscular system of the limb. For example, at least one anodic electrode of the electrode assembly can be positioned on the panel such that, in use, the at least one anodic electrode facilitates steering of electrical stimulation to at least the target nerve or muscle of the neuromuscular system of the limb 10.

The electric stimulator 140 of the orthosis 105 is configured to apply functional electrical stimulation to the neuromuscular system of the patient's limb, and can include any suitable combination of hardware and software. For example, the electric stimulator 140 can be an electronic device or module that can include one or more electrical circuits operable in providing a flow of electrical current to at least a portion of the neuromuscular system of the limb 10. More specifically, in some embodiments, the electric stimulator 140 can be configured to provide the flow of electrical current via multiple channels to one or more portions of the neuromuscular system of the limb 10, as described herein.

The electric stimulator 140 of the orthosis 105 is removably coupled to the frame assembly 110. For example, in some embodiments, the frame assembly 110 can form a cradle and/or the like that can be configured to at least temporarily retain the electric stimulator 140 therein, as described herein. In this manner, the electric stimulator 140 can be mounted to and supported by the frame assembly 110.

The electric stimulator 140 is configured to be placed in electrical communication with the electrode assembly 120, for example, when the electric stimulator 140 is removably coupled to the frame assembly. In some embodiments, the cradle of the frame assembly can include at least one electrical contact configured to electrically couple the electric stimulator 140 to the electrode assembly 120. The electrode assembly 120 can be operably coupled to the electric stimulator 140 via any suitable wiring, connector, interface, and/or structure. For example, in some embodiments, the frame assembly 110 can include a connection assembly including one or more wires, connectors and/or the like configured to place the electric stimulator 140 in electrical communication with, for example, the electrode assembly 120. In some embodiments, at least a portion of such a connection assembly is disposed in the cradle of the frame assembly 110.

In some embodiments, the electric stimulator 140 can receive and/or send signals to a set of external and/or implanted electrical devices via any suitable communication mode. For example, in some embodiments, the electric stimulator 140 can include two, three, four, five, six, or more communication and/or electrical channels that can be operable in sending and/or receiving signals to and/or from, respectively, the electrode assembly 120, a sensor 130 associated with the orthosis 105, and/or any other suitable electronic device operably coupled thereto. In some embodiments, at least a portion of the communication and/or electrical channels can be associated with sending and/or receiving a signal via a wireless communication modality (e.g., a modality, format, and/or the like associated with WiFi®, Bluetooth®, near field communication (NFC), cellular communication such as, short message service (SMS) or multimedia message service (MMS), and/or the like), as described in further detail herein.

As discussed above, the electric stimulator 140 can be configured to provide multi-channel electrical stimulation. The electric stimulator 140 can include at least two channels for providing a flow of electrical current to at least a portion of the neuromuscular system of the limb 10 via the electrode assembly, as described herein. In some embodiments, the electric stimulator 140 includes three channels for providing the flow of electrical current to the neuromuscular system of the limb 10. In this manner, the electric stimulator 140 can selectively and independently control one or more parameters associated with the flow of electrical current via each channel.

Such parameters can include, but are not limited to, the electrical current's amplitude, voltage, pulse rate, waveform, phase duration, or the like. For example, the electric stimulator 140 can provide a flow of electrical current having a first intensity via a first channel, and a flow of electrical current having a second intensity via a second channel. The intensity of the electrical current associated with each channel can be controlled or otherwise affected by the value of one or more of the foregoing parameters, or any combination thereof. The second intensity can be less than, substantially equal to, or greater than the first intensity. Said another way, the value of the first intensity is independent of the value of the second intensity. In some embodiments, the first intensity includes a first amplitude and the second intensity includes a second amplitude. Each of the first amplitude and the second amplitude can be within the range of about 10 milliamperes (mA) to about 50 mA. For example, in some embodiments, the first amplitude is within the range of about 10 milliamperes (mA) to about 50 mA, and the second amplitude is within the range of about 10 mA to about 30 mA. More specifically, in some embodiments, the first amplitude can be about 30 mA and the second amplitude can be about 25 mA. It should be noted that by using dual-channel stimulation, similar or improved foot movement can be promoted utilizing lower intensities that resulting from stimulation at a higher intensity using a known FES system. In some embodiments, the electrical current provided via at least one of the first channel or the second channel has a pulse rate within the range of 10 hertz ("Hz") to 60 Hz. For example, in one embodiment, the pulse rate of the current provided by both the first channel and the second channel is 30 Hz. In another example, in one embodiment, the pulse rate of the current provided by both the first channel and the second channel is 40 Hz. In some embodiments, the electrical current provided via at least one of the first channel or the second channel has a symmetric waveform, however, in other embodiments the current can produce a different waveform, such as an asymmetric waveform or a sine waveform (such as that produced using what is conventionally known as "Russian stimulation," or "Burst Mode Alternating Current" stimulation). In some embodiments, the electrical current provided via at least one of the first channel or the second channel has a phase duration within the range of 50 microseconds (μs) to 300 μs. For example, in one embodiment, the phase duration of the current provided by both the first channel and the second channel is 200 μs.

In some embodiments, the electric stimulator 140 can provide and control one or more of the parameters of the flow of electrical current via the first channel, the second channel, and, optionally, a third channel, substantially concurrently. In this manner, the electric stimulator 140 can cause electrical current to flow through two or more of the channels substantially during a time period, while the electric stimulator 140 controls the parameters of the electrical current flowing through each channel independently of one or more parameters of the current flowing through another channel.

By independently controlling the flow of electrical current through each channel, the electric stimulator 140, and the orthosis 105 as a whole, is configured to steer the electrical current within the neuromuscular system of the limb 10, thereby promoting improved movement and positioning of a portion of the limb 10 (e.g., the foot) during a gait event, than that would otherwise be achieved via known systems utilizing single channel stimulation, as described in more detail herein.

The electric stimulator 140 can be configured to selectively switch each channel on to permit the flow of electrical current through the channel, or off to prevent or cease the flow of electrical current therethrough, even while providing the flow of electrical current via a different channel.

In some embodiments, the orthosis 105 of the system 100 can optionally include the sensor 130. The sensor 130 can be any suitable sensor device or can include a combination of sensor devices. For example, in some embodiments, the sensor 130 can include tilt sensor, an accelerometer, a gyroscope, a pressure sensor, a force sensitive resistor, a speedometer, a magnetometer, a goniometer or other mechanism for detecting and/or measuring angular displacement of the limb segment, and/or the like. In this manner, when the system 100 is used for gait modulation of a patient with an impaired limb (i.e., leg), the sensor 130 can be configured to sense and/or otherwise detect a characteristic associated with, for example, a gait event such as a position of the sensor 130 relative to the orthosis 105, a position of the limb 10 relative to a reference plane or the like, an angular position of the limb 10 relative to a reference plane or the like, velocity, rate of change in velocity (i.e., acceleration), tilt of the patient's foot, pressure (e.g., when the foot and/or shoe contacts a surface upon which the patient is walking), or the like. In some embodiments, the stimulator 140 is configured to determine the speed of a patient's gait, the patient's cadence during gait, whether the patient is in a swing phase or stance phase of gait, the patient's range of motion (lateral, posterior, and/or anterior), and whether the patient is sitting, based on a signal received from the sensor 130 based on one or more of the foregoing characteristics detected by the sensor 130.

In some embodiments, the sensor 130 can be included in and/or integrated with the frame assembly 110, the electrode assembly 120, and/or the electric stimulator 140. In other embodiments, the sensor can be physically distinct from the orthosis 105 and in electrical communication with the electric stimulator 140 via a wireless communication channel. For example, in some embodiments, the electric stimulator 140 can be coupled to the frame assembly 110, which in turn, is coupled to a first segment of the limb (e.g., adjacent to the knee of the patient's leg) and the sensor can be coupled to and/or otherwise can be associated with a second segment of the limb 10 (e.g., adjacent to the foot and/or ankle of the patient's impaired leg). In some embodiments, the sensor can be coupled and/or otherwise can be associated with a segment of the contralateral leg (e.g., adjacent to the foot and/or ankle of the patient's leg not donning the electric stimulator 140).

In some embodiments, the system 100 includes two or more sensors or sensor devices. For example, in some embodiments, the system 100 has a first sensor 130 included in the orthosis 105, such that the sensor is included in and/or integrated with the fame assembly 110, the electrode assembly 120 or the electric stimulator 140, and a second sensor (not shown in FIG. 1) physically distinct from the orthosis 105 (e.g., adjacent to the foot and/or ankle of the same limb on which the orthosis 105 is donned or of the contralateral limb). For example, in such an embodiment, the first sensor can include at least one of a gyroscope or an accelerometer included in or otherwise integrated with a component of the orthosis 105 and the second sensor can be a pressure sensor or force sensitive resistor disposed beneath a heel of the foot. In some embodiments, the system 100 can have one, two or more sensors included or integrated with the electric stimulator 140 and one, two or more sensors included in the frame assembly 110. For example, in some embodiments, the electric stimulator 140 includes a first gyroscope and the frame assembly 110 includes a second gyroscope. In another example, in some embodiments, the electric stimulator 140 can include two gyroscopes (or two other sensor or combination of sensors). In still another example, the frame assembly 110 can include two gyroscopes (or two other sensors or combination of sensors). In yet another example, the system 100 can include a gyroscope and an accelerometer (e.g., a three-axis accelerometer), which can both be physically integrated a single component (e.g., the electric stimulator 140, the frame assembly 110, the electrode assembly 120, or the like) of the system, integrated into different components of the system, coupled to a different portion of the orthosis 105, or physically distinct from the orthosis. The sensor(s) is configured to send a signal to the electric stimulator 140 based on a parameter associated with the patient's gait. In some embodiments, the electric stimulator 140 is configured (e.g., via the microprocessor) to calculate a gait parameter based on the signal received from the sensor.

As described above, in some instances, the system 100 can be used for gait modulation of patients with an impaired limb. More specifically, the system 100 can be used to enhance the limb function of a patient experiencing drop foot. In such instances, the patient can manipulate the orthosis 105 in such a manner as to couple the orthosis 105 to the impaired limb. For example, the patient can position the orthosis 105 adjacent to the knee of an impaired leg and can transition the frame assembly 110 from a first configuration to a second configuration (as described above) to removably couple the orthosis 105 to the leg.

The placement of the orthosis 105 can be such that a set of electrodes included in the electrode assembly 120 are disposed in a location relative to the leg that is associated and/or corresponds to a desired portion of the neuromuscular system of the leg. For example, as described above, one or more electrodes can be disposed in a location relative to one or more target nerves of the leg, and/or one or more electrodes can be disposed in a location relative to one or more target muscles of the leg. As described herein, when applied to different parts of the limb, current steering can be used to achieve balanced movement of at least a portion of the limb. More specifically, to enhance the leg function of a patient experiencing drop foot during gait, the orthosis 105 can be positioned relative to the leg to place one or more electrodes in electric communication with the peroneal nerve and/or the tibial nerve. Thus, the electrodes can transmit functional electrical stimulation to the peroneal nerve, which can result in dorsiflexion of the foot, the tibial nerve, which can result in plantarflexion of the foot, and/or one or more additional nerves or muscles of the leg, which can result in reduced or eliminated inversion or eversion of the foot (i.e., the foot is balanced in a neutral position or is moved towards a neutral position from an inverted or everted position) thereby enhancing the function of the impaired leg to mitigate the effects of drop foot, as described in further detail herein. In another example, the sciatic nerve (or, more specifically, the main branch of the sciatic nerve before the sciatic nerve divides into its two branches of the tibial nerve and the common peroneal nerve) can be stimulated to activate the hamstrings. In another example, the femoral nerve can be stimulated to activate the quadriceps.

With the frame assembly 110 retained in the desired position relative to the impaired leg, the patient can begin walking. During walking, the sensor 130 can be configured to sense and/or detect a set of characteristics (such as those described above) associated with a gait event and can send a signal associated with the characteristic to the electric stimulator 140. For example, in some embodiments, the gait event can be associated with a "heel-off" event (i.e., the point during gait at which the heel is lifted off the surface upon which the patient is walking). The sensor 130 can send the signal to the electric stimulator 140 via any suitable communication channel. For example, if the sensor 130 is collocated with at least a portion of the electric stimulator 140 and/or the frame assembly 110, the sensor 130 can send the signal via a communication channel associated with a wired signal transmission. If, however, the sensor 130 is physically distinct from the other portions of the orthosis 105, the sensor can send the signal via a communication channel associated with a wireless signal transmission, such as those described above. In some embodiments, the electric stimulator 140 can receive a signal from multiple sensors 130 that can be configured to sense and/or detect a characteristic associated with a gait event at different segments along the limb (e.g., leg) of the patient.

Figure 2:
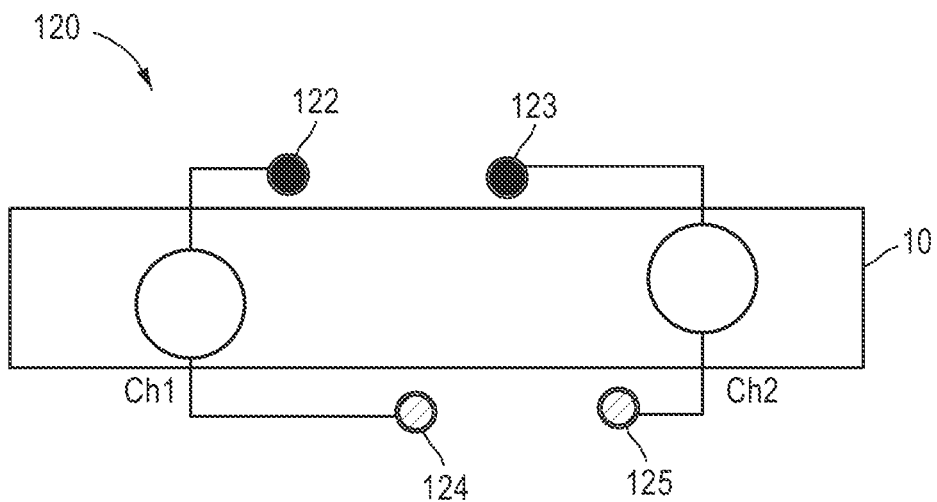
FIG. 2 is a schematic illustration of a set of stimulation channels formed, in part, by a set of electrodes of a functional electrical stimulation (FES) system according to an embodiment.

Upon receiving the signal from the sensor 130, the electric stimulator 140 can be configured to transmit an electrical current (e.g., generated by a power supply or the like included in the electric stimulator 140) along a first portion or channel of an electric circuit and along a second portion or channel of the electric circuit. Referring to FIG. 2, the current flowing via a first channel Ch1 of the electric circuit is transmitted to at least a first electrode 122 of the electrode assembly 120, through one or more nerves and/or muscles of the limb 10, and at least a portion of the current is returned through at least a second electrode 124 of the electrode assembly 120 to the electric stimulator 140. In this manner, the first channel Ch1 of stimulation includes the first electrode 122 and the second electrode 124, as shown in FIG. 2. The current flowing via a second channel Ch2 of the electric circuit is transmitted to at least a third electrode 123 of the electrode assembly 120, through one or more nerves and/or muscles of the limb 10, and at least a portion of the current is returned through a fourth electrode 125 of the electrode assembly 120 to the electric stimulator 140. In some embodiments, however, at least a portion of the current flowing in the second channel can be returned through the second electrode 124. In this manner, the second channel Ch2 of stimulation includes the third electrode 123 and the fourth electrode 125, and/or, in some embodiments, the second electrode 124.

Figure 3:
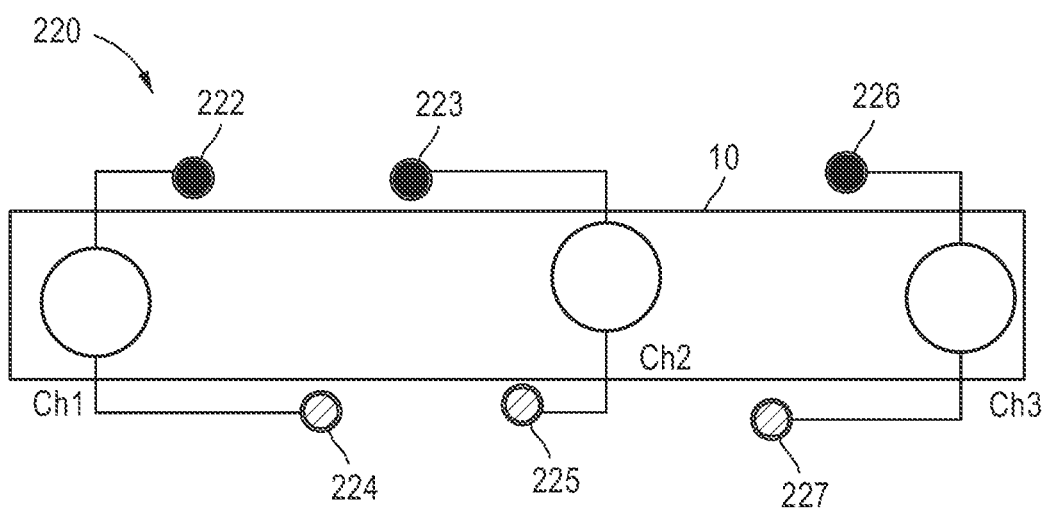
FIG. 3 is a schematic illustration of a set of stimulation channels formed, in part, by a set of electrodes of a functional electrical stimulation (FES) system according to an embodiment.
Figure 4:
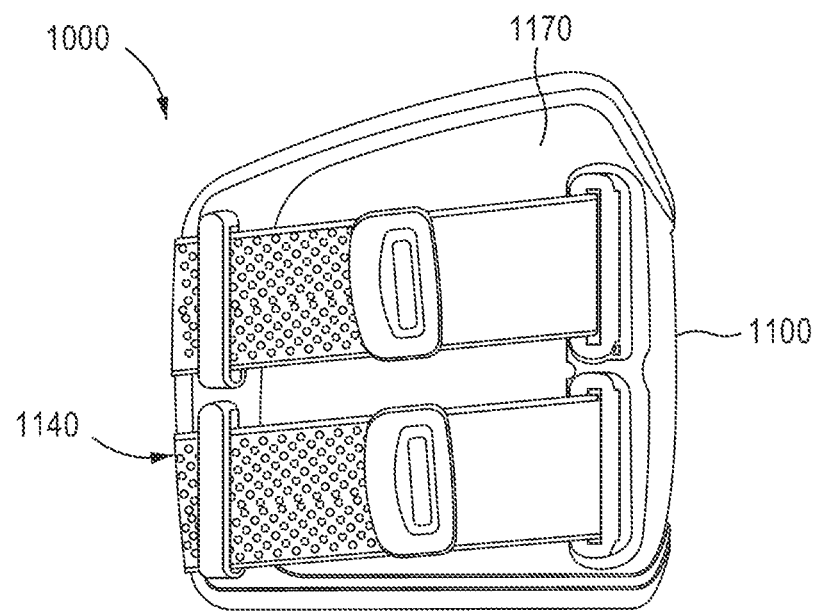

Optionally, in some embodiments, the electric stimulator 140 is configured to transmit an electrical current along a third portion or channel of an electric circuit, which is electrically coupled to the electrode assembly. Referring to FIG. 3, in some embodiments, electrical current is provided in a first channel Ch1 between a first electrode 222 of an electrode assembly 220 (which can be similar in many respects to electrode assembly 120) and a second electrode 224 of the electrode assembly, through one or more nerves or muscles of the limb 10, in a second channel Ch2 between a third electrode 223 and fourth electrode 225 of the electrode assembly 120, through one or more nerves or muscles of the limb 10, and via a third channel Ch3 between a fifth electrode 226 and a sixth electrode 227, through one or more nerves or muscles of the limb 10.

Although each of electrodes 224, 225 and 227 are shown and described above as returning a current from electrodes 222, 223 and 226, respectively, and thus forming a portion of the first, second and third stimulation channels, respectively, in some embodiments, one or more of electrodes 224, 225, and 227 can be selectively configured to return at least a portion of the current flowing from a different one or an additional one of electrodes 222, 223, 226. In this manner, for example, electrode 224 can selectively form a portion of the second channel Ch2 and/or the third channel Ch3 in addition to and/or instead of the first channel Ch1. In another example, electrode 225 can selectively form a portion of the first channel Ch1 and/or the third channel Ch3 in addition to or instead of the second channel Ch2. In still another example, electrode 227 can selectively form a portion of the first channel Ch1 and/or the second channel Ch2 in addition to or instead of the third channel Ch3.

The current flowing via each of the first and second (and, optionally, third) channels provides FES to one or more nerves or muscles of the limb, such as the peroneal nerve of the leg thereby resulting in dorsiflexion and/or plantarflexion of the foot as well as a neutral foot (or at least reduced inversion or eversion of the foot) substantially at the time of the heel-off event (e.g., a very short time after the sensor 130 detects the heel-off event consistent with a rate of electrical signal and/or electrical current transmission such as, 0.10 seconds, 0.05 seconds, 0.01 seconds, 0.001 seconds, 0.0001 seconds, or less). In some embodiments, electrical current flowing via the first channel has a first intensity and electrical current flowing via the second channel has a second intensity, which can promote a balanced or neutral foot position in conjunction with the foot's dorsiflexion (also referred to herein as "balanced dorsiflexion"). In other words, multiple-channel (e.g., dual-channel or triple-channel) FES is configured to reduce the degree of or eliminate eversion or inversion of the foot that may otherwise occur in the presence of dorsiflexion or plantarflexion of the foot resulting from single-channel FES. As a result, the foot of the patient flexes toward the leg and moves towards a neutral position, enhancing a portion of the patient's gait.

In some instances, the sensor 130 can sense and/or detect a characteristic associated with a second gait event such as, for example, a "heel-on" event (i.e., the point during gait at which the heel is placed in contact with the surface of upon which the patient is walking). As described above, the sensor 130 can send a signal associated with the characteristic to the electric stimulator 140 and, upon receipt, the electric stimulator 140 can terminate the flow of electrical current to the electrodes. In some embodiments, the electric stimulator 140 can send an electrical current along an electric circuit, such as via at least two of the first channel, the second channel, or an optional third channel of the electrical circuit, that is electrically coupled to one or more electrodes in electrical communication with one or more target nerves or muscles of the leg (e.g., the tibial nerve). Thus, the electrodes can provide FES to the tibial nerve resulting in a balanced or neutral foot position in conjunction with the foot's plantarflexion (referred to herein as "balanced plantarflexion") substantially at the time of the heel-on event (as described above). In this manner, the termination of the FES to a first target nerve (e.g., the peroneal nerve) relaxes the portion of the neuromuscular system resulting in a relaxation of the dorsiflexion, while substantially concurrently, the FES provided to a second target nerve (e.g., the tibial nerve) results in plantarflexion of the foot, and also substantially concurrently the FES is provided to at least another nerve and/or muscle of the leg to reduce and/or eliminate eversion or inversion of the foot. As such, the foot flexes away from the leg and the foot is in or moves toward a neutral position, thereby enhancing a portion of the patient's gait.

In some embodiments, the electric stimulator 140 can include a microprocessor, such as, for example, an application-specific integrated circuit (ASIC) or a combination of ASICs, which are designed to perform one or more specific functions. In some embodiments, the stimulator 140 can include an analog or digital circuit, or a combination of multiple circuits.

In some embodiments, the stimulator 140 can include a memory, such as, for example, a read only memory (ROM) component, a random access memory (RAM) component, electronically programmable read only memory (EPROM), erasable electronically programmable read only memory (EEPROM), and/or flash memory. In some embodiments, the electric stimulator 140 can include, for example, a memory or the like that can be configured to store information at least partially defining a set of parameters associated with the FES. For example, in some embodiments, the electric stimulator 140 can be configured to store information associated with an amplitude, voltage, pulse rate, waveform, and/or current level associated with the FES, a sensitivity associated with the sensor 130, a repository of actions to perform based on information received from the sensor 130, and/or any other suitable information and/or logic. Thus, the electric stimulator 140 can be configured to provide FES to the impaired leg with a set of characteristics that can be uniquely associated with the patient. In some embodiments, the electric stimulator 140 is configured to store data, including, but not limited to, usage data (e.g., historical data associated with the FES provided to the patient via the orthosis 105, including the set(s) of parameters associated with the FES, the frequency of use, the duration of use over a time period, e.g., on a daily, weekly and/or monthly basis), data associated with the patient's gait (e.g., multiple individual parameters associated with the patient's gait), data associated with the patient's number of daily steps taken, data associated with a distance traveled by the patient during gait or other physical activity (e.g., cycling, rowing, paddling, or the like), data associated with the patient's daily range of motion for the impaired limb, data indicative of the frame assembly or assemblies to which the electric stimulator has been coupled to (or attempted to be coupled to) and the duration of such coupling, or the like.

In some instances, the patient and/or a health care professional can manipulate the electric stimulator 140 to change one or more parameters and/or characteristics associated with the FES provided to the impaired leg. For example, in some embodiments, a health care professional can adjust (e.g., increase or decrease) the intensity of electrical current flowing via the first channel of the stimulator 140 and can adjust the intensity of electrical current flowing via the second channel of the stimulator 140 until a neutral foot position is achieved (e.g., the foot is in a neutral position or inversion or eversion of the foot is reduced), and the intensity for each channel resulting in the desired foot position can be stored as a parameter associated with the FES. More specifically, the health care professional can adjust the amplitude of the electrical current flowing via each of the first and second channels of the stimulator 140 until a neutral or balanced foot position and/or dorsiflexion is achieved, and the amplitude for each channel resulting in the desired foot position can be stored in the stimulator 140 as a parameter associated with the FES. Such adjustment of the one or more parameters can be performed, for example, by a healthcare professional during an initial session to set up the orthosis 105 with the patient, or during one or more other sessions, check-ups, or the like. Additionally such adjustment of the one or more parameters can be performed, in one embodiment, directly via a user interface of the electric stimulator 140 (e.g., accessible on or through the housing of the electric stimulator). In other embodiments, such adjustment can be performed via a control device distinct from the electric stimulator 140, as described in more detail herein with respect to control devices 3500, 3550. In some embodiments, the electric stimulator 140 is configured for wireless communication with the control device, as also described in more detail herein. More specifically, the electric stimulator 140 can be configured to receive a wireless signal from the control device, to send a wireless signal to the control device, or both. In this manner, for example, the electric stimulator 140 can be controlled via wireless signal(s) by the control device, and can wirelessly transmit to the control device data stored in the electric stimulator 140 (e.g., usage data or the like).

In some embodiments, at least one of the stimulator 140 (e.g., via the microprocessor or other suitable component therein) or the control device is configured to change one or more parameters and/or characteristics associated with the FES provided to the impaired leg. For example, in some embodiments, the stimulator 140 (and/or control device) is configured to receive one or more signals associated with the patient's gait from one or more sensors 130. The stimulator 140 (and/or control device) can be configured to process such signal(s) in a manner to measure, calculate or the like a different parameter associated with the patient's gait. The stimulator 140 (and/or control device) can be configured to change one or more parameters and/or characteristics associated with the FES provided to the impaired leg based on the measured or calculated parameter. For example, in some embodiments, the stimulator 140 is configured to receive from a gyroscope at a first time a signal associated with a first gait parameter (e.g., a first angle of a portion of the leg during a gait event, such as during a step or swing phase) and to receive from the gyroscope at a second time subsequent the first time a second signal associated with a second gait parameter (e.g., a second angle of the portion of the leg during the gait event or a subsequent gait event). Cumulatively, the first and second signals received by the stimulator 140 from the gyroscope are indicative of a range of motion of the limb. The stimulator 140 can be configured to measure or calculate (e.g., via execution of a set of stored instructions) a distance traveled on the first signal and the second signal. Said another way, the stimulator 140 can be configured to measure or calculate a distance traveled based on the range of motion measurements associated with the limb. In some embodiments, the stimulator 140 is configured to adjust one or more parameters associated with the FES based on the measured or calculated range of motion.

In some embodiments, the stimulator 140 is configured to send to the control device a signal associated with the first and second signals received from the gyroscope, and the control device is configured to calculate the distance traveled (or other gait parameter). The control device can be configured to send to the stimulator 140 a signal that includes instructions to adjust one or more parameters and/or characteristics associated with the FES based on the calculated distance traveled. The control device can be configured to send to the stimulator 140 a signal associated with the calculated distance traveled, and the stimulator can be configured to adjust, based on the received signal, one or more parameters and/or characteristics associated with the FES.

In some embodiments, at least one of the stimulator 140 (e.g., via the microprocessor or other suitable component therein) or the control device is configured to change one or more parameters and/or characteristics associated with the FES provided to the impaired leg based at least in part on motion capture technology. For example, in some embodiments, the FES system includes motion capture technology configured to image a portion of the limb (e.g., the patient's foot) during at least a portion of the gait cycle. The stimulator 140 (or the control device 160) can be configured to adapt one or more stimulation parameters based on the image, and more particularly, with one or more data points associated with the image, and optionally also based on one or more signals associated with the patient's gait received from one or more sensors 130. For example, the system can be configured to image the patient's foot during gait, and depending on whether data derived from the image indicated inversion or eversion of the foot, the stimulator 140 (or the control device 160) can adaptively adjust one or more stimulation parameters based on the data from the image, and optionally also based on one or more sensors received from one or more sensors 130.)

Figure 66:
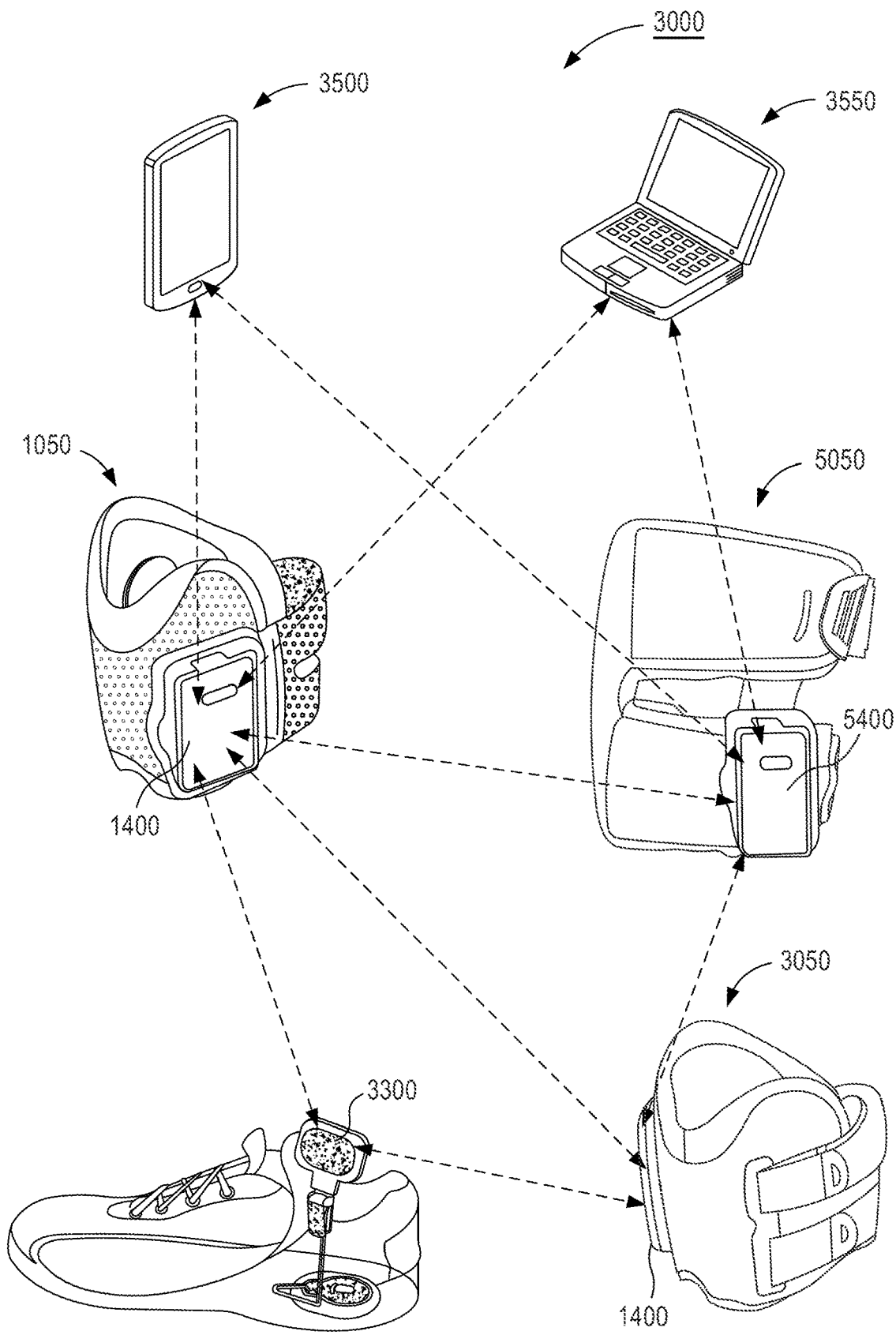
FIG. 66 is a schematic illustration of a FES system including the FES orthosis of FIG. 4 and the FES orthosis of FIG. 48, according to an embodiment.

In some embodiments, the electric stimulator 140 is configured for use with more than one orthosis (for example, as described in more detail with respect to FIG. 66). For example, the electric stimulator 140 can be configured for use with the FES orthosis 105, which can be an orthosis configured to be donned on the right leg of the user, and configured for use with a FES orthosis (not shown in FIG. 1) configured to be donned on the left leg of the user. Such an orthosis can be identical in function to the FES orthosis 105, however, components of the orthosis can be arranged in a substantially mirror image to facilitate placement on the opposing leg, and thus are not described in detail herein. The electric stimulator 140 can be configured for use with an orthosis configured to be disposed on a different limb or limb segment of the patient's body, such as the patient's upper leg or thigh, or the patient's arm. For example, the electric stimulator 140 can be configured for use with an orthosis 505, shown and described herein with respect to FIG. 47. In such embodiments, the electric stimulator 140 can be configured to store information associated with each FES orthosis (e.g., in the stimulator's memory), including one or more stimulation parameters associated with each FES orthosis. In some embodiments, the electric stimulator 140 includes a sensor or other mechanism configured to detect to which orthosis the stimulator is coupled. In some embodiments, the orthosis 105 includes an identification mechanism configured to be detected and/or read by the stimulator 140 and by which the stimulator can determine to which orthosis the stimulator is coupled. In this manner, the electric stimulator 140 can be configured to select a stimulation program, or the like, based on the detected orthosis. In some embodiments, the stimulator 140 is configured to determine whether it is programmed for use with an orthosis. The stimulator 140 can be configured to prevent initiating an electrical current or stimulation signal if the stimulator 140 determines that it is not programmed for use with the orthosis. In some embodiment, the stimulator 140 can be configured to provide an indicium that it has determined that it is not programmed for use with the orthosis. The indicium can be, for example, audible (e.g., a beep, alarm or other audible signal), visual (e.g., a displayed message, light, symbol, or the like), or tactile (e.g., a vibration or the like), or any combination of the foregoing. In some embodiments, the electric stimulator 140 is configured to be in electrical communication with an electric stimulator of another orthosis, as also described herein with respect to FIG. 66.

As shown in FIG. 1, in some embodiments, the electric stimulator 140 can be in communication with a control device 160. The control device 160 can be any suitable electronic device that can provide an interface for a user (e.g., the patient and/or a health care professional) to manipulate one or more characteristics and/or parameters associated with the FES. For example, in some embodiments, the control device 160 can be, for example, a personal computer (PC), a personal digital assistant (PDA), a smart phone, a laptop, a tablet PC, a server device, a workstation, and/or the like. The electronic device can include at least a memory (e.g., a random access memory (RAM), a memory buffer, a hard drive, a read-only memory (ROM), an erasable programmable read-only memory (EPROM), and/or the like); a processor (e.g., a general purpose processor, a central processing unit (CPU), an accelerated processing unit (APU), and Application Specific Integrated Circuit (ASIC), and/or the like); a network interface (e.g., a network interface card and/or the like that can include at least an Ethernet port and/or a wireless radio (e.g., a WiFi® radio, a Bluetooth® radio, etc.)); and an output device (e.g., a display such as a cathode ray tube (CRT) monitor, a liquid crystal display (LCD) monitor, a light emitting diode (LED) monitor, and/or the like, a Universal Serial Bus (USB) drive, an ANT+ compatible device or application, and/or any other suitable output device). In this manner, the control device 160 can be in communication with the electric stimulator 140 via the network interface and the processor can be configured to run or execute a set of instructions or code stored in the memory associated with using, for example, a PC application, a mobile application, an internet web browser, a cellular and/or wireless communication (via a network), and/or the like to communicate with and/or otherwise control at least a portion of the electric stimulator 140, as described herein with respect to specific embodiments. In such embodiments, the electric stimulator 140 can be devoid of a user interface, such as a user interface accessible via an outer surface of a housing of the stimulator, thereby reducing manufacturing costs for the stimulator, simplifying usage of the FES system 100, and also reducing potential damage to the electrical circuit that may occur in the event of moisture ingress via such a user interface.

FIGS. 4-22 are illustrations of portions of a system 1000 used, for example, in gait modulation according to an embodiment. For example, in some instances, the system 1000 can be used by a human patient who has one or more impaired limbs as a result of injury and/or disease (e.g., stroke, spinal cord injury, head injury, cerebral palsy, multiple sclerosis, etc.). More specifically, the system 1000 includes a functional electrical stimulation (FES) orthosis 1050 (also referred to herein as "orthosis" and/or "device") that is placed in physical and electrical contact with, for example, a lower limb segment of an impaired leg (not shown in these figures). In some embodiments, at least a portion of the orthosis 1050 can be substantially similar in form and/or function to those described in the '556 patent, the '036 patent, the '110 patent, and/or the '340 application incorporated by reference in their entireties above, or any other orthosis shown and/or described herein (e.g., orthosis 105). As such, the patient and/or a health care professional (e.g., doctor, nurse, technician, physician, physical therapist, etc.) can engage the system 1000 in such a manner as to cause the orthosis 1050 to selectively provide functional electrical stimulation to a portion of a neuromuscular system of the leg, which can, in turn, facilitate gait of the patient who might otherwise experience, for example, drop foot or the like, as described in further detail herein.

As shown in FIGS. 4-22, the orthosis 1050 includes a frame assembly 1100, an electrode assembly 1200, and an electric stimulator 1400. Although not shown in FIGS. 4-22, the orthosis 1050 can also include and/or otherwise be operably coupled to one or more sensors shown and described herein.

The frame assembly 1100 is configured to be removably coupled to a portion of a limb such that the portion of the limb is substantially enveloped by the frame assembly. The frame assembly 1100 of the orthosis 1050 can have any suitable shape and/or size that can be, for example, associated with a segment of the leg and includes at least a portion that can be transitioned between a first (or open) configuration and a second (or closed) configuration to couple the frame assembly 1100 to the leg. In some embodiments, the frame assembly 1100 can have a shape and size that are associated with a portion of the lower leg (e.g., between the knee and the foot of the lower leg). As such, an upper portion 1105 of the frame assembly 1100 can form an ergonomic contour (e.g., a locator portion 1106) that can, for example, substantially correspond with a shape of an inferior border of a patella of a knee of the leg. A lower portion 1115 of the frame assembly 1100 can form an ergonomic contour (e.g., a locator portion 1117) that can, for example, substantially correspond with a shape of the tibial crest. Moreover, the frame assembly 1100 can define an ergonomic cross-sectional shape taken about a plane that is normal to a longitudinal axis of the frame assembly 1100 (e.g., substantially coaxial with an axis defined by the segment of the leg) that corresponds to and/or otherwise is associated with a shape of a tibial crest of the lower leg. The orthosis 1105 optionally includes a visual locator 1104 that is configured to be aligned with a predetermined portion of the patient's anatomy (e.g., a center of the knee, the tibial crest, or the like). In some embodiments, the frame assembly 1100 can be substantially similar in form and/or function as those described in the '556 patent, the '036 patent, the '110 patent, and/or the '340 application, incorporated by reference above, or any frame assembly described herein (e.g., frame assembly 110).

As shown in FIGS. 4-16, the frame assembly 1100 includes a frame 1110 (also referred to herein as a "first layer" or "inner structure"), a cradle 1130, a coupling portion 1140, an inner layer 1160 (also referred to herein as a "second layer"), and an outer layer 1170 (also referred to herein as a "third layer" or "cover"). At least a portion of the frame assembly 1100, such as the frame 1110, can be formed from a semi-rigid material such as, for example, a relatively thin metal, a thermoplastic, a polymer, and/or the like. In this manner, the frame 1110 can be sufficiently rigid to provide structural support for the orthosis 1050, while being sufficiently flexible to allow the limb about which the frame 1110 is disposed to increase or decrease during, for example, muscle flexion or muscle relaxation, respectively.

As shown in FIGS. 9-13, the frame 1110 can be substantially C-shaped such as to allow the frame 1110 to expand and contract in response to the expansion and contraction of the leg, respectively. Moreover, the arrangement of the frame 1110 can be such that when the size of the leg is reduced (e.g., after expansion due to muscle flexion), the rigidity of the frame 1110 can be sufficient to transition the frame 1110 to a size and shape associated with the reduced size of the leg. Similarly stated, the frame 1110 can be biased such that when an external force that expands the frame 1110 to an expanded size is removed, the frame 1110 returns to an unexpanded size, smaller than the expanded size. For example, the frame 1110 can include one or more spring members (not shown) coupled to the frame 1110 and configured to bias opposing ends of the frame 1110 towards each other, as indicated by arrows A and B in FIG. 10, thus reducing a cross-sectional area defined within the C-shaped of the frame 1110. A first spring member can be coupled to the frame 1110 at one or more upper spring connectors 1113 formed on an upper portion of the frame 1110, and a second spring member can be coupled to the frame 1110 at one or more lower spring connectors 1112, 1114 formed on a lower portion of the frame 1110. Note that reference to "upper" and "lower" in this section refer to respective positions when the frame assembly 1100 is donned on the leg of a standing patient. In the absence of such spring members, in use, the opposing ends of the frame 1110 can tend to move away from each other, as indicated by arrows C1 and C2 in FIG. 11.

In another example, the frame 1110 can be constructed of an inner portion 1116 and an outer portion 1118. In this manner, at the manufacturing stage, the inner portion 1116 can be formed, and then the outer portion 1118 of the frame 1110 can be over-molded or otherwise coupled to the inner portion of the frame 1110. The inner portion 1116 of the frame 1110 includes a plurality of retaining members 1120, 1122, 1124, 1126, each of which is inwardly biased towards the interior volume defined by the C-shaped frame 1110. Although the inner portion 1116 is shown and described as included four retaining members 1120, 1122, 1124, 1126, in other embodiments, any suitable number of retaining members may be included in the inner portion of the frame (e.g., one, two, three, five, or more).

Figure 10:
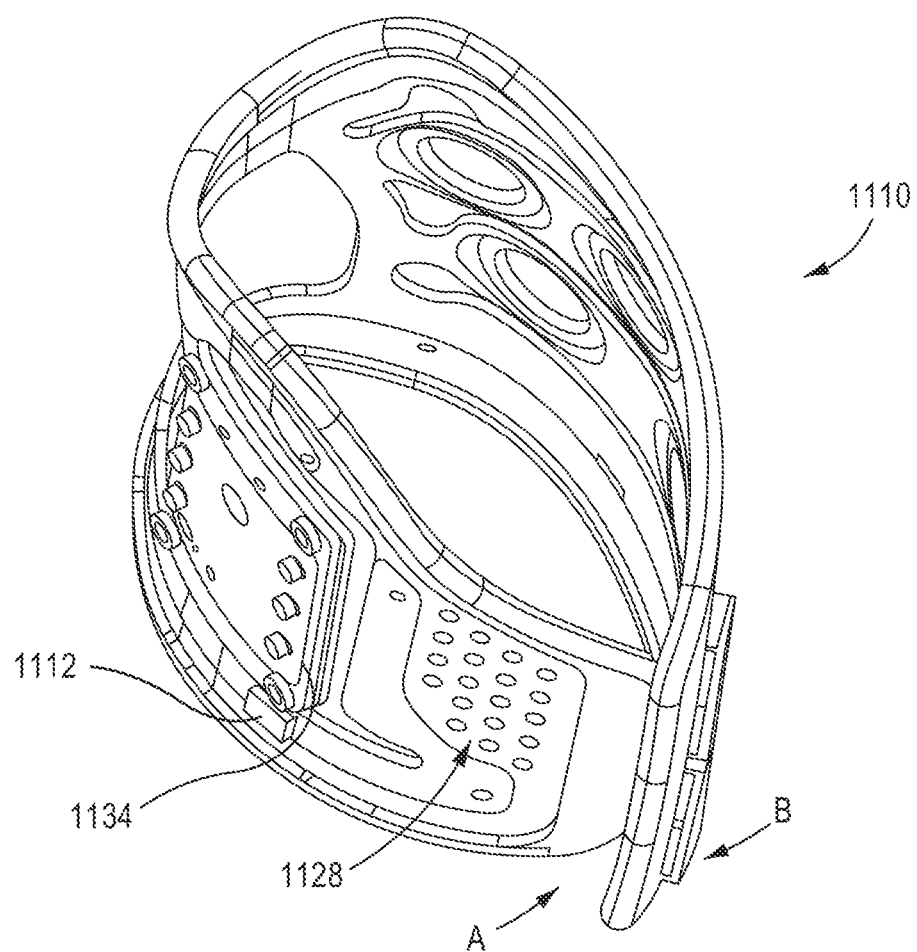
FIGS. 10-11 are perspective views of the portion of the frame assembly of the FES orthosis of FIG. 4 in a first configuration and a second configuration, respectively.
Figure 11:
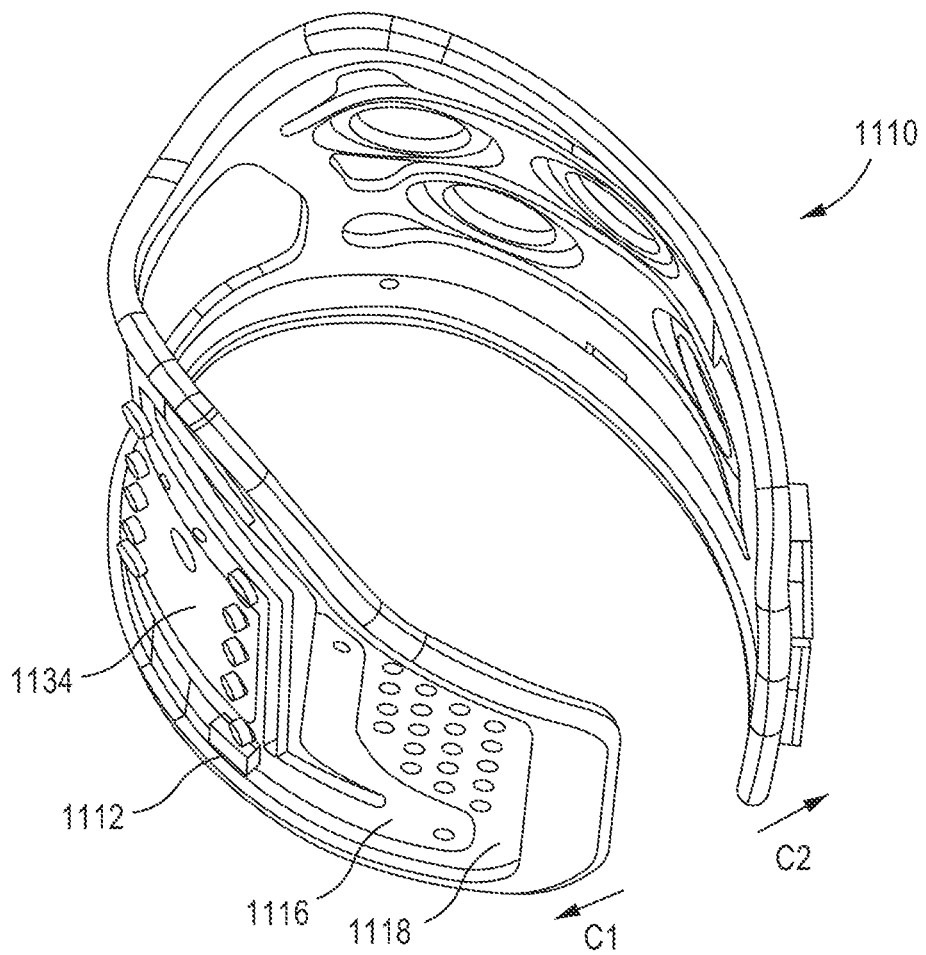
Figure 12:
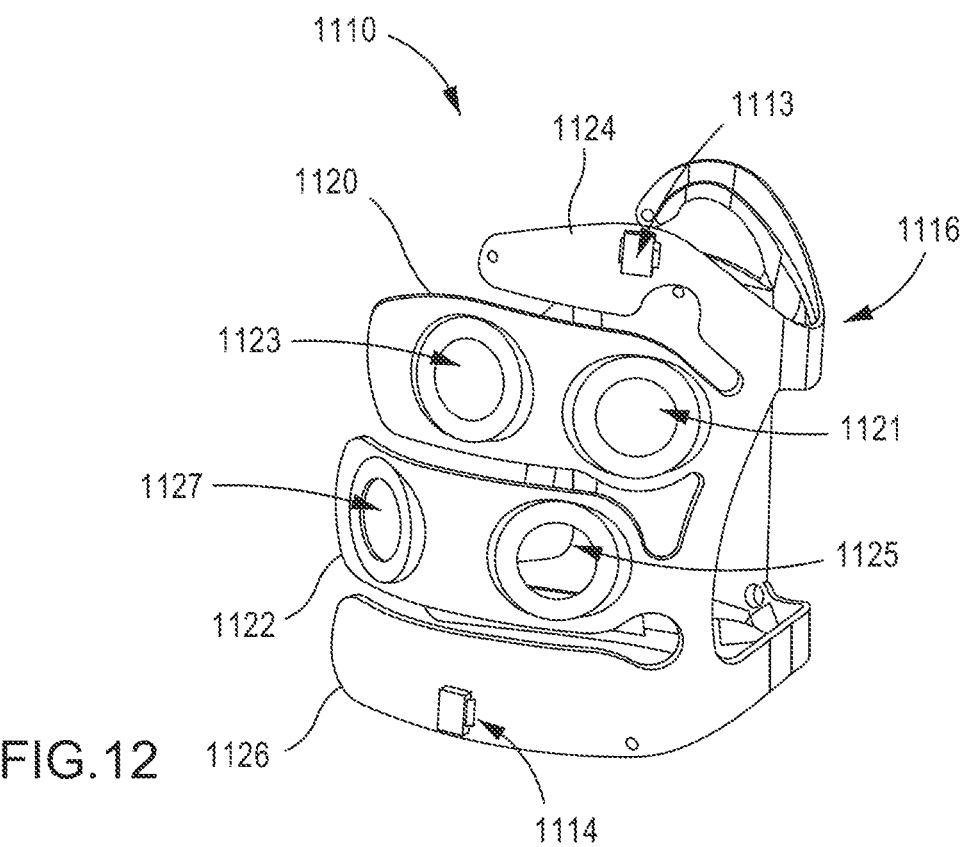
FIGS. 12-13 are a side view and a perspective view, respectively, of the a portion of the frame assembly of the FES orthosis of FIG. 4.
Figure 13:
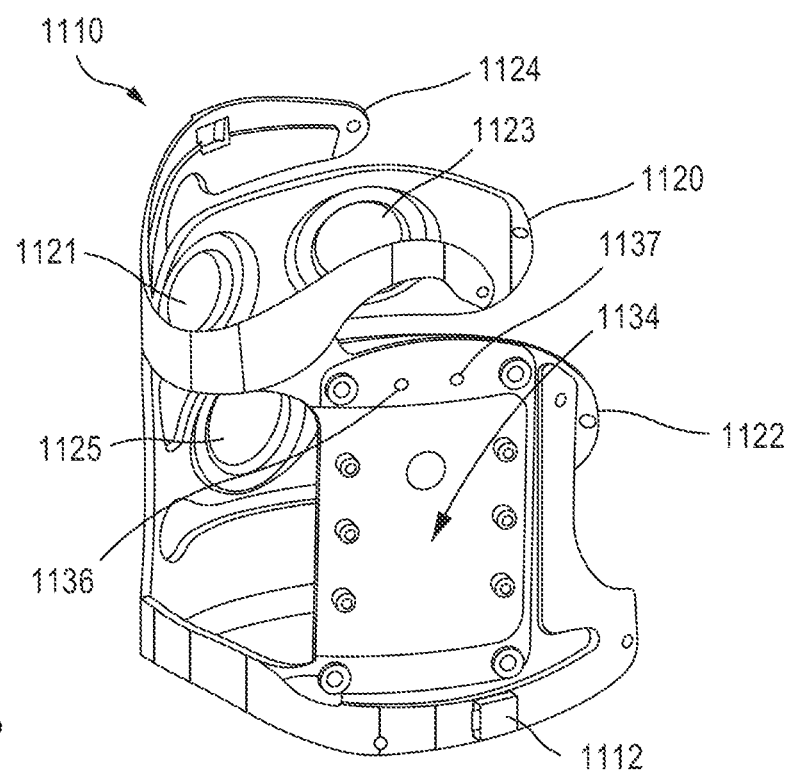

Thus, this arrangement enables the frame assembly 1100 to substantially envelop the portion of the leg, and serves to effectively disperse a pressure and/or strain that would otherwise be exerted on the portion of the leg, thereby retaining the natural profile and geometry of the leg tissue and/or muscles when coupled thereto. In some embodiments, at least a portion of the frame 1110, such as one or more portions of the inner portion 1116 of the frame, can define a plurality of openings 1128 configured to allow airflow through the frame, as shown in FIG. 10, and thus enhance patient comfort. In some embodiments, the frame 1110 can be substantially similar in form and/or function as a central frame or inner structure described in the '556 patent, the '036 patent, the '110 patent, and/or the '340 application, incorporated by reference above.

The inner layer 1160 (see, e.g., FIGS. 6 and 15) of the frame assembly 1100 is configured to substantially cover an inner surface of the frame 1110. The inner layer 1160 can be formed from any suitable material and/or combination of materials. For example, in some embodiments, the inner layer 1160 can be formed from a relatively flexible and/or soft material that can elastically deform when exposed to an external force. At least a portion of the inner layer 1160 can be formed from a brushed fabric, a hook and/or loop material, or the like, such as those offered commercially by Nam Liong Enterprise Co., Ltd. In this manner, the inner layer 1160 can be configured to help retain the electrode assembly 1200 to the frame assembly 1100. More specifically, at least a portion of the inner layer 1160 can include a hook and/or loop material configured to engage with and couple to a complementary material (e.g., the other of the hook and/or loop material) on an electrode base (not shown).

Also in this manner, the inner layer 1160 can enhance the ergonomics (e.g., comfort) of the frame assembly 1100 by forming a relatively flexible and/or soft layer that is placed in contact with the patient. In some embodiments, at least a portion of the inner layer 1160, such as a portion of the inner layer 1160 defining openings 1162, 1164, 1166, 1168, is formed of a polypropylene material.

Figure 16:
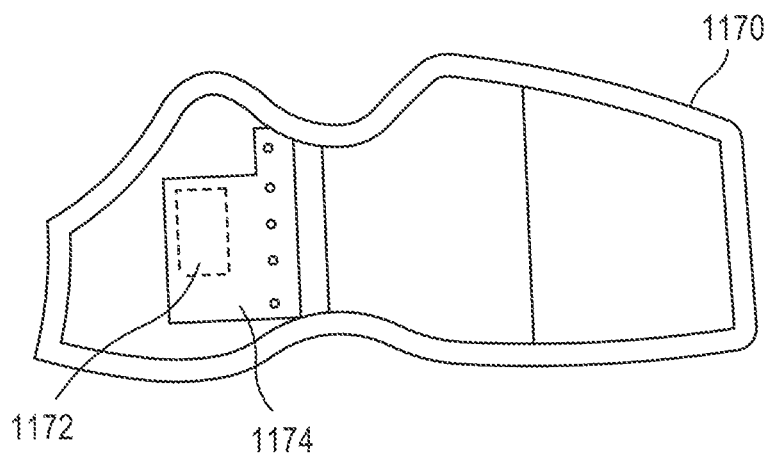
FIG. 16 is a rear view of a portion of a frame assembly of the FES orthosis of FIG. 4 in an uncoupled configuration.

The outer layer 1170 of the frame assembly 1100 can be configured to be disposed on an outer surface of the frame 1110. Referring to FIG. 16, the outer layer 1170 defines an opening 1172 (shown in dashed lines in FIG. 16) configured to be disposed about at least a portion of the cradle 1130. The outer layer 1170 can be formed from any suitable material and/or combination of materials. In some embodiments, the outer layer 1170 can be formed from a relatively flexible and/or soft material that can elastically deform when exposed to an external force. For example, the outer layer 1170 can be formed, at least in part, from elastane or spandex (such as Lycra®) or any other suitable material. In this manner, the outer layer 1170 can enhance the ergonomics (e.g., comfort) of the frame assembly 1100 by forming a relatively flexible and/or soft layer that may contact with the patient. In some embodiments, the outer layer 1170 includes a membrane 1174 extended from an inner surface of the outer layer 1170 and configured to be inserted between portions of the frame 1110 such that the membrane 1174 is disposed on an inner surface of a base plate 1134 of the frame 1110. The membrane 1174 can be configured, for example, to help limit the ingress of moisture (e.g., water, sweat, or the like) into the frame assembly 1100 that may enter through an opening of the cradle 1130.

Figure 17A:
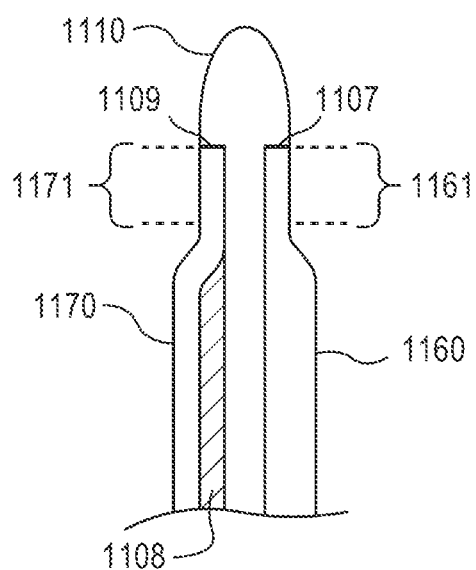
FIGS. 17A-17B are cross-sectional views of portions of the frame assembly of the FES orthosis of FIG. 4 according to embodiments.
Figure 17B:
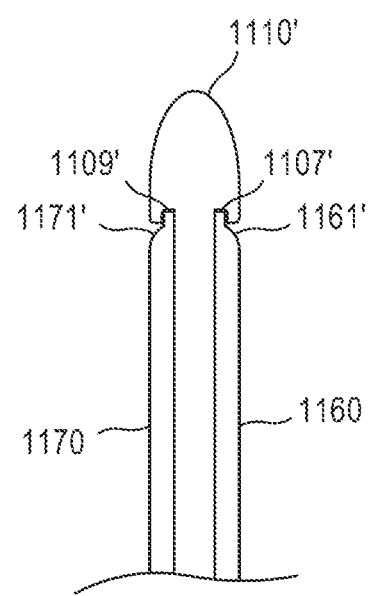

The inner layer 1160 and the outer layer 1170 can be coupled to the frame in any suitable manner. In some embodiments, for example, at least one of the inner layer 1160 and the outer layer 1170 is welded to the frame 1110. As shown in FIG. 17A, the inner layer 1160 and outer layer 1170 can each abut a shoulder portion 1107, 1109, respectively, formed by an edge of the frame 1110 and be welded at regions 1161, 1171, respectively, to the frame 1110. As also shown in FIG. 17A, in some embodiments, the frame assembly 1100 includes a layer of padding 1108 disposed between at least a portion of the outer layer 1170 and the frame 1110. In some embodiments, such padding 1108 can be integrally formed with the outer layer 1170. In another example, as shown in FIG. 17B, in some embodiments, an edge of the frame 1110' defines an inner channel 1107' and an outer channel 1109'. Edges 1161', 1171' of the inner layer 1160 and the outer layer 1170, respectively, are disposed in the channels 1107', 1109', respectively, and are welded to the frame 1110'. In other embodiments, at least one of the inner layer 1160 and the outer layer 1170 can be, for example, over-molded about portions of the frame 1110, 1110'. In still other embodiments, at least one of the inner layer 1160 and the outer layer 1170 can be removably disposed about or coupled to the frame 1110, 1110'.

Figure 18A:
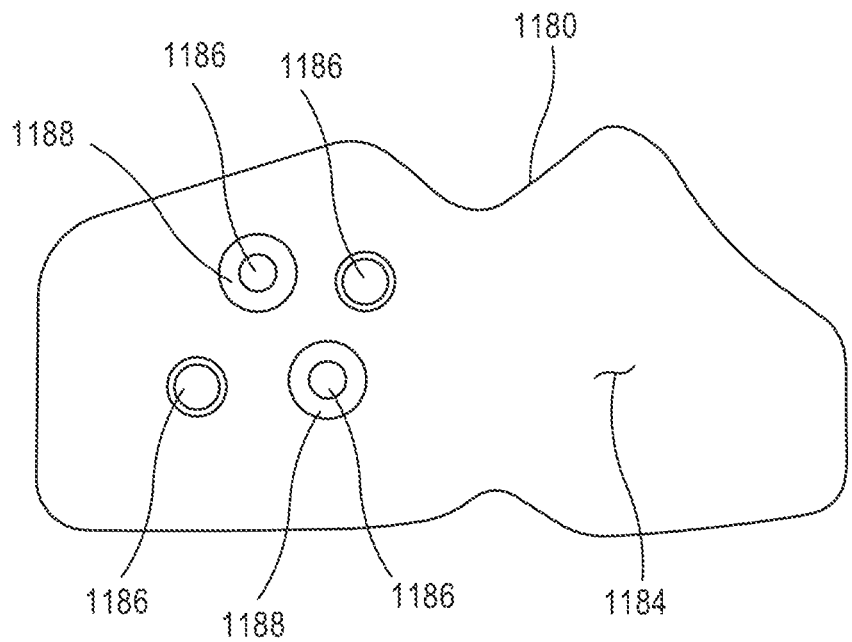
FIGS. 18A-18B are front and rear views, respectively, of a portion of a frame assembly of the FES orthosis of FIG. 4, in an uncoupled configuration.
Figure 18B:
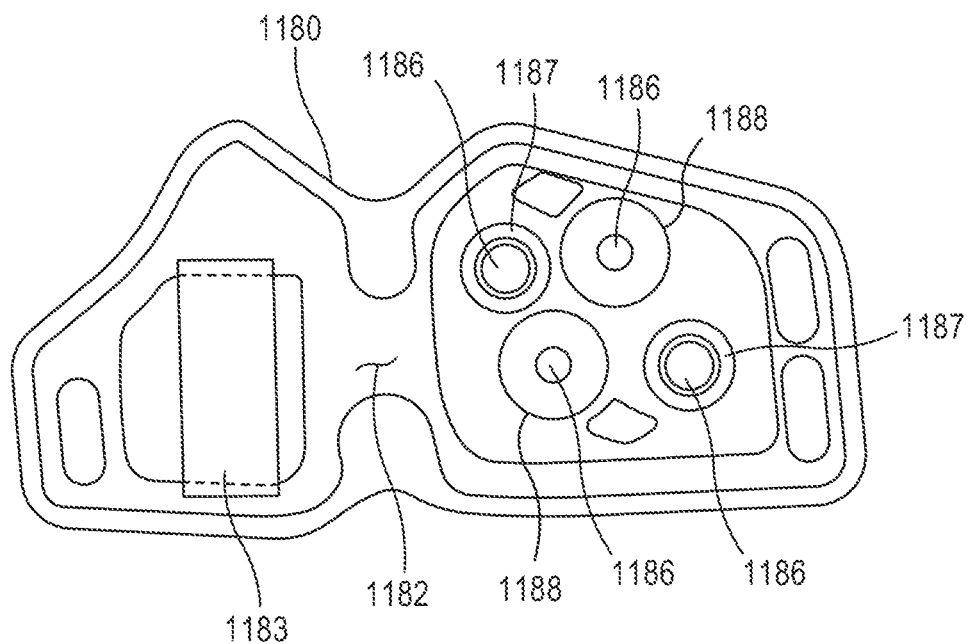

In some embodiments, as shown in FIGS. 18A-18B, the frame assembly 1100 includes a removable layer or panel 1180 that is removably coupleable to an inner surface (e.g., the inner layer 1160) of the frame assembly. The panel 1180 can, for example, provide a hygienic barrier between the frame assembly 1100 and the patient's body during use, thus facilitating the frame assembly 1100 to be shared between or used on multiple patients or users in a more sanitary manner. The removable panel 1180 includes a first side 1182, at least a portion of which is configured to be in contact with at least a portion of an inner surface (e.g., the inner layer 1160) of the frame assembly 1100. The panel 1180 includes a second side 1184, opposite the first side 1182, at least a portion of which is configured to be in contact with the limb segment. The panel 1180 can be removably coupled to the frame assembly 1100 in any suitable manner, including, but not limited to, a hook and loop fastener, a clip, a snap connector, a magnet, a protrusion and receiving sleeve or recess combination, or any other suitable fastening mechanism, or combination thereof. For example, in some embodiments, the first side 1182 of the removable panel 1180 includes at least a portion of a hook and loop fastener configured to removably couple to a complementary portion of the hook and loop fastener disposed on an inner surface (e.g., the inner layer 1160) of the frame assembly 1100. In another example, the first side 1182 of the removable panel 1180 includes a strap 1183 (see, e.g., FIG. 18B) connected at each end to the panel 1180 and that is configured to receive therethrough a portion of frame assembly 1100 (e.g., of the inner layer 1160) to removably couple the panel 1180 to the frame assembly 1100.

The removable panel 1180 can have a perimeter profile that is substantially similar to the perimeter profile of the inner surface (e.g., the inner layer 1160) of the frame assembly 1100, including, for example, contoured portions corresponding to the locator portions of the frame assembly. In this manner, the panel 1180 can substantially prevent direct contact between the inner layer 1160 of the frame assembly 1100 and the limb segment during use. Also in this manner, in some embodiments, substantially no portion of the panel 1180 extends beyond the perimeter profile of the frame assembly 1100 (e.g., of the inner layer 1160 of the frame assembly).

The removable panel 1180 defines a set of connector openings 1186 through which at least a portion of the electrode assembly 1200 can be disposed. For example, one or more wires 1240, 1242, 1244, 1246 of the electrode assembly 1200 can each be disposed through a respective opening of the set of connector openings 1186 to electrically couple the electrode assembly 1200 to the electric stimulator 1400. The set of openings 1186 can include one, two, three, four (as shown in FIGS. 18A-18B), five, six, or more connector openings. Although the openings 1186 are shown as being substantially circular in shape, in other embodiments, the openings can be any suitable shape or dimension. In some embodiments, a polypropylene layer 1187 is circumferentially disposed about one or more openings of the set of openings 1186 on the first side 1182 of the panel 1180. Although the polypropylene layer 1187 is shown and described as circumscribing an entirety of the circumference of the opening 1186, in some embodiments, the polypropylene layer is circumferentially disposed about a portion of the opening. In some embodiments, the polypropylene layer 1187 or a layer of another suitable material is disposed around each opening in the set of openings 1186, or only a portion of the openings in the set of openings.

In some embodiments, a fastener 1188 (or portion thereof) is circumferentially disposed about one or more openings of the set of openings 1186 on the second side 1184 of the panel 1180. For example, as shown in FIG. 18A, at least a portion of a hook and loop fastener (e.g., such as that commercially marketed as Velcro®) is circumferentially disposed about one or more openings 1186. Although the fastener 1188 is shown and described as circumscribing an entirety of the circumference of the opening 1186, in some embodiments, the fastener is circumferentially disposed about a portion of the opening 1186. In this manner, the fastener is configured to couple at least a portion of the electrode assembly 1200

(e.g., an electrode base of the electrode assembly) to the panel 1180, and thus to the frame assembly 1100.

Figure 14:
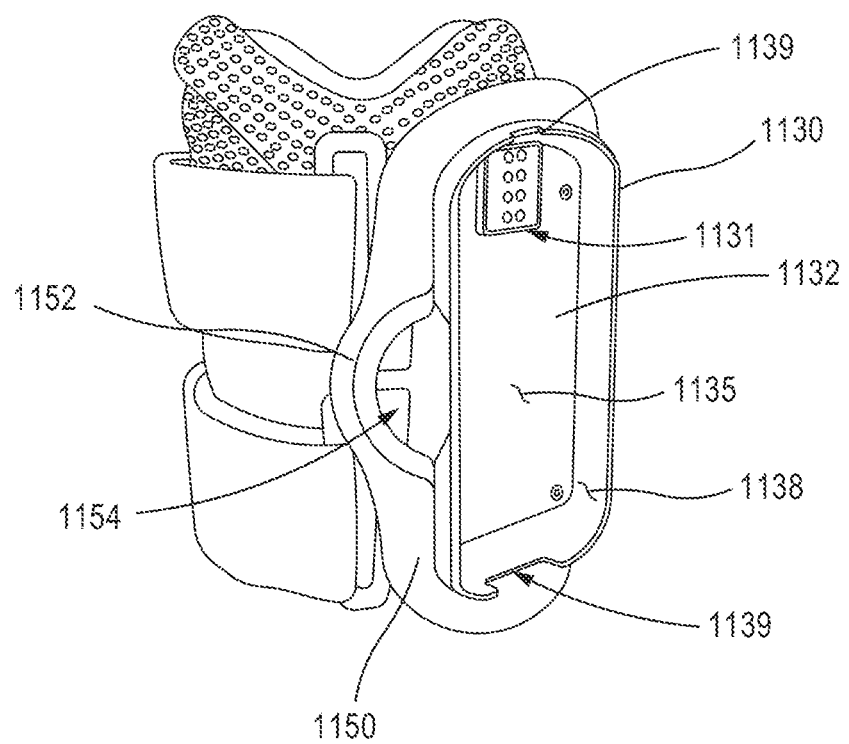
FIG. 14 is a side view of a portion of the frame assembly of the FES orthosis of FIG. 4.

The cradle 1130 of the frame assembly 1100 is disposed on the frame 1110 to define a receiving portion 1132 (see, e.g., FIG. 14) on or within which the electric stimulator 1400 (e.g., a housing of the electric stimulator) can be at least partially disposed. The base plate 1134 (see, e.g., FIG. 13) defined by the frame 1110 can be coupled to, and provide support for, the cradle 1130 coupled thereto. The base plate 1134 can include openings 1136, 1137 through which the electrodes can be coupled to the stimulator 1400 (e.g., via one or more wires or connectors). The cradle 1130 includes a rear wall 1135 and one or more walls 1138 extended from the rear wall (e.g., from a perimeter or portion thereof of the rear wall). The receiving portion 1132 is defined by the rear wall 1135 and the one or more walls 1138 extended from the rear wall. In some embodiments, as shown in FIG. 14, at least one wall 1138 can define a cut-out or recess 1139 configured to facilitate gripping of the stimulator 1400 by the user, for example, during removal of the stimulator 1400 from the cradle 1130. As shown, the wall 1138 defines a recess 1139 at opposing ends (e.g., the top and bottom) of the cradle 1130, however, in other embodiments, the wall can define a single recess (e.g., disposed at a top, bottom, or side of the cradle) or two or more recesses at different locations of the wall (e.g., at opposing side portions of the wall extending between the top and bottom of the cradle).

The cradle 1130 can include any suitable surface finish, protrusion, detent, etc. that can act to at least temporarily retain the electric stimulator 1400 within or with respect to the set of walls forming the cradle 1130. For example, in some embodiments, the cradle 1130 can form and/or define a set of detents that can matingly receive a set of corresponding protrusions extending from an outer surface of the electric stimulator 1400 when therein (or vice versa). In some embodiments, the stimulator can be coupled to and retained by the cradle using single or multiple snap-fit connectors. In other embodiments, an inner surface of the cradle 1130 can have a finish and/or can be formed from a material with a relatively high coefficient of friction. Thus, when the electric stimulator 1400 is disposed on the cradle 1130, an outer surface of the electric stimulator 1400 and an inner surface of the cradle 1130 can form and/or define a friction fit that can at least temporarily retain the electric stimulator 1400 in the cradle 1130.

As shown in FIG. 14, the cradle 1130 includes and/or forms a set of connectors 1131 via which the orthosis 1050, and more specifically connectors (not shown) of the electrode assembly 1200 (or a connection assembly), can be electrically coupled to corresponding connectors (not shown) of the electric stimulator 1400. Therefore, when the electric stimulator 1400 is positioned on the cradle 1130, the electric stimulator 1400 is placed in electrical communication with the electrode assembly 1200, as described in further detail herein.

Figure 5:
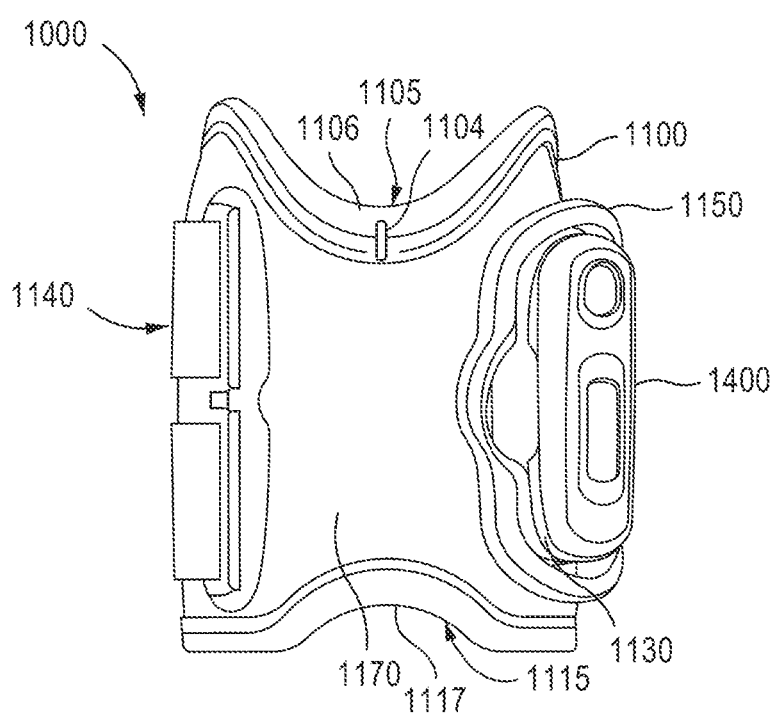
Figure 7:
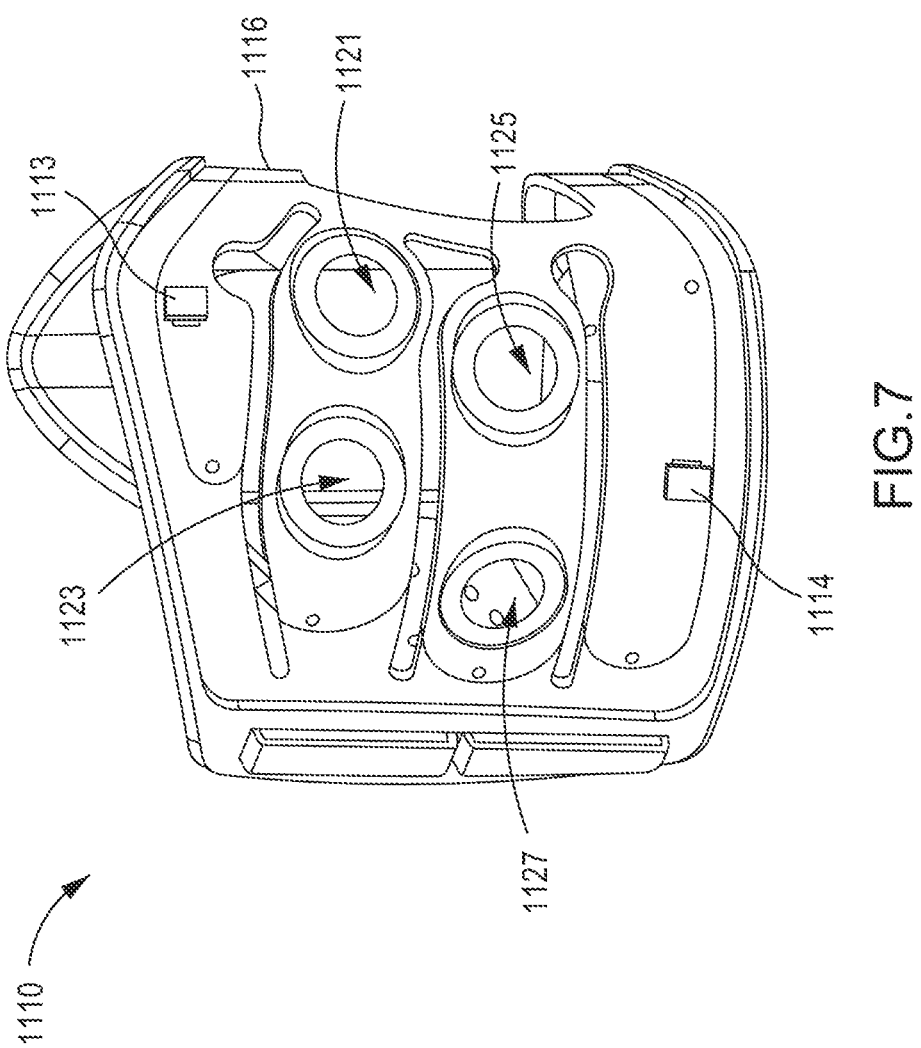
FIGS. 7-9 are side views and a perspective view, respectively, of a portion a frame assembly of the FES orthosis of FIG. 4.
Figure 8:
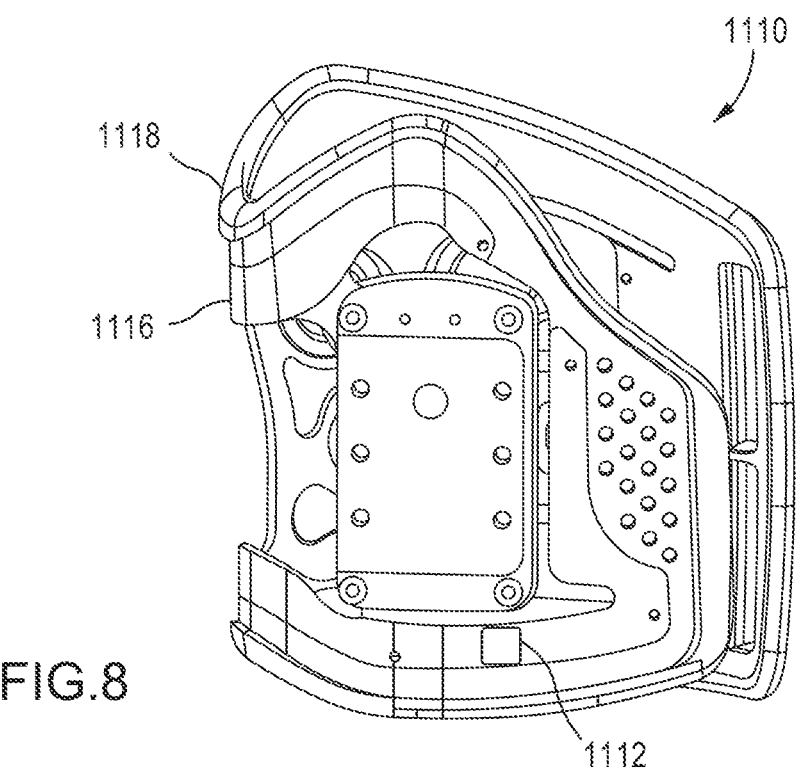
Figure 9:
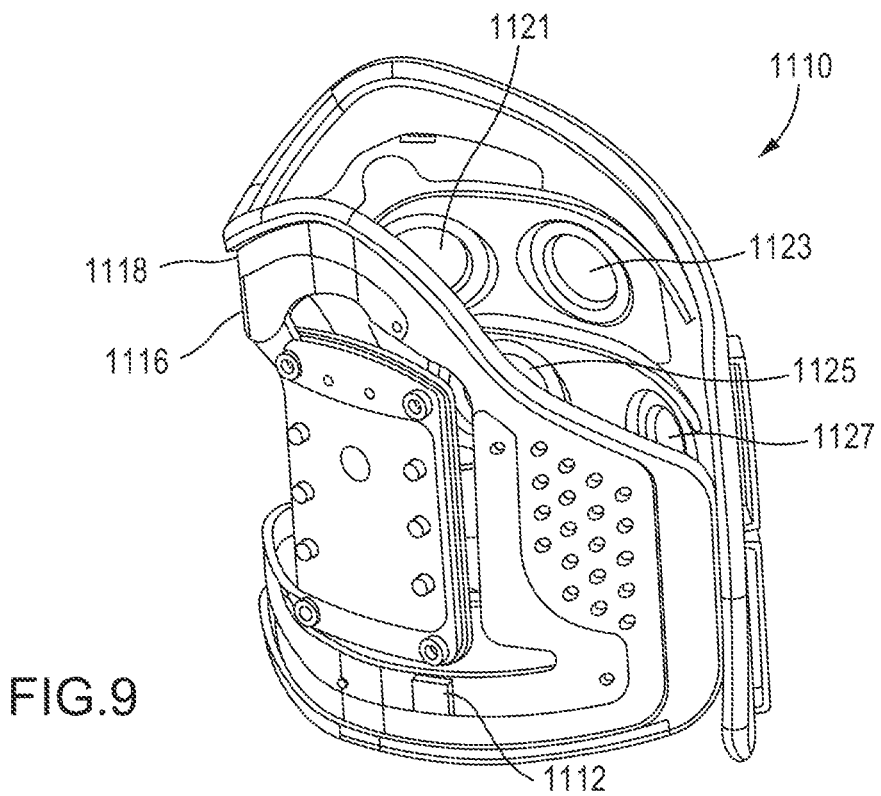

The coupling portion 1140 of the frame assembly 1100 can be transitioned between a first (e.g., open) configuration and a second (e.g., closed) configuration (e.g., as shown in FIG. 6) to reversibly couple the frame assembly 1100 to the leg. Said another way, the frame assembly 1100 can be positioned about a portion of the leg and the coupling portion 1140 can be transitioned to the second configuration to removably couple (i.e., at least temporarily couple) the frame assembly 1100 to the leg. The coupling portion 1140 includes substantially parallel, modular straps 1142, 1144 (e.g., elastic straps, inelastic straps, and/or straps including one or more elastic portions and one or more inelastic portions) connecting between the frame assembly 1100 and a handle 1150. The handle 1150 is coupled at an end portion of each strap 1142, 1144 (see, e.g., FIG. 6), and an opposing end of each strap 1142, 1144, respectively, is coupled to the frame assembly 1100 (see, e.g., FIGS. 4 and 5). The arrangement of the coupling portion 1140 is such that during donning, the straps 1142, 1144 wrap circumferentially around a portion of the limb segment (e.g., the leg), to securely couple the orthosis 1050 to the limb segment. In some embodiments, the handle 1150 can form and/or provide a structure that can facilitate the engagement of the coupling portion 1140. For example, the handle 1150 can define an opening shaped to be disposed about the stimulator 1400 (e.g., the housing of the stimulator), when the stimulator is coupled to the frame assembly 1100, as shown in FIGS. 5 and 6, and/or disposed about a portion of the cradle 1130, as shown in FIG. 14. In some embodiments, the handle can facilitate the engagement and/or manipulation of the coupling portion 1140 by a patient who may have impairment in one or both hands. For example, as shown in FIG. 14, a portion 1152 of the handle can be contoured (e.g., between a top portion of the handle and a bottom portion of the handle) such that an opening 1154 is defined between the handle 1150 and the cradle 1130 when the handle 1150 is coupled about the cradle 1130. The opening 1154 is configured to facilitate gripping of the handle 1150 (e.g., by a finger of the user) during coupling and or decoupling of the handle 1150 from about the cradle 1130 and/or the stimulator 1400.

The frame assembly 1100 includes electrode connectors configured to engage a portion of the electrode assembly 1200. The electrode connectors are configured to mechanically couple one or more electrodes to the frame assembly 1100, and to electrically couple one or more electrodes to the electric stimulator 1400, as described herein. In the embodiment shown in FIG. 6, the frame assembly 1100 includes four electrode connectors 1230, 1232, 1234, 1236. As described herein, in some embodiments, two electrodes 1230, 1234 are associated with a first stimulation channel, and two electrodes 1232, 1236 are associated with a second stimulation channel. Each electrode connector 1230, 1232, 1234, 1236 is coupled to, and optionally at least partially disposed within or extended through, an opening 1162, 1164, 1166, 1168, respectively, of the inner layer 1160 of the frame assembly 1100, such that the electrode connectors 1230, 1232, 1234, 1236 are accessible via an inner surface of the frame assembly 1100. The openings 1162, 1164, 1166, 1168 of the inner layer 1160 correspond to openings 1121, 1123, 1125, 1127 defined by the frame 1110 (see, e.g., FIG. 7) when the inner layer 1160 is coupled to the frame 1110, thus at least a portion of the electrode connectors 1230, 1232, 1234, 1236 can be disposed within or extended through the openings 1121, 1123, 1125, 1127 defined by the frame 1110.

In some embodiments, as described herein, at least one electrode connector 1230, 1232, 1234, 1236 is configured to be unused (e.g., not coupled to an electrode) when the electrode assembly 1200 is coupled to the frame assembly 1100. The unused electrode connector(s) 1230, 1232, 1234, 1236 can optionally have one or more connector covers disposed thereon to prevent the inadvertent flow of electrical current therefrom during FES. For example, as shown in FIG. 6A, a connector cover 1270 according to an embodiment is configured to be removably coupled to an unused electrode connector (e.g., electrode connectors 1230, 1232, 1234, 1236). The connector cover 1270 includes an outer layer 1272, an inner layer 1274, an outer snap portion 1276, and an inner snap portion 1278. At least one of the outer layer 1272 of the cover 1270 and the inner layer 1274 of the cover 1270 is formed from a non-conductive material. At least one of the outer layer 1272 of the cover 1270 and the inner layer 1274 of the cover 1270 has a sufficient size and shape to wholly cover at least one of the openings 1162, 1164, 1166, 1168 of the inner layer 1160 of the frame assembly 1100. The outer snap portion 1276 is at least partially disposed between the outer and inner layers 1272, 1274 and includes a protrusion that extends through an opening 1275 of the inner layer 1274. The outer snap portion 1276 is configured to matingly engage the inner snap portion. The inner snap portion 1278 is configured to snap-fit with at least one of the electrode connectors (e.g., electrode connectors 1230, 1232, 1234, 1236). In use, the connector cover 1270 is coupled to an unused connector to prevent the inadvertent flow of electrical current from the unused connector during FES. In other embodiments, however, the connector cover can be differently configured (e.g., to include a single non-conductive layer) and/or be configured to couple to the frame assembly 1100 and/or one or more of the electrode connectors 1230, 1232, 1234, 1236 in a different manner.

Figure 15:
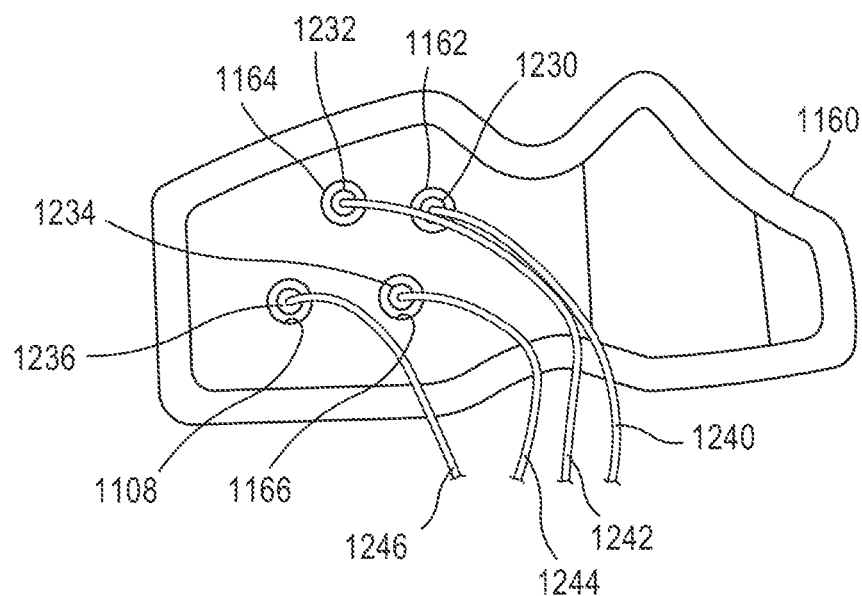
FIG. 15 is a rear view of a portion of a frame assembly of the FES orthosis of FIG. 4, in an uncoupled configuration.

In some embodiments, as shown in FIG. 15, wires 1240, 1242, 1244, 1246 substantially extend between the electrode connectors 1230, 1232, 1234, 1236, respectively, and the electric stimulator 1400 (or one or more connectors of the frame assembly 1100 configured to be electrically coupled to the electric stimulator, such as via the openings 1136, 1137 of the base plate 1134 of the inner portion 1116 of the frame and/or via the set of connectors 1131 of the cradle 1130) and are configured to electrically couple the electric stimulator 1400 to the electrode assembly 1200. More specifically, in some embodiments, wires 1240, 1244 can be configured to electrically couple two electrode connectors 1230, 1234 to the electric stimulator 1400 via a first connector (not shown, e.g., through one of the cradle connector openings), thereby forming at least a portion of a first electrical stimulation channel, and wires 1242, 1246 can be configured to electrically couple the other two electrode connectors 1232, 1236 to the electric stimulator 1400 via a second connector (not shown, e.g., through the other of the cradle connector openings), thereby forming at least a portion of a second electrical stimulation channel. This arrangement facilitates dual-channel functional electrical stimulation by the system 1000, as described in further detail herein.

The electrode connectors 1230, 1232, 1234, 1236 can be any suitable shape, size, or configuration. As shown, the electrode connectors 1230, 1232, 1234, 1236 are in the form of snap connectors. In other embodiments, the electrode connectors can form a button, a detent, a protrusion, one half of a hook-and-loop coupler (i.e., Velcro®), and/or the like. As such, the electrode connectors 1230, 1232, 1234, 1236 can each be matingly placed in contact with a corresponding portion of an electrode included in the electrode assembly 1200 to at least temporarily retain the electrodes in a substantially fixed position relative to the frame assembly 1100. In some embodiments, the position of the electrode connectors 1230, 1232, 1234, 1236, and hence the electrodes coupled thereto, can be associated with a target portion of the neuromuscular system of the leg such as, for example, the peroneal nerve and/or the tibial nerve. Thus, when the electric stimulator 1400 is coupled to the frame assembly 1100, the first and second connectors of the frame assembly 1100 and corresponding connectors of the electrode assembly 1200 electrically couple the electric stimulator 1400 to the electrodes 221 such that at least two channels of electrical current can flow from the electric stimulator 1400 and through the electrodes 221 to provide functional electrical stimulation to the portion of the neuromuscular system of the leg, as described in further detail herein.

Although the frame assembly 1100 is shown and described herein as including an at least semi-rigid frame 1110, in other embodiments, the frame assembly 1100 can be devoid of such a frame 1110. For example, in some embodiments, the frame assembly 1100 can include only the inner layer 1160, only the outer layer 1170, only the inner layer 1160 and the outer layer 1170, or any combination of the inner layer 1160, outer layer 1170 and/or a different soft and/or flexible layer or cuff. For example, in such embodiments, the cradle 1130 can be coupled to and/or supported at least in part by the inner layer 1160, the outer layer 1170, the different soft and/or flexible layer or cuff, or any combination of the foregoing. In another example, in such embodiments, the electric stimulator 1400 is not supported by the frame assembly 1100 of the orthosis 1050, as described herein, but rather can be electronically (and, optionally, mechanically) coupled to the electrodes of the orthosis 1050 by only a cable or wire, or any suitable electrical (and/or mechanical) connection.

As discussed above, the electrode assembly 1200 is removably coupled to the frame assembly 1100. The electrode assembly 1200 can include electrodes in any suitable configuration, and can be substantially similar in form and function to electrode assembly 120 described herein. Each electrode can be engaged by the system 1000, and the electric stimulator 1400 particularly, to promote desired movement of the limb, such as dorsiflexion, plantarflexion, inversion, and/or eversion of the foot. Selective electrode activation and selective flow of electrical current via one or more channels through the neuromuscular system of the limb via the electrodes affects the flow of the electrical current through the portion of the neuromuscular system of the limb to facilitate steering the electrical current therethrough.

Figure 21:
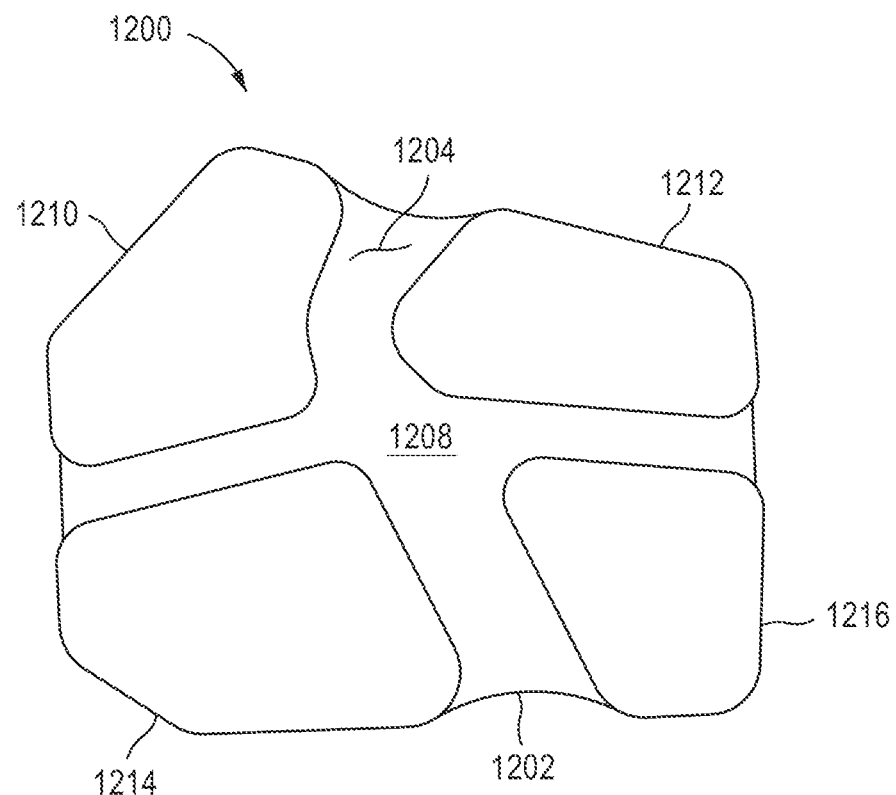
FIGS. 21-24 are front views of an electrode assembly of the FES orthosis of FIG. 4 according to embodiments.

As shown in FIG. 21, the electrode assembly 1200 includes four electrodes or electrode regions (referred to generally herein as "electrodes") 1210, 1212, 1214, 1216. The electrodes 1210, 1212, 1214, 1216 can be formed on, disposed on, or otherwise coupled to a first surface 1204 of a panel 1202. The panel 1202 can be coupled to an inner surface of the frame assembly 1100 (e.g., the inner layer 1160) using any suitable coupling mechanism, such as one or more mechanical fasteners (e.g., snaps, hook-and-loop, or the like), or combination thereof. In the embodiment shown in FIG. 21, the panel 1202 is configured to be coupled to the frame assembly 1100 via complementary male connectors (not shown) extended from a second surface (not shown) of the panel 1202 and configured to be coupled (or snapped) to the connectors 1230, 1232, 1234, 1236 of the frame assembly 1100. In particular, each complementary male connector of the electrode assembly is associated with a respective electrode 1210, 1212, 1214, 1216, thus when the electrode assembly 1200 is coupled to the frame assembly 1100, each electrode 1210, 1212, 1214, 1216 is associated with a respective connector 1230, 1232, 1234, 1236 of the frame assembly 1100, and, optionally, a respective wire 1240, 1242, 1244, 1246 of the frame assembly, and thus forms a portion of one of the first or second electrical stimulation channels (described above). More particularly, two electrodes (e.g., electrodes 1210, 1214) can form a portion of the first stimulation channel, and two electrodes (e.g., electrodes 1212, 1216) can form a portion of the second stimulation channel. The first stimulation channel can be characterized as a medial stimulation channel, and the second stimulation channel can be characterized as a lateral stimulation channel, or vice versa. In this manner, the electrode assembly 1200 is configured for dual-channel function electrical stimulation of a portion of the neuromuscular system of the limb.

The panel 1202 can be constructed of a flexible material to facilitate placement of the electrodes 1210, 1212, 1214, 1216 on the skin of the patient when the orthosis 1050 is donned. In some embodiments, the panel is formed of a non-conductive material. As shown, the panel 1202 includes a non-conductive region 1208 separating each electrode 1210, 1212, 1214, 1216 from the other electrodes. In some embodiments, the panel 1202 includes a conductive layer (e.g., formed of foil, mesh, or the like, or any combination thereof).

The position of each electrode 1210, 1212, 1214, 1216 with respect to the panel 1202 can be fixed. In other words, the electrodes 1210, 1212, 1214, 1216 can be fixedly coupled to the panel 1202, thereby facilitating repeatable placement of the electrodes with respect to the frame assembly 1100 when the electrode assembly 1200 is coupled to the frame assembly. As described herein, current steering is provided by the application of stimulation via multiple channels from the electric stimulator 1400 via the electrode assembly 1200 to the neuromuscular tissue, and thus it is not necessary for the electrodes of the electrode assembly 1200 to be movable to achieve a desired stimulation of the tissue.

The electrodes can be positioned with respect to the panel such that, when the panel is coupled to the frame assembly 1100 and donned on the limb, the electrodes are disposed over or proximate to a target portion of the neuromuscular system of the limb. For example, electrodes 1210, 1212 can each be cathodic electrodes positioned on the panel 1202 such that, in use, the cathodic electrodes provide or facilitate steering of electrical stimulation at least to a target nerve (e.g., the tibial nerve or the peroneal nerve for the lower leg, or the sciatic or femoral nerves for the upper leg or thigh) of the neuromuscular system of the limb. In another example, electrodes 1214, 1216 can each be anodic electrodes positioned on the panel 1202 such that, in use, the anodic electrodes provide or facilitate steering of electrical stimulation at least to a target muscle of the neuromuscular system of the limb. The target muscle can include, for example, the tibialis anterior, extensor hallucis longus, extensor digitorum longus and/or fibularis tertius (e.g., for dorsiflexion). The target muscle can include, for example, the gastrocnemius medial head, gastrocnemius lateral head, soleus, plantaris, tibialis posterior, flexor hallucis longus, flexor digitorum longus, fibularis longus, and/or fibularis brevis (e.g., for plantarflexion).

As shown in FIG. 21, the electrodes 1210, 1212, 1214, 1216 are substantially arranged in each of four quadrants of the panel 1202. In some embodiments, electrodes 1210, 1212 are each cathodic electrodes and electrodes 1214, 1216 are each anodic electrodes, and the electrodes are positioned with respect to the panel 1202 such that the cathodic electrodes are disposed above the anodic electrodes (e.g., each cathodic electrode is vertically disposed over a respective anodic electrode) when the electrode assembly 1200 is coupled to the frame assembly 1100 and the frame assembly is donned on the limb of a standing patient (or such that the cathodic electrodes are disposed between the anodic electrodes and the torso of the patient when the orthosis 1050 is donned). In other embodiments, however, the electrodes, and the distribution of cathodic electrodes and anodic electrodes in particular, can be differently arranged or configured, as described herein.

Figure 22:
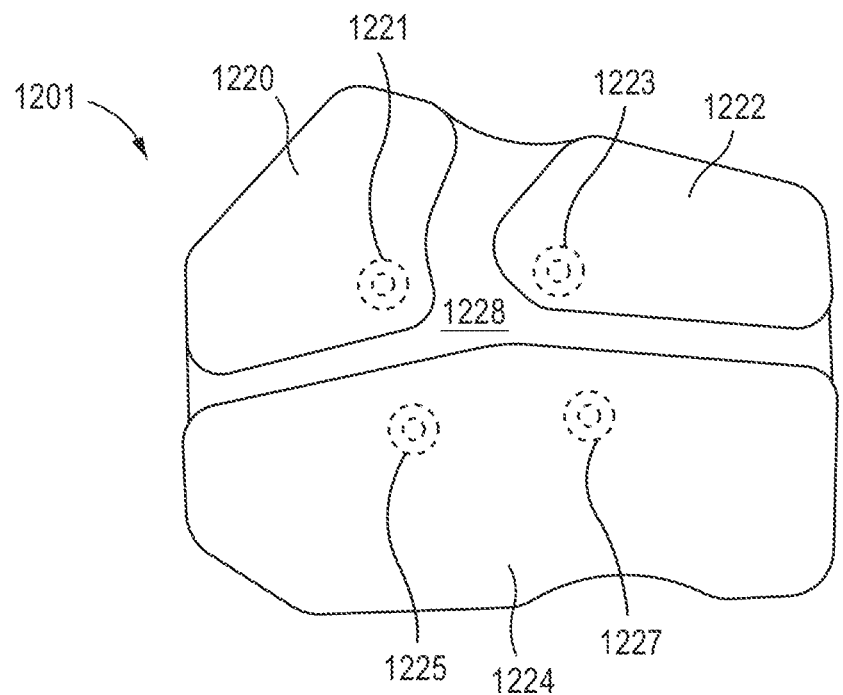

Although the electrode assembly 1200 is shown and described with respect to FIG. 21 as including four electrodes, in some embodiments, the electrode assembly includes a different number of electrodes. For example, as shown in FIG. 22, in some embodiments, an electrode assembly 1201 includes three electrodes (or electrode regions) 1220, 1222, 1224 formed on, disposed on, or otherwise coupled to a panel 1226. The electrode assembly 1201 is configured for use with the frame assembly 1100, and is configured to be coupled to the frame assembly 1100 in a similar manner as described herein with respect to electrode assembly 1200. The electrodes 1220, 1222, 1224 can be arranged with respect to the panel 1226 in any suitable manner, such as that described herein with respect to electrode assembly 1200. The electrode assembly 1201 includes connectors (e.g., male snap-fit connectors) disposed on a side of the panel opposite the electrodes 1220, 1222, 1224 that are configured to couple the electrode assembly to the frame assembly 1110 and to electrically couple the electrodes 1220, 1222, 1224 to the stimulator 1400. For example, a male complementary connector 1221 (shown in dashed lines in FIG. 22) is associated with electrode 1220 and is configured to be coupled to electrode connector 1230 of the frame assembly 1110 and a male complementary connector 1223 (shown in dashed lines in FIG. 22) is associated with electrode 1222 and is configured to be coupled to electrode connector 1232 of the frame assembly 1110. Electrode 1224 can include or be associated with two male complementary connectors 1225, 1227 (shown in dashed lines in FIG. 22) that are configured to be coupled to electrode connectors 1234, 1236, respectively, of the frame assembly 1110. As such, the electrode 1224 can form a part of each of the first and second stimulation channels. In this manner, the electrode 1224 can be "common" to each of the first and second stimulation channels. As shown, the "common" electrode 1224 has a conductive surface area configured to contact the patient's skin that is larger than the conductive surface area of one or more of the other electrodes 1220, 1222. More specifically, as shown, electrode 1224 has a conductive surface area configured to contact the patient's skin that is equal to or greater than the conductive surface areas of the other electrodes 1220, 1222 combined.

More specifically, in some embodiments, two electrodes 1220, 1222 are cathodic electrodes and one electrode 1224 is an anodic electrode. In use, the cathodic electrodes 1220, 1222 are disposed vertically above the anodic electrode 1224, as described above with respect to electrode assembly 1200. The first cathodic electrode 1220 and the anodic electrode 1224 can form a portion of a first stimulation channel, as described above with respect to system 1000. The second cathodic electrode 1222 and the anodic electrode 1224 can form a portion of a second stimulation channel, as described above with respect to system 1000. In this manner, the anodic electrode 1224 can be "common" to each of the first and second stimulation channels. As shown, the anodic electrode 1224 has a conductive surface area that is equal to or greater than the combined conductive surface areas of the cathodic electrodes 1220, 1222.

Figure 23:
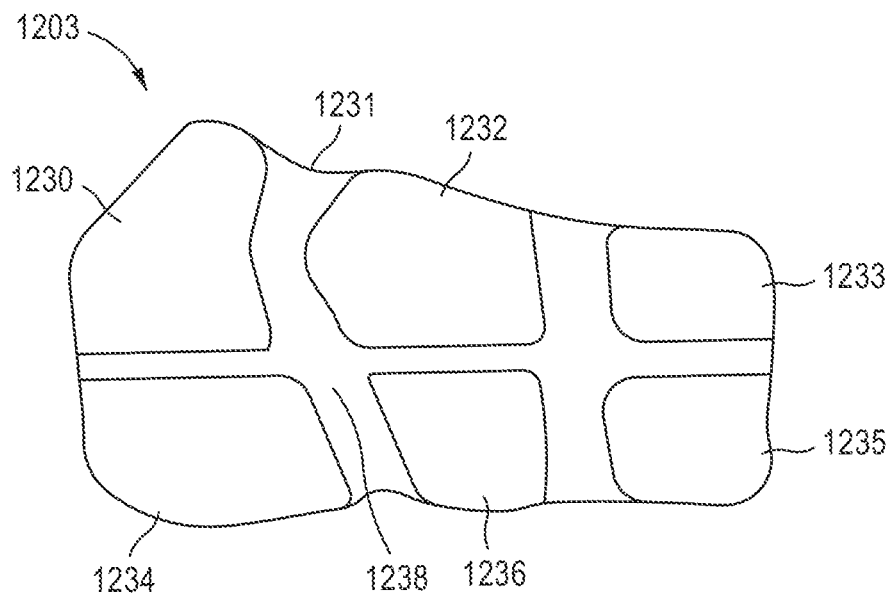

In another example, as shown in FIG. 23, an electrode assembly 1203 according to an embodiment includes a panel 1231 and six electrodes (or electrode regions) 1230, 1232, 1233, 1234, 1236, 1235 arranged thereon. A non-conductive region 1238 of the panel 1231 is disposed between each of the electrodes. Electrodes 1230, 1232 and electrodes 1234, 1236 can be substantially similar in form and/or function to electrodes 1210, 1212 and electrodes 1214, 1216, respectively, and thus are not described in detail here. For example, electrodes 1230, 1232 and electrodes 1234, 1236 can be cathodic electrodes and anodic electrodes, respectively, configured to form a portion of first and second stimulation channels, as described above with respect to electrode assembly 1200. Electrodes 1233, 1235 each are associated with a connector configured to be electrically coupled to the electric stimulator 1400 via a frame assembly (not shown in FIG. 23), substantially similar to frame assembly 1100, that includes corresponding connectors for each electrode (e.g., six connectors in total) on an inner surface thereof. Electrodes 1233, 1235 are configured to form a portion of a third stimulation channel in electrical communication with the electric stimulator 1400 via the frame assembly.

Figure 24:
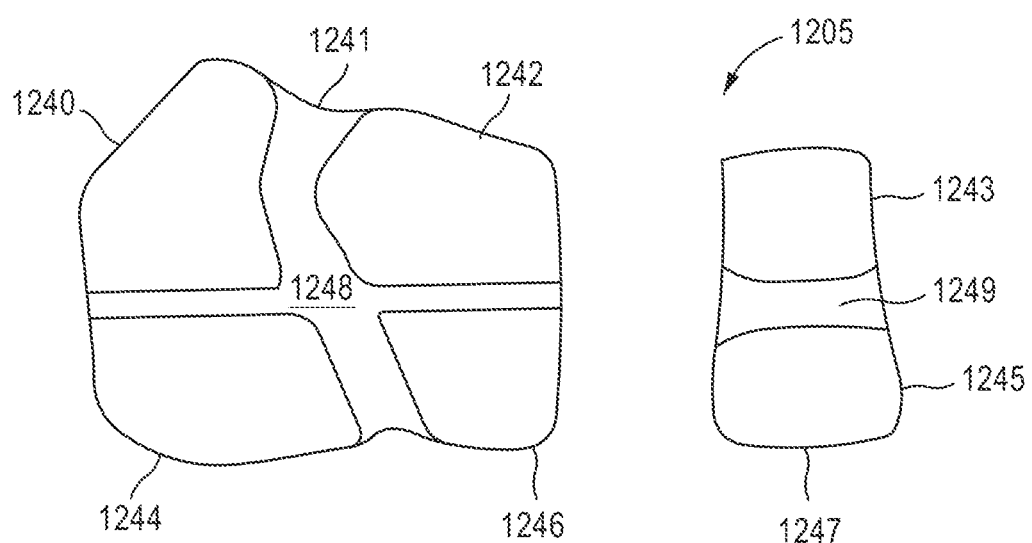

Although the electrode assembly 1203 is shown and described as including six electrodes 1230, 1232, 1233, 1234, 1236, 1235 disposed on a single panel 1231, in another embodiment, an electrode assembly 1205 includes five or six electrodes distributed on two panels. More specifically, in the embodiment shown in FIG. 24, four electrodes (or electrode regions) 1240, 1242, 1244, 1246 are disposed on a first panel 1241 that includes a non-conductive region 1248 between the electrodes. The first panel 1241 and respective electrodes 1240, 1242, 1244, 1246 can be substantially similar to, or identical, in form and function to electrode assembly 1200, and thus are not described in detail herein. In other embodiments, however, the first panel can be substantially similar to the panel of the electrode assembly 1201 shown and described herein with respect to FIG. 22. Referring again to FIG. 24, the electrode assembly can include a second panel 1247 includes two electrodes (or electrode regions) 1243, 1245, which are configured to form a portion of a third stimulation channel in a similar manner as that described above with respect to electrodes 1233, 1235. In some embodiments, the second panel 1247 is configured to be coupled to the frame assembly 1100 such that the second panel 1247 is disposed adjacent a portion of the limb segment that is opposite the portion of the limb segment adjacent the first panel 1241, when the orthosis 1050 is donned.

Although the electrode assembly 1200 is shown and described herein as including the panel 1202 with a plurality of electrodes (e.g., electrodes 1210, 1212, 1214, 1216) fixedly coupled thereto, in some embodiments, the electrode assembly can include one, two, three, four or more electrodes configured to be coupled to the frame assembly 1100 in a different manner. For example, in some embodiments, the electrode assembly 1200 can include one or more conventional electrodes (e.g., a hydrogel electrode, a small cloth electrode, or the like).

Figure 19B:
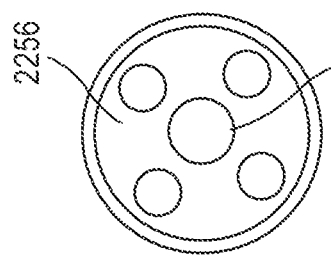
FIGS. 19A-19B are top and bottom views, respectively, of an electrode configured for use with the FES orthosis of FIG. 4 according to an embodiment.
Figure 19D:
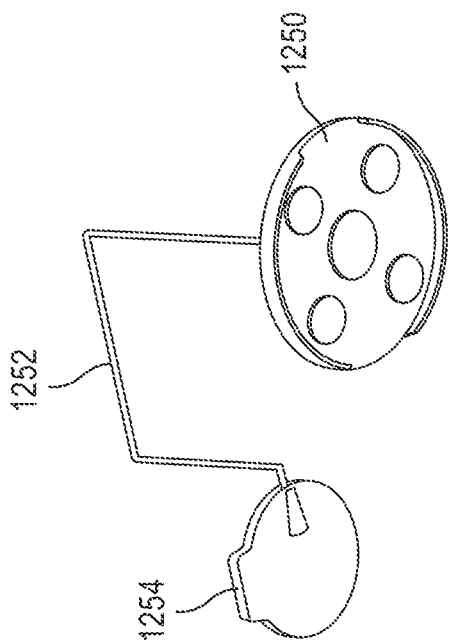
FIGS. 19C-19D are perspective views of an electrode base configured for use with the FES orthosis of FIG. 4 according to an embodiment.
Figure 19A:
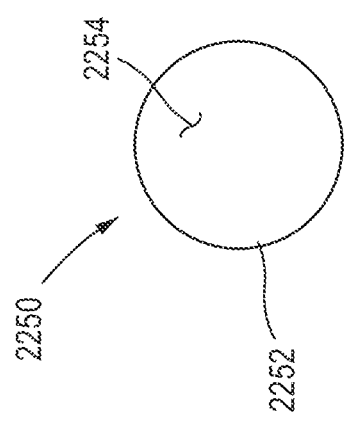

As shown in FIGS. 19A-19B, an electrode assembly 2250 can include a set of gel electrodes 2252, which each electrode of the set having a first side 2254 and a second side 2256 opposite the first side. The first side 2254 of the electrode 2252 includes a gel (e.g., hydrogel) and is configured to be placed in contact with a skin of the patient's limb. The second side 2256 of the electrode 2252 includes a connector 2257 configured to place the electrode in electrical communication with the stimulator 1400. The electrode 2252 can optionally be configured to be in contact with and/or received at least partially by an electrode base, such as electrode base 1250 shown and described herein with respect to FIGS. 19C-19D, to couple the electrode 2262 to the frame assembly 1100. In other embodiments, the electrode 2252 (or electrode assembly 2250) can be coupled to the frame assembly 1100 in a different manner.

In another example, as shown in FIGS. 20A-20B, an electrode assembly 2260 can include a set of cloth electrodes 2262, with each electrode of the set having a first side 2264 and a second side 2266 opposite the first side. The first side 2264 of the electrode 2262 includes a cloth and is configured to be placed in contact with a skin of the patient's limb. In use, the cloth may be wetted before being placed in contact with the patient's skin to facilitate transmission of a stimulation current therethrough. The second side 2266 of the electrode 2262 includes a connector 2267 configured to place the electrode in electrical communication with the stimulator 1400. The electrode 2262 can optionally be configured to be in contact with and/or received at least partially by an electrode base, such as electrode base 1260 shown and described herein with respect to FIGS. 19C-19D, to couple the electrode 2262 to the frame assembly 1100. In other embodiments, the electrode 2262 (or electrode assembly 2260) can be coupled to the frame assembly 1100 in a different manner.

Figure 19C:
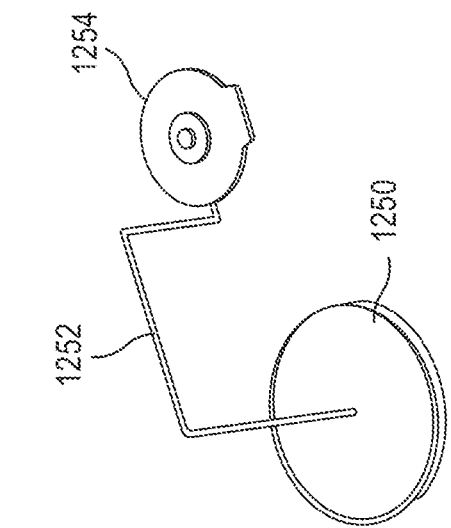

The one or more conventional electrodes can be used with the orthosis 1050 in addition to or instead of the panel 1202 including the plurality of fixedly coupled electrodes 1210, 1212, 1214, 1214. Such one or more conventional electrodes can be coupled to the frame assembly 1100 in any suitable manner. For example, as shown in FIGS. 19C-19D, an electrode assembly according to an embodiment can include an electrode base 1250 coupled via a wire 1252 (or other suitably circuitry) to a snap connector 1254. The snap connector 1254 is configured to mechanically and electrically couple the electrode base 1250 to one of the connectors 1230, 1232, 1234, 1236 of the frame assembly 1100. The wire 1252 between the snap connector 1254 and the electrode base 1250 can be flexible, and thus can permit selective positioning of the base 1250 with respect to the inner layer 1160 of the frame assembly 1100. The electrode base 1250 is configured to be coupled to or otherwise engaged with, for example, a hydrogel electrode.

In another example, as shown in FIGS. 20C-20D, an electrode assembly according to an embodiment can include an electrode base 1260 coupled via a wire 1262 (or other suitably circuitry) to a snap connector 1264. The snap connector 1264 is configured to mechanically and electrically couple the electrode base 1260 to one of the connectors 1230, 1232, 1234, 1236 of the frame assembly 1100. The wire 1262 between the snap connector 1264 and the electrode base 1260 can be flexible, and thus permits selective positioning of the base 1260 with respect to the inner layer 1160 of the frame assembly 1100. As shown in FIG. 20B, at least a portion of the wire 1262 can be disposed within the electrode base 1260. The electrode base 1260 is configured to be coupled to or otherwise engaged with, for example, a soft cloth electrode.

Although the electrode assemblies (e.g., electrode assembly 1200) have been shown and described herein as including a panel (e.g., panel 1202) with a plurality of electrodes (e.g., electrodes 1210, 1212, 1214, 1216) fixedly coupled thereto, in some embodiments, one or more electrodes can be removably couplable to the panel. For example, the electrode(s) can be coupled to the panel via a hook and loop fastener, a removable adhesive, or the like. The electrode assembly can include a flexible wire or other suitable flexible electrical extension with one end attached to the electrode and the opposite end electrically coupled to the connector via the panel. The flexible wire is configured to permit a range of movement of the electrode with respect to the panel. In this manner, the electrode can be selectively positioned on the side of the panel facing the limb segment in one of multiple different positions.

Although the electrode assembly 1200, and electrodes more generally, have been shown and described herein as being removably coupled to an inner surface of the frame assembly 1100, in some embodiments, at least one of the electrode assembly 1200 or an electrode is disposed on or otherwise coupled to the patient's body independently of the frame assembly 1100. For example, in some embodiments, one, two, three, four or more electrodes, which can be coupled to the electric stimulator 1400 via a cable or wire, are coupled directly to the patient's body (e.g., skin) without the use of the frame assembly 1100. Such electrodes and electric stimulator 1400 can be collectively configured to apply stimulation in any suitable manner, including any one or more of the stimulation patterns described herein.

The electric stimulator 1400 of the orthosis 1050 is configured to apply functional electrical stimulation to the patient's body, and can include any suitable combination of hardware and software. The electric stimulator 1400 can be substantially similar in form and/or function to the electric stimulator 140 described herein. For example, the electric stimulator 140 can be an electronic device that includes one or more electrical circuits operable in providing a flow of electrical current to at least a portion of the neuromuscular system of the limb. More specifically, the electric stimulator 1400 is configured to provide the flow of electrical current via multiple channels to one or more portions of the neuromuscular system of the limb, as described herein. For example, the electric stimulator 1400 can be configured or programmed to provide multi-channel electrical stimulation, such as dual-channel or three channel FES. Said another way, the electric stimulator 1400 is selectively operable to provide a flow of electrical current to at least a portion of the neuromuscular system of the limb via the electrode assembly using two channels (or stimulation channels) or three channels. In some embodiments, the stimulator 1400 includes a dedicated contact or connector configured to electrically interface with the orthosis 1050 for each stimulation channel.

The electric stimulator 1400 can include, for example, at least a memory, a processor, and a power source disposed within a housing of the stimulator. The electric stimulator 1400 of the orthosis 1050 can be removably coupled to the cradle 1130 of the frame assembly 1100. The cradle 1130 is configured to at least temporarily retain the electric stimulator 1400 therein, as described herein. In this manner, the electric stimulator 1400 (e.g., the housing of the electric stimulator) can be mounted to and supported by the frame assembly 1100.

The electric stimulator 1400 is configured to be placed in electrical communication with the electrode assembly 1200 (or, optionally, another electrode assembly described herein, including, but not limited to, electrode assembly 1201), for example, when the electric stimulator 1400 is removably coupled to the assembled frame assembly 1100. The electric stimulator 1400 includes at least one electrical contact or connector configured to electrically couple the electric stimulator 1400 to at least one connector (or electrode connector) of the frame assembly 1100. More specifically, the electric stimulator 1400 can include a first connector and a second connector (not shown) configured to be electrically coupled to corresponding connectors (not shown) of the frame assembly, such as via openings 1136, 1137 of the base plate 1134 of the inner portion 1116 of the frame and/or via the set of connectors 1131 of the cradle 1130. In this manner, the electric stimulator 1400 can be configured for dual-channel stimulation of a portion of the neuromuscular system of the limb of the patient. The first and second connector of the electric stimulator 1400 can include any suitable wiring, connector, contact, interface, and/or structure.

In some embodiments, a first set of components of the orthosis 1050 is configured to provide FES via a first channel. The first set of components can include, for example, the electric stimulator 1400, electrodes 1210, 1214, and one or more connectors, wiring, other circuitry, or the like therebetween. In use, the electric stimulator 1400 sends a first signal according to a first set of parameters to electrode 1210 (e.g., a cathodic electrode), resulting in the electrode 1210 providing an electric current according to the first set of parameters to a portion of neuromuscular system of the limb and to electrode 1214 (e.g., an anodic electrode) via the tissue, thereby defining a first stimulation channel.

A second set of components of the orthosis 1050 can be configured to provide FES via a second channel. The second set of components can include, for example, the electric stimulator 1400, electrodes 1212, 1216, and one or more connectors, wiring, other circuitry, or the like therebetween. In use, the electric stimulator 1400 sends a second signal according to a second set of parameters to electrode 1212 (e.g., a cathodic electrode), resulting in the electrode 1212 providing an electric current according to the second set of parameters to a portion of neuromuscular system of the limb, and at least a portion of the electrical current being received from the tissue by the electrode 1216 (e.g., an anodic electrode), thereby defining a second stimulation channel. In such an embodiment, the system 1000 can be configured to provide monopolar stimulation to the limb substantially concurrently during a time period via the first channel and the second channel.

Figure 25:
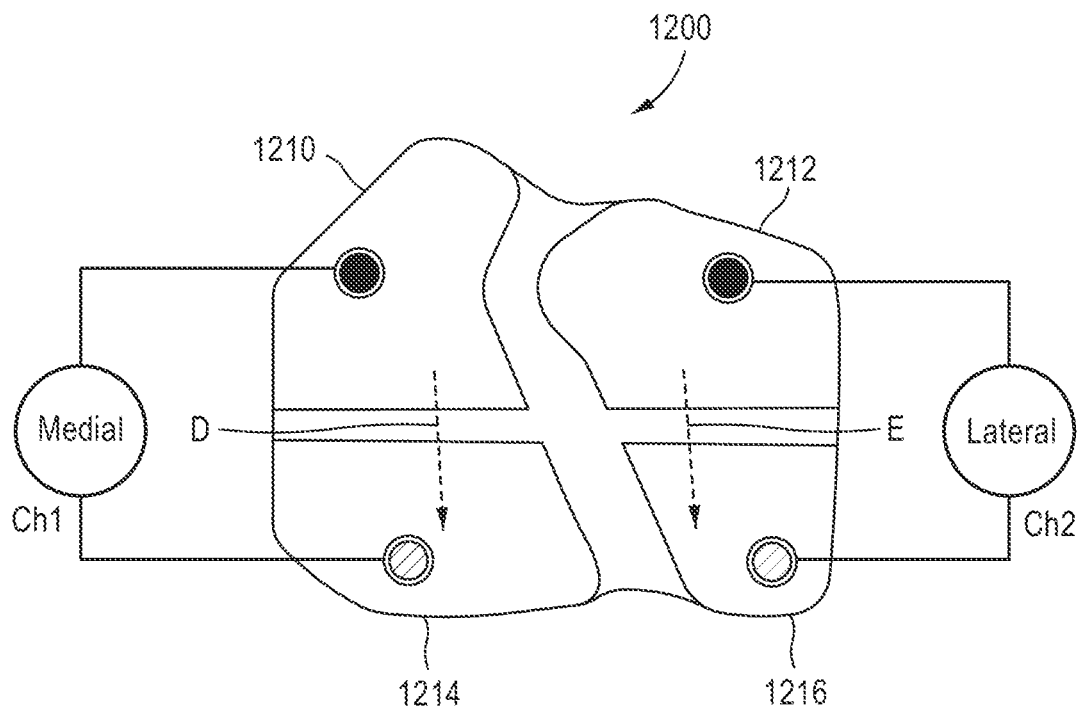
FIGS. 25-44 are schematic illustrations of electrical stimulation channels formed, in part, by providing electrical stimulation from an electric stimulator of the FES orthosis of FIG. 4 to an electrode assembly according to embodiments.

The electric stimulator 1400 can selectively and/or independently control one or more parameters associated with the flow of electrical current via each channel. Such parameters can include, but are not limited to, the electrical current's amplitude, voltage, pulse rate, waveform, or the like, which can collectively define the electrical current's intensity, and whether the flow of electrical current is on or off. For example, during a time period, the electric stimulator 1400 can provide a flow of electrical current having a first intensity via a first channel (e.g., Ch1, as shown in FIG. 25, et seq.) and a flow of electrical current having a second intensity via a second channel (e.g., Ch2, as shown in FIG. 25, et seq.), such that the current flows via the first channel substantially concurrently with the flow of the current via the second channel. The second intensity can be less than, substantially equal to, or greater than the first intensity. In some embodiments, the first intensity is greater than the second intensity.

In some embodiments, the electrical current provided via the first channel has an amplitude different from an amplitude of the electrical current provided via the second channel. The electrical current provided via at least one of the first channel or the second channel can have an amplitude within the range of about 10 milliamperes (mA) to about 50 mA. For example, in some embodiments, the amplitude of the electrical current for the first channel is within the range of about 10 mA to about 50 mA, and the amplitude of the electrical current for the second channel is within the range of about 10 mA to about 30 mA. More specifically, in some embodiments, the amplitude of the electrical current associated with the first channel can be about 30 mA and the amplitude of the electrical current associated with the second channel can be about 25 mA. It should be noted that by using dual-channel stimulation, similar or improved foot movement can be promoted utilizing lower intensities, including lower current amplitudes, than that resulting from stimulation at a higher intensity using a known FES system.

In some embodiments, the electrical current provided via at least one of the first channel or the second channel has a pulse rate within the range of 10 hertz ("Hz") to 60 Hz. For example, in one embodiment, the pulse rate of the current provided by both the first channel and the second channel is 30 Hz. In another example, in one embodiment, the pulse rate of the current provided by both the first channel and the second channel is 40 Hz. In some embodiments, the electrical current provided via at least one of the first channel or the second channel has a symmetric waveform, however, in other embodiments the current can produce a different waveform, such as an asymmetric waveform or a sine waveform. In some embodiments, the electrical current provided via at least one of the first channel or the second channel has a phase duration within the range of 50 microseconds (µs) to 300 µs. For example, in one embodiment, the phase duration of the current provided by both the first channel and the second channel is 200 µs.

In this manner, the electric stimulator 1400 can cause electrical current to flow through each of the two channels substantially during a time period, while the electric stimulator 1400 controls the parameters of the electrical current flowing through each channel independently of one or more parameters of the current flowing through another channel. By independently controlling the flow of electrical current through each channel, the electric stimulator 1400, and the orthosis 1050 as a whole, is configured to steer the electrical current within the neuromuscular system of the limb, thereby promoting improved movement and positioning of a portion of the limb 10 (e.g., the foot) during a gait event, over that which would otherwise be caused using known FES systems utilizing single channel stimulation. For example, the multi-channel FES systems described herein promote better balanced dorsiflexion and/or better balanced plantarflexion that that resulting from the use of known FES systems.

The electric stimulator 1400 can be programmed to provide multiple stimulation configurations or patterns utilizing the orthosis 1050, including any stimulation parameters described herein. For example, referring to FIG. 25, in one embodiment, the system 1000 is configured for stimulation of at least a portion of a neuromuscular system of a limb (e.g., a leg) via a first channel Ch1 and a second channel Ch2. The first channel Ch1 is formed, at least in part, by a first cathodic electrode 1210 and a first anodic electrode 1214 of the electrode assembly 1200, as well as the stimulator 1400 and circuitry and/or connectors (e.g., electrode connectors 1230, 1234) therebetween. The second channel Ch2 is formed, at least in part, by a second cathodic electrode 1212 and a second anodic electrode 1216, as well as the stimulator 1400 and circuitry and/or connectors (e.g., electrode connectors 1232, 1236) therebetween. In some embodiments, such as when the orthosis 1050 is donned on the right leg of the patient or another limb on the right half of the patient's body, the first channel Ch1 can be considered a medial (stimulation) channel and the second channel Ch2 can be considered a lateral (stimulation) channel.

The electric stimulator 1400 is configured to provide stimulation during a time period via the first channel Ch1 such that an electrical current flows from at least one of the first cathodic electrode 1210 and the first anodic electrode 1214 into the neuromuscular system of the limb and through a portion of the neuromuscular system of the limb between the first cathodic electrode 1210 and the first anodic electrode 1214. More specifically, the electric stimulator 1400 can be configured to provide stimulation via the first channel Ch1 such that the electrical current flows from the first cathodic electrode 1210 through the neuromuscular system to the first anodic electrode 1214. In some embodiments, the stimulation is bipolar. In some embodiments, the stimulation is monopolar. The electric stimulator 1400 is configured to provide stimulation via the second channel Ch2 such that an electrical current flows from at least one of the second cathodic electrode 1212 and the second anodic electrode 1216 into the neuromuscular system of the limb and through a portion of the neuromuscular system of the limb between the second cathodic electrode 1212 and the second anodic electrode 1216. In some embodiments, the stimulation is bipolar. In other embodiments, the stimulation is monopolar. In this manner, the system 100 can be configured to provide parallel stimulation channels through the neuromuscular system, as represented by arrows D and E in FIG. 25. In some embodiments, the stimulation is provided via the first channel Ch1 during a first time period, and the stimulation is provided via the second channel Ch2 substantially concurrently during the first time period. In other embodiments, the stimulation is provided via the first channel Ch1 during the first time period, and the stimulation is provided via the second channel Ch2 during a second time period different than the first time period (e.g., during an earlier time period or a subsequent time period, or during alternating time periods).

Figure 26:
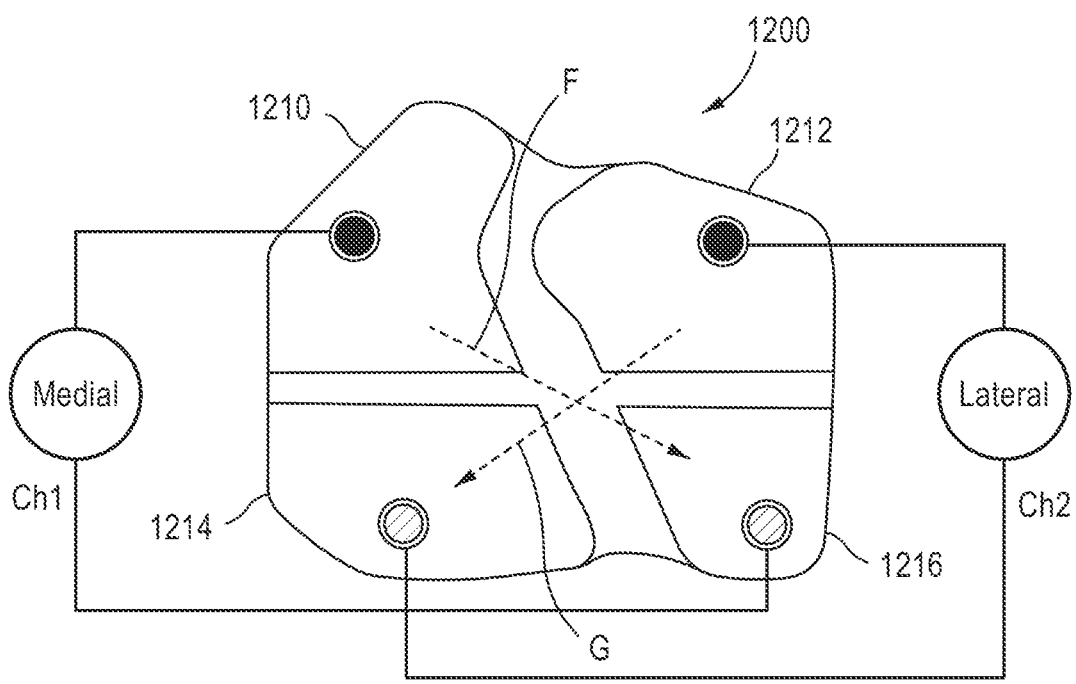

In another example, referring to FIG. 26, in one embodiment, the system 1000 is configured for stimulation of at least a portion of a neuromuscular system of a limb (e.g., a leg) via a first channel Ch1 and a second channel Ch2. The first channel Ch1 is formed, at least in part, by the first cathodic electrode 1210 and the second anodic electrode 1216 of the electrode assembly 1200, as well as the stimulator 1400 and circuitry and/or connectors therebetween. The second channel Ch2 is formed, at least in part, by the second cathodic electrode 1212 and the first anodic electrode 1214, as well as the stimulator 1400 and circuitry and/or connectors therebetween. In some embodiments, such as when the orthosis 1050 is donned on the right leg of the patient or another limb on the right half of the patient's body, the first channel Ch1 can be considered a medial (stimulation) channel and the second channel Ch2 can be considered a lateral (stimulation) channel.

The electric stimulator 1400 is configured to provide stimulation during a time period via the first channel Ch1 such that an electrical current flows from at least one of the first cathodic electrode 1210 and the second anodic electrode 1216 into the neuromuscular system of the limb and through a portion of the neuromuscular system of the limb between the first cathodic electrode 1210 and the second anodic electrode 1216. More specifically, the electric stimulator 1400 can be configured to provide the stimulation via the first channel Ch1 such that the electrical current flows from the first cathodic electrode 1210 to the second anodic electrode 1216 via the neuromuscular system of the limb. In some embodiments, the stimulation is bipolar. In other embodiments, the stimulation is monopolar.

The electric stimulator 1400 is configured to provide stimulation via the second channel Ch2 such that an electrical current flows from at least one of the second cathodic electrode 1212 and the first anodic electrode 1214 into the neuromuscular system of the limb and through a portion of the neuromuscular system of the limb between the second cathodic electrode 1212 and the first anodic electrode 1214. More specifically, the electric stimulator 1400 can be configured to provide the stimulation via the second channel Ch2 such that the electrical current flows from the second cathodic electrode 1212 to the first anodic electrode 1214 via the neuromuscular system of the limb. In some embodiments, the stimulation is bipolar. In other embodiments, the stimulation is monopolar. In this manner, the system 100 can be considered to be configured to provide diagonal stimulation channels through the neuromuscular system, as represented by arrows F and G in FIG. 26. In some embodiments, the stimulation is provided via the first channel Ch1 during a first time period, and the stimulation is provided via the second channel Ch2 substantially concurrently during the first time period. In other embodiments, the stimulation is provided via the first channel Ch1 during the first time period, and the stimulation is provided via the second channel Ch2 during a second time period different than the first time period (e.g., during an earlier time period or a subsequent time period, or during alternating time periods). To implement such a stimulation configuration, in some embodiments, the connection of wires 1244, 1246 to the electrode connectors 1234, 1236, respectively, may be re-routed or reversed, or the connection of wires 1244, 1246 to the connector or contact of the stimulator may be re-routed or reversed.

Figure 27:
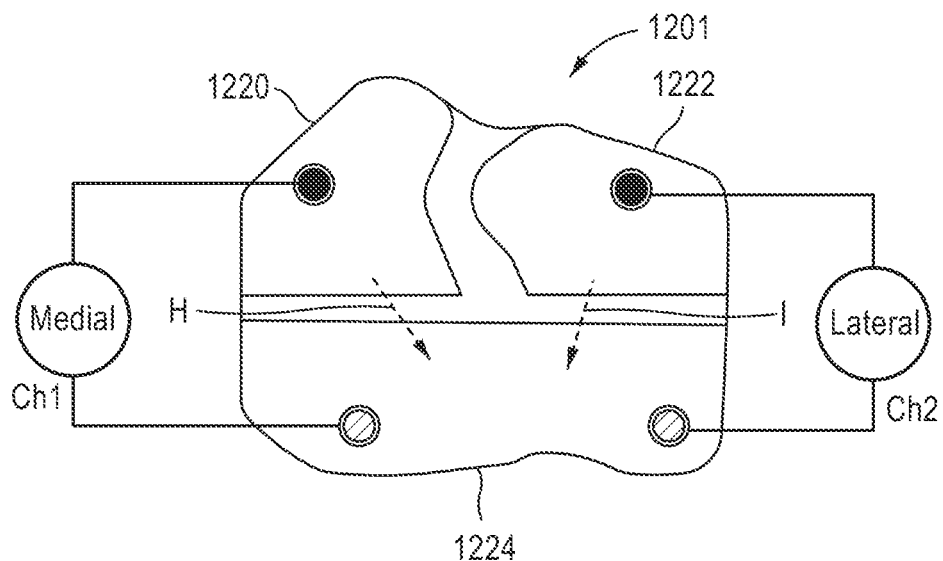

In another example, referring to FIG. 27, in one embodiment, the system 1000 is configured for stimulation of at least a portion of a neuromuscular system of a limb (e.g., a leg) via a first channel Ch1 and a second channel Ch2. The first channel Ch1 is formed, at least in part, by the first cathodic electrode 1220, which is coupled to the first electrode connector 1230 of the frame assembly 1100, and the anodic electrode 1224, via the third electrode connector 1234 which is coupled to the anodic electrode 1224, of the electrode assembly 1201, as well as the stimulator 1400 and circuitry and/or additional connectors therebetween. The second channel Ch2 is formed, at least in part, by the second cathodic electrode 1222, which is coupled to the second electrode connector 1232 of the frame assembly 1100, and the anodic electrode 1224, via the fourth electrode connector 1236 which is coupled to the anodic electrode 1224, as well as the stimulator 1400 and circuitry and/or additional connectors therebetween. In some embodiments, such as when the orthosis 1050 is donned on the right leg of the patient or another limb on the right half of the patient's body, the first channel Ch1 can be considered a medial (stimulation) channel and the second channel Ch2 can be considered a lateral (stimulation) channel.

The electric stimulator 1400 is configured to provide stimulation during a time period via the first channel Ch1 such that an electrical current flows from the first cathodic electrode 1220 into the neuromuscular system of the limb and through a portion of the neuromuscular system of the limb between the first cathodic electrode 1220 and the anodic electrode 1224. In some embodiments, at least a portion of the electrical current flowing via the first channel Ch1 is returned to the electric stimulator 1400 via the anodic electrode 1224 and one or more of connectors 1234, 1236. In some embodiments, the stimulation is monopolar. In other embodiments, the stimulation is bipolar. The electric stimulator 1400 is configured to provide stimulation via the second channel Ch2 such that an electrical current flows from the second cathodic electrode 1222 into the neuromuscular system of the limb and through a portion of the neuromuscular system of the limb between the second cathodic electrode 1222 and the anodic electrode 1224. In some embodiments, at least a portion of the electrical current flowing via the second channel Ch2 is returned to the electric stimulator 1400 via the anodic electrode 1224 and one or more of connectors 1234, 1236. In some embodiments, the stimulation is provided via the first channel Ch1 during a first time period, and the stimulation is provided via the second channel Ch2 substantially concurrently during the first time period. In other embodiments, the stimulation is provided via the first channel Ch1 during the first time period, and the stimulation is provided via the second channel Ch2 during a second time period different than the first time period (e.g., during an earlier time period or a subsequent time period, or during alternating time periods). In some embodiments, the stimulation is monopolar. In other embodiments, the stimulation is bipolar.

In this manner, the system 100 can be considered to be configured to provide two stimulation channels through the neuromuscular system of the limb using a common anode, with a current flow through the tissue generally represented by arrows H and I in FIG. 27. An FES system implementing one or more common anode configurations, as described herein, for providing FES to neuromuscular system can provide a greater disbursement of the flow of electrical current through the neuromuscular tissue than that provided by a single-channel stimulation system. Additionally, because one or more parameters of the current flow, and thus the current's intensity, along each channel (i.e., the first channel Ch1 and the second channel Ch2) are independently programmed to or selected by the stimulator, the disbursement of the electrical current through the neuromuscular system can be targeted or otherwise manipulated by controlling the one or more parameters (e.g., by increasing or decreasing a current's amplitude), thereby promoting a desired response by the neuromuscular system, such as dorsiflexion, plantarflexion, inversion or eversion of the foot.

Figure 28:
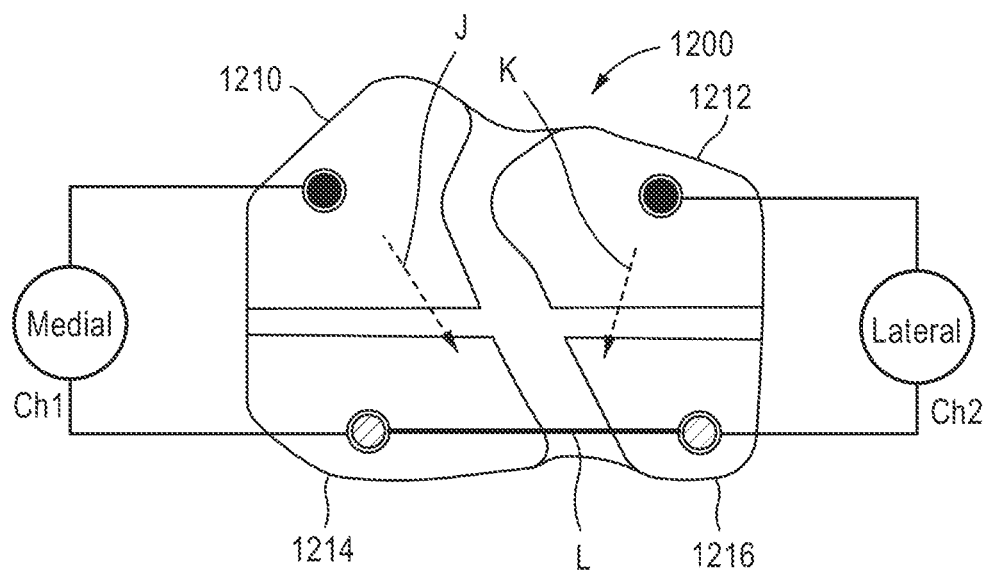

In still another example, referring to FIG. 28, in one embodiment, the system 1000 is configured for stimulation of at least a portion of a neuromuscular system of a limb (e.g., a leg) via a first channel Ch1 and a second channel Ch2. The first channel Ch1 is formed, at least in part, by the first cathodic electrode 1210 and the first anodic electrode 1214 of the electrode assembly 1200, as well as the stimulator 1400 and circuitry and/or connectors therebetween. The second channel Ch2 is formed, at least in part, by a second cathodic electrode 1212 and a second anodic electrode 1216, as well as the stimulator 1400 and circuitry and/or connectors therebetween. In some embodiments, such as when the orthosis 1050 is donned on the right leg of the patient or another limb on the right half of the patient's body, the first channel Ch1 can be considered a medial (stimulation) channel and the second channel Ch2 can be considered a lateral (stimulation) channel, and the electrodes associated with the channels Ch1, Ch2 can be considered medial and lateral electrodes, respectively.

The electric stimulator 1400 is configured to provide stimulation during a time period via the first channel Ch1 such that an electrical current flows from the first cathodic electrode 1210 into the neuromuscular system of the limb and through a portion of the neuromuscular system of the limb between the first cathodic electrode 1210 and at least one of or both the first and second anodic electrodes 1214, 1216, as represented by arrow J in FIG. 28. The electric stimulator 1400 is configured to provide stimulation via the second channel Ch2 such that an electrical current flows from the second cathodic electrode 1212 into the neuromuscular system of the limb and through a portion of the neuromuscular system of the limb between the first cathodic electrode 1210 and at least one of or both the first and second anodic electrodes 1214, 1216, as represented by arrow K in FIG. 28. At least a portion of the current flowing via the first channel Ch1 can be returned (or flow) from the tissue to the stimulator 1400 via the first anodic electrode 1214 and/or the second anodic electrode 1216, and at least a portion of the current flowing via the second channel Ch2 can be returned (or flow) from the tissue to the stimulator 1400 via the first anodic electrode 1214 and/or the second anodic electrode 1216. In this manner, the first and second anodic electrodes are collectively operable as a common anodic electrode. In some embodiments, the stimulation is provided via the first channel Ch1 during a first time period, and the stimulation is provided via the second channel Ch2 substantially concurrently during the first time period. In other embodiments, the stimulation is provided via the first channel Ch1 during the first time period, and the stimulation is provided via the second channel Ch2 during a second time period different than the first time period (e.g., during an earlier time period or a subsequent time period, or during alternating time periods). In some embodiments, to achieve operation of the first and second anodic electrodes 1214, 1216 as a common anodic electrode, and electrical short is included between the first anodic electrode 1214 and the second anodic electrode 1216, as represented by line L in FIG. 28. In such an embodiment, the electric stimulator 1400 can be configured to provide monopolar stimulation.

In yet another example, referring to FIG. 29 and FIGS. 39-44, in one embodiment, the system 1000 is configured for selectively controlled stimulation of at least a portion of a neuromuscular system of a limb (e.g., a leg) via a first channel Ch1 and a second channel Ch2. The first channel Ch1 is formed, at least in part, by the first cathodic electrode 1210, the first anodic electrode 1214, and the second anodic electrode 1216 of the electrode assembly 1200, as well as the stimulator 1400 and circuitry and/or connectors therebetween. The second channel Ch2 is formed, at least in part, by a second cathodic electrode 1212, the first anodic electrode 1214, and the second anodic electrode 1216, as well as the stimulator 1400 and circuitry and/or connectors therebetween. In some embodiments, such as when the orthosis 1050 is donned on the right leg of the patient or another limb on the right half of the patient's body, the first channel Ch1 can be considered a medial (stimulation) channel and the second channel Ch2 can be considered a lateral (stimulation) channel, and the electrodes associated with the channels Ch1, Ch2 can be considered medial and lateral electrodes, respectively.

Figure 29:
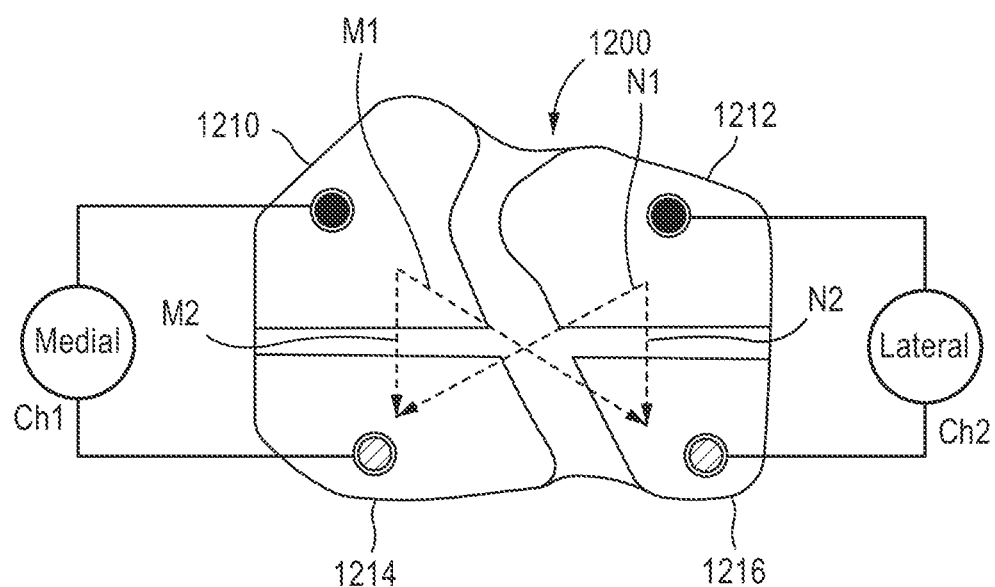
Figure 39:
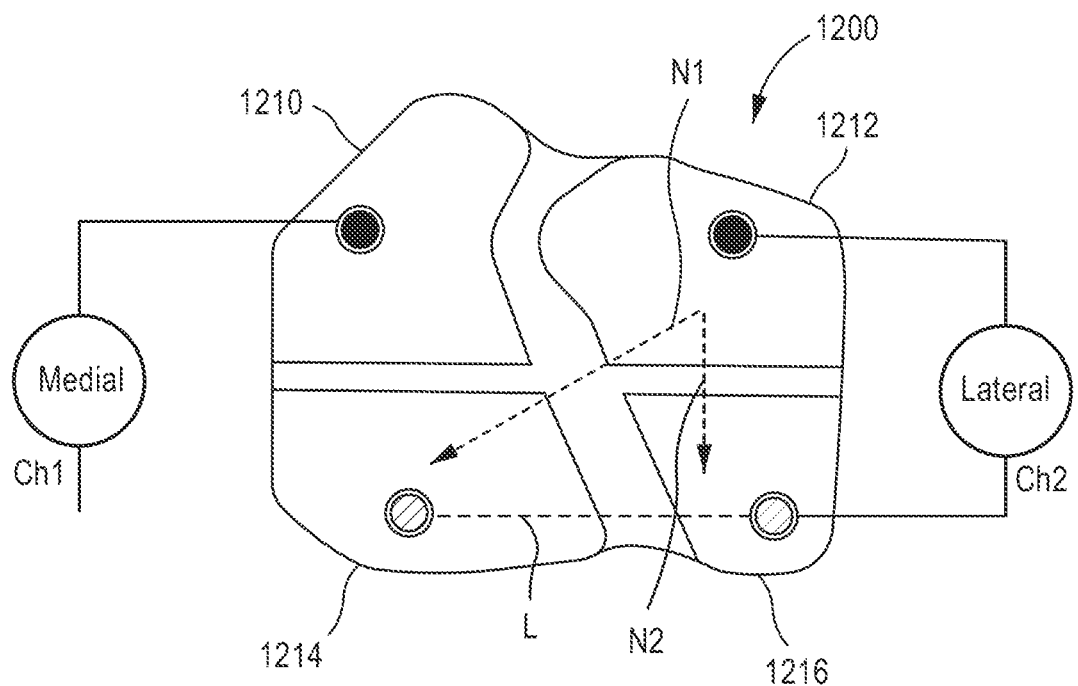

The electric stimulator 1400 is configured to provide stimulation during a first time period via the second channel Ch2 such that an electrical current flows from the second cathodic electrode 1212 into the neuromuscular system of the limb and through a portion of the neuromuscular system of the limb between the second cathodic electrode 1212 and each of the first and second anodic electrodes 1214, 1216, as represented by arrows N1 and N2 in FIGS. 29 and 39. More particularly, as better shown in FIG. 39, during the first time period, the electric stimulator 1400 sends a first stimulation signal to the to the second (or lateral) cathodic electrode 1212 causing the second cathodic electrode 1212 to provide an electrical current (or stimulation) to a portion of the neuromuscular system of the limb and to the first (or medial) anodic electrode 1214 and the second (or lateral) anodic electrode 1216. The first stimulation signal causes the second cathodic electrode 1212 to provide an electrical current having a first set of parameters. At least a portion of the electrical current provided by the second cathodic electrode 1212 can be returned to the stimulator 1400 via the first anodic electrode 1214 and the second anodic electrode 1216.

In this manner, the electric stimulator 1400 is configured (or programmed) to provide, a first stimulation to the portion of the neuromuscular system of the limb via the second channel Ch2, which is formed at least during the first time period, in part, by both anodic electrodes 1214, 1216 of the electrode assembly 1200. The first channel Ch1 can be open (or incomplete or non-functional) during the first time period, as shown in FIG. 39.

Figure 40:
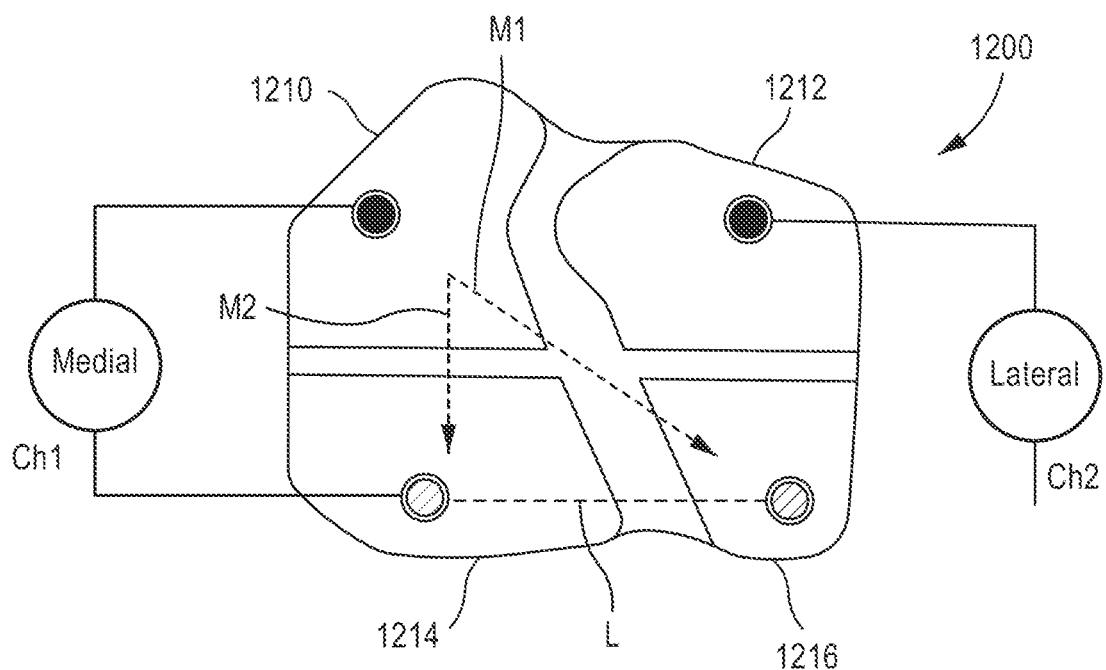

The electric stimulator 1400 is configured to provide stimulation during a second time period, after the first time period, via the first channel Ch1 such that an electrical current flows from the first cathodic electrode 1210 into the neuromuscular system of the limb and through a portion of the neuromuscular system of the limb between the first cathodic electrode 1210 and each of the first and second anodic electrodes 1214, 1216, as represented by arrows M1 and M2 in FIGS. 29 and 40. More particularly, as better shown in FIG. 40, during the second time period, the electric stimulator 1400 sends a second stimulation signal to the to the first (or medial) cathodic electrode 1210 causing the first cathodic electrode 1210 to provide an electrical current (or stimulation) to a portion of the neuromuscular system of the limb and to the first (or medial) anodic electrode 1214 and the second (or lateral) anodic electrode 1216 via the neuromuscular system of the limb. The second stimulation signal causes the first cathodic electrode 1210 to provide an electrical current having a second set of parameters, which can be different from the first set of parameters of the electrical current provided by the second cathodic electrode 1212 during the first time period. At least a portion of the electrical current provided by the first cathodic electrode 1210 can be returned to the stimulator 1400 via the first anodic electrode 1214 and/or the second anodic electrode 1216. In this manner, the electric stimulator 1400 is configured (or programmed) to provide and return, a second stimulation to the portion of the neuromuscular system of the limb via the first channel Ch1, which is formed at least during the second time period, in part, by both anodic electrodes 1214, 1216 of the electrode assembly 1200. The second channel Ch2 can be open (or incomplete or non-functional) during the second time period, as shown in FIG. 40.

The first time period and the second time period can occur substantially during a gait event, such as a "heel-off" event or a "heel-on" event. In some embodiments, the system includes a sensor (e.g., sensor 130) configured to detect the gait event. The sensor can be configured to send a signal to the electric stimulator 1400 when the gait event is detected. The electric stimulator 1400 can be configured to send at least one of the first signal or the second signal in response to the signal received from the sensor.

The electrical current having the first set of parameters and the electrical current having the second set of parameters are collectively configured to produce a desired movement or position of the foot during the gait event. Said another way, each of the first set of parameters and the second set of parameters is selected to produce a desired response of the neuromuscular system of the limb to the electrical currents having such parameters. For example, the first set of parameters can include a first electrical current intensity and the second set of parameters can include a second electrical current intensity, different from the first intensity, configured to produce a dorsiflexion, plantarflexion, eversion and/or inversion of the foot. At least one of the stimulation signals via the first channel Ch1 and/or the second channel Ch2 can be monopolar.

In the embodiment shown in FIGS. 29 and 39-40, the first and second anodic electrodes are collectively operable as a common anodic electrode. In some embodiments, an electrical short L can be provided between the first anodic electrode 1214 and the second anodic electrode 1216 to facilitate their collective operability as a common anode, as described herein with respect to FIG. 28. In such an embodiment, the electric stimulator 1400 can be configured to provide monopolar stimulation.

Another stimulation sequence according to an embodiment utilizing the FES system 1000 described herein to provide FES using a segmented electrode assembly described herein (e.g., electrode assembly 1200) such that the first (or medial) anodic electrode 1214 and the second (or lateral) anodic electrode 1216 substantially operate as a common anodic electrode (e.g., as shown in FIG. 29) is shown in FIGS. 41-44. The electric stimulator 1400 is configured (or programmed) to provide a sequence of stimulation signals (e.g., monopolar stimulation) to the electrode assembly. The electric stimulator can be configured to send one or more of the stimulation signals in response to a signal received from a sensor, as described above.

Figure 41:
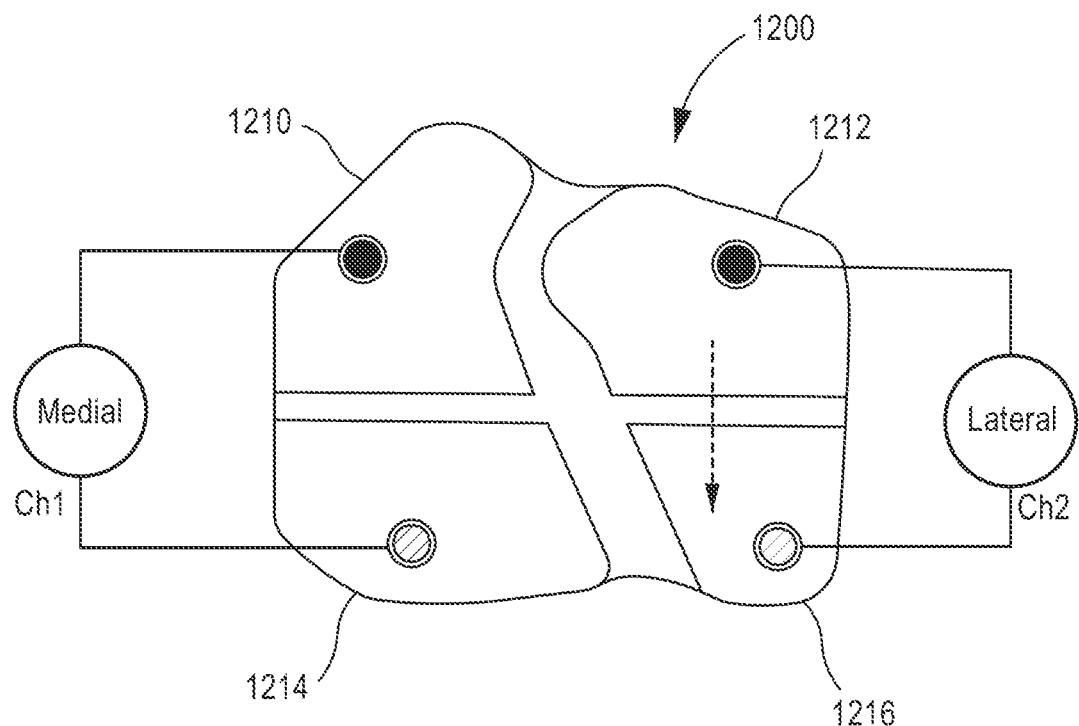

As shown in FIG. 41, during a first time period, the electric stimulator 1400 sends a first stimulation signal to the second cathodic electrode 1212 to cause the second cathodic electrode 1212 to provide an electrical current to the second anodic electrode 1216, which forms a portion of the second channel Ch2 at least during the first time period, through a portion of the neuromuscular system of the limb between the second cathodic electrode 1212 and the second anodic electrode 1216.

Figure 42:
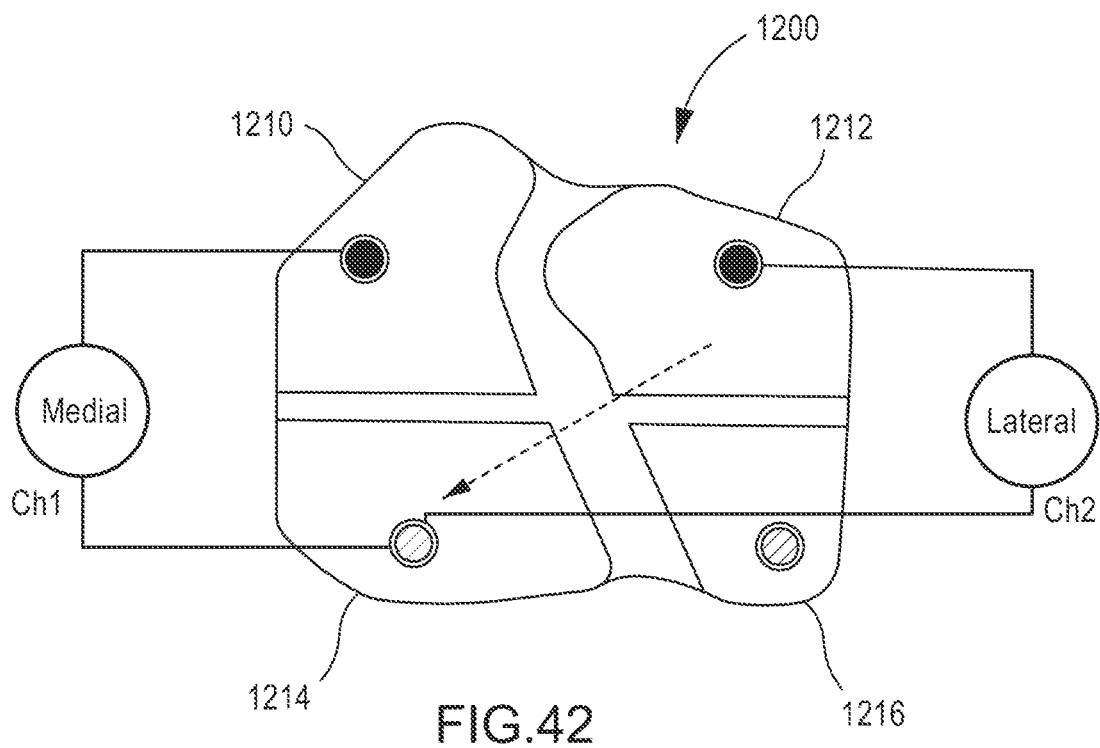

As shown in FIG. 42, during a second time period, the electric stimulator 1400 sends a second stimulation signal to the second cathodic electrode 1212 to cause the second cathodic electrode 1212 to provide an electrical current to the first anodic electrode 1214, which forms a portion of the second channel Ch2 at least during the second time period, through a portion of the neuromuscular system of the limb between the second cathodic electrode 1212 and the first anodic electrode 1214. The second time period can be subsequent to the first time period. More particularly, the second time period can occur substantially immediately after the first time period.

Figure 43:
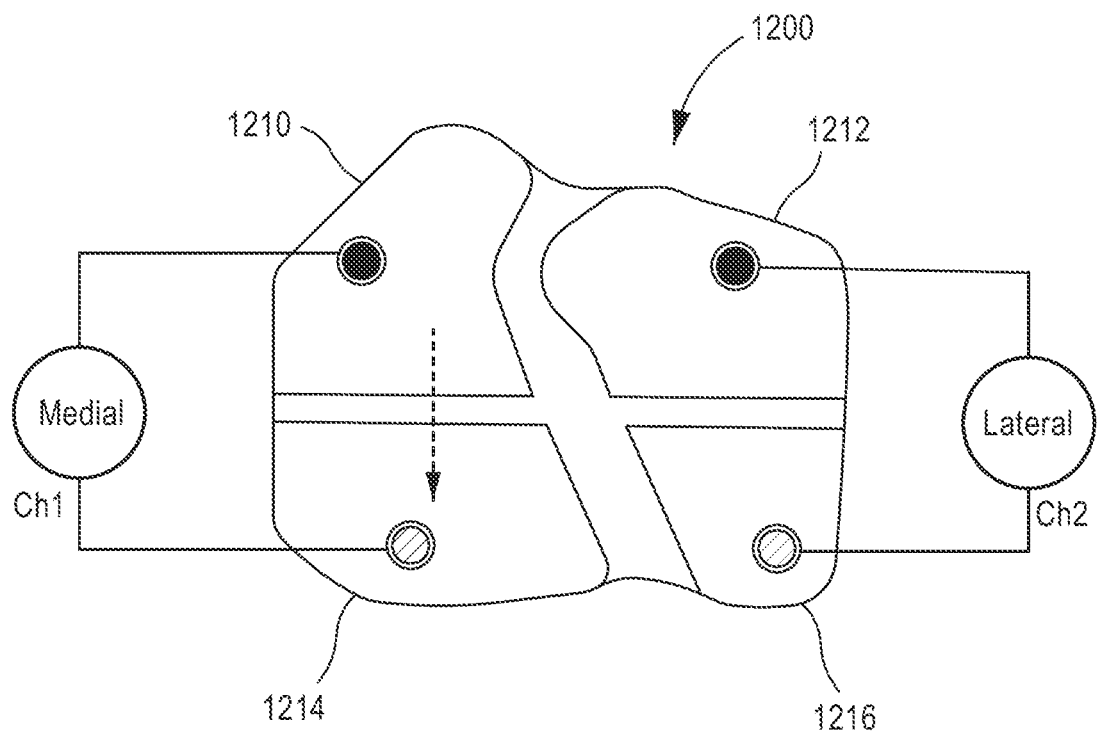

As shown in FIG. 43, during a third time period, the electric stimulator 1400 sends a third stimulation signal to the first cathodic electrode 1210 to cause the first cathodic electrode 1210 to provide an electrical current to the first anodic electrode 1214, which forms a portion of the first channel Ch1 at least during the third time period, through a portion of the neuromuscular system of the limb between the first cathodic electrode 1210 and the first anodic electrode 1214. The third time period can be subsequent to the second time period. More particularly, the third time period can occur substantially immediately after the second time period.

Figure 44:
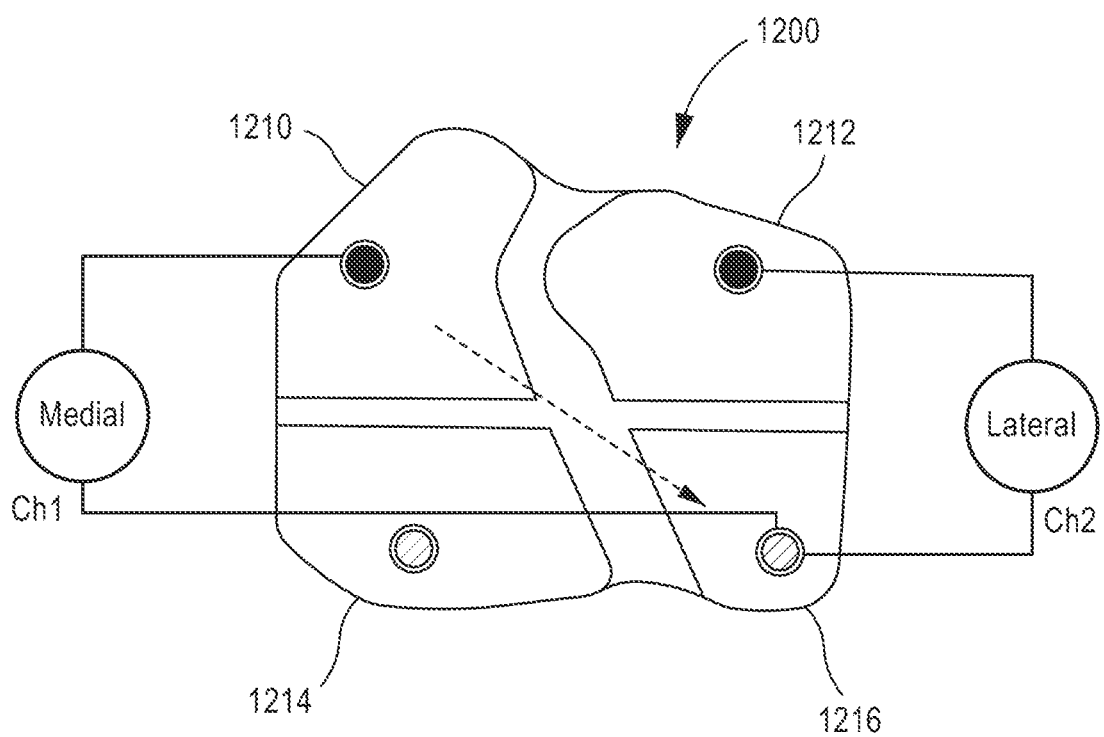

As shown in FIG. 44, during a fourth time period, the electric stimulator 1400 sends a fourth stimulation signal to the first cathodic electrode 1210 to cause the first cathodic electrode 1210 to provide an electrical current to the second anodic electrode 1216, which forms a portion of the first channel Ch1 at least during the fourth time period, through a portion of the neuromuscular system of the limb between the second cathodic electrode 1212 and the first anodic electrode 1214. The fourth time period can be subsequent to the third time period. More particularly, the fourth time period can occur substantially immediately after the third time period.

Each stimulation signal (e.g., the first, second, third and fourth signals) is associated with a set of parameters for an electrical current to be provided to the respective electrode. In some embodiments, the first stimulation signal is associated with a first set of parameters, the second stimulation signal is associated with a second set of parameters, the third stimulation signal is associated with a third set of parameters, and the fourth stimulation signal is associated with a fourth set of parameters. The foregoing sets of parameters are collectively configured to produce a desired movement or produce a desired position of a portion of the limb (e.g., the foot, during a gait event). Individual parameters in each of the foregoing sets can have a different value from the value of a corresponding parameter in each of the other sets. For example, an intensity of the current produced in response to each stimulator signal can be different, thus providing for steering of the current in a desired manner through the neuromuscular system of the limb. In this manner, parameter values for each set can be adjusted or modified, e.g., via a control device electrically coupled to the stimulator, until the desired movement or position of the limb portion is produced.

In some embodiments, the electric stimulator 1400 can receive and/or send signals to a set of external and/or implanted electrical devices via any suitable communication mode. For example, in some embodiments, the electric stimulator 1400 can include two, three, four, five, six, or more communication and/or electrical channels that can be operable in sending and/or receiving signals to and/or from, respectively, the electrode assembly 1200, a sensor (not shown, e.g., sensor 130), and/or any other suitable electronic device operably coupled thereto. In some embodiments, at least a portion of the communication and/or electrical channels can be associated with sending and/or receiving a signal via a wireless communication modality (e.g., a modality, format, and/or the like associated with WiFi®, Bluetooth®, near field communication (NFC), cellular communication such as, short message service (SMS) or multimedia message service (MMS), and/or the like), as described in further detail herein.

Although the system 1000 has been shown and described as including an electrode assembly (e.g., electrode assembly 1200, 1201, 1203, 1205) including a certain number of electrodes (e.g., two, three, four, six), in some embodiments, an electrode assembly including any suitable number of electrodes can be included in the orthosis 1050 of the system 1000.

Figure 30:
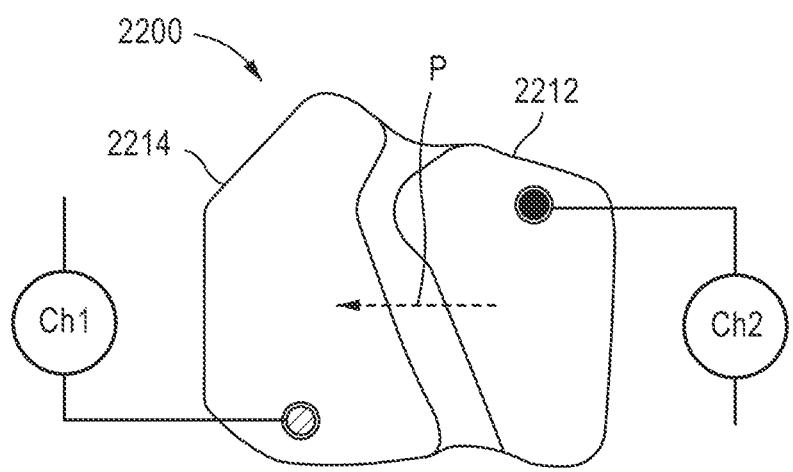

For example, referring to FIG. 30, in some embodiments, a "quick-fit" electrode assembly according to an embodiment including two electrodes (i.e., a cathodic electrode 2212 and an anodic electrode 2214) can be used with the system 1000. A first male connector (not shown) of the electrode assembly 2200 is configured to be coupled to the connector 1232 of the frame assembly 1100 to electrically couple the cathodic electrode 2212 to the electric stimulator 1400. The cathodic electrode 2212 has a size and shape such that the electrode 2212 overlies the connector 1236 of the frame assembly 1110, thereby being configured to prevent inadvertent stimulation of the tissue via the connector 1236, which may not be mechanically and/or electrically coupled to the electrode assembly 2200 in this embodiment. A second male connector (not shown) of the electrode assembly 2200 is configured to be coupled to the connector 1234 of the frame assembly 1100 to electrically couple the anodic electrode 2214 to the electric stimulator 1400. The anodic electrode 2214 has a size and shape such that the electrode 2212 overlies the connector 1230 of the frame assembly

1110, thereby being configured to prevent inadvertent stimulation of the tissue via the connector 1230, which may not be mechanically and/or electrically coupled to the electrode assembly 2200 in this embodiment. In some embodiments, at least one of the first male connector and the second male connectors of the electrode assembly 2200 includes a visual indicium configured to assist a user in identifying to which electrode connector 1230, 1232, 1234, 1236 the respective male connector is configured to be coupled. For example, the first male connector can include a color coded portion indicating that the first male connector should be coupled to a predetermined one of electrode connectors 1230, 1232, 1234, 1236 of the electrode assembly 2200, and the second male connector can include a color coded portion indicating that the second male connector should be coupled to a predetermined one of another of the electrode connectors 1230, 1232, 1234, 1236.

The electric stimulator 1400 is configured to provide stimulation during a first time period via the second channel Ch2 such that an electrical current flows from the cathodic electrode 2212 into the neuromuscular system of the limb and through a portion of the neuromuscular system of the limb between the cathodic electrode 1210 and the anodic electrodes 2214, as represented by arrow P in FIG. 30. At least a portion of the current flowing into the tissue via the second channel Ch2 can be returned (or flow) from the tissue to the stimulator 1400 via the anodic electrode 2214 and the first channel Ch1. In some embodiments, the stimulation is monopolar. In other embodiments, the stimulation is bipolar.

Figure 45A:
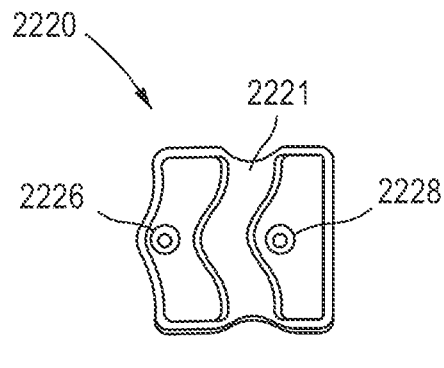
FIGS. 45A-45B are bottom and top views, respectively of an electrode assembly of the FES orthosis of FIG. 4 according to an embodiment.
Figure 45B:
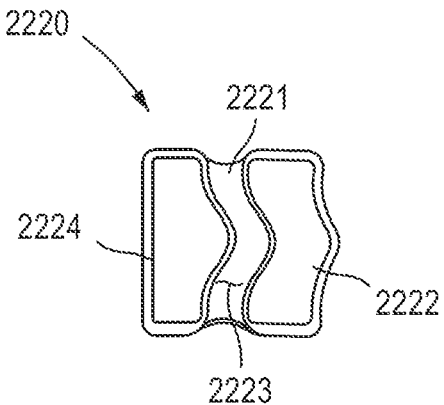

Additional examples of electrode assemblies including two electrodes are shown in FIGS. 45A-46B. For example, as shown in FIGS. 45A-45B, an electrode assembly 2221 according to an embodiment includes a panel 2221 and two electrodes (or electrode regions) 2222, 2224 arranged thereon. A non-conductive region 2223 of the panel 2221 is disposed between the electrodes 2222, 2224. As shown in FIGS. 45A-45B, the non-conductive region 2223 between the electrodes 2222, 2224 is curved or non-linear. For example, in some embodiments, the non-conductive region 2223 is in the shape of a wave. Similarly, each of the electrodes 2222, 2224 includes a substantially wave shaped edge or perimeter portion disposed on opposing sides of the non-conductive region 2223, which perimeter portions can be substantially parallel. The electrodes 2222, 2224 can be substantially similar in form and/or function to any electrode described herein. For example, one of the electrodes 2222, 2224 can be a cathodic electrode and the other of the electrodes 2222, 2224 can be an anodic electrode. The electrode assembly 2220 is configured for use with the orthosis 1050, and configured to be coupled to the frame assembly 1100. The electrode assembly 2220 can be coupled to the frame assembly 1100 in any suitable manner described herein. The electrodes 2222, 2224 each are associated with a connector 2226, 2228, respectively, configured to be electrically coupled to the electric stimulator 1400 via corresponding connectors of the frame assembly 1100. As shown, the connectors 2226, 2228 are male connectors configured to be removably coupled to complementary connectors of the frame assembly 1100. Because the electrode assembly 2220 includes only two male connectors, two complementary connectors on the frame assembly may be unused with respect to the electrode assembly 2220. As such, a connector cover (e.g. connector cover 1270 shown and described herein with respect to FIG. 6A) can optionally be used with the unused connectors. Although the electrode assembly 2220 is shown and described herein as including two connectors, in other embodiments, the electrode assembly can include any suitable number of connectors, such as three, four or more connectors. Additionally, although the electrode assembly 2220 is shown as including male connectors, in another embodiment, the electrode assembly can include female connectors configured to be coupled to complementary male connectors of a frame assembly.

Figure 46A:
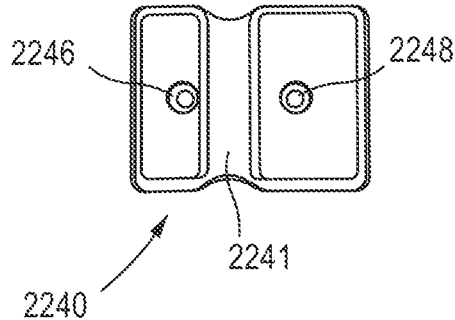
FIGS. 46A-46B are bottom and top views, respectively of an electrode assembly of the FES orthosis of FIG. 4 according to an embodiment.
Figure 46B:
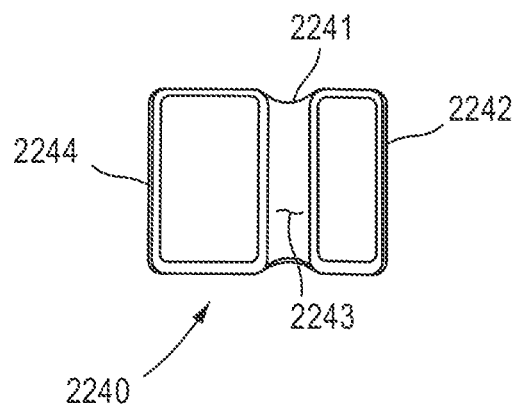

In another example, as shown in FIGS. 46A-46B, an electrode assembly 2240 according to an embodiment includes a panel 2241 and two electrodes (or electrode regions) 2242, 2244 arranged thereon. A non-conductive region 2243 of the panel 2241 is disposed between the electrodes 2242, 2244. As shown in FIG. 46B, the non-conductive region 2243 between the electrodes 2242, 2244 is substantially linear. Similarly, each of the electrodes 2242, 2244 includes a substantially linear edge or perimeter portion, which perimeter portions can be substantially parallel and disposed on opposing sides of the non-conductive region 2243. The electrodes 2242, 2244 can be substantially similar in form and/or function to any electrode described herein. For example, one of the electrodes 2242, 2244 can be a cathodic electrode and the other of the electrodes 2242, 2244 can be an anodic electrode. The electrode assembly 2240 is configured for use with the orthosis 1050, and configured to be coupled to the frame assembly 1100. The electrode assembly 2240 can be coupled to the frame assembly 1100 in any suitable manner described herein. The electrodes 2242, 2244 each are associated with a connector 2246, 2248, respectively, configured to be electrically coupled to the electric stimulator 1400 via a corresponding connector of the frame assembly 1100. As shown, the connectors 2246, 2248 are male connectors configured to be removably coupled to complementary connectors of the frame assembly 1100. Because the electrode assembly 2240 includes only two male connectors, two complementary connectors on the frame assembly may be unused with respect to the electrode assembly 2240. As such, a connector cover (such as connector cover 1270 shown and described herein with respect to FIG. 6A) can optionally be used with the unused connectors. Although the electrode assembly 2240 is shown and described herein as including two male connectors, in other embodiments, the electrode assembly can include any suitable number of connectors, such as three, four or more connectors. Additionally, although the electrode assembly 2240 is shown as including male connectors, in another embodiment, the electrode assembly can include female connectors configured to be coupled to complementary male connectors of a frame assembly.

Although the electrode assemblies 2220, 2240 are shown with different electrode shapes, the electrode assemblies 2220, 2240 can otherwise be substantially similar or identical in many respects to electrode assembly 2200, and can be used for FES in a manner similar to that described above with respect to electrode assembly 2200, and so such details are not reproduced here.

Although the system 1000 has been shown and described as including an electrode assembly (e.g., electrode assembly 120, 1200, 1201, 1203, 1205) in which the cathodic electrodes (e.g., electrodes 1210, 1212) are disposed vertically above the anodic electrode(s) when the electrode assembly is coupled to the frame assembly 1110 and the orthosis 1050 is donned by the patient (or proximally to the anodic electrode(s) with respect to the patient's torso), in some embodiments, an electrode assembly configured for use with the orthosis 1050 can include cathodic and anodic electrodes that are differently positioned or distributed with respect to the panel (and thus with respect to the patient's limb when the orthosis 1050 is donned).

Figure 31:
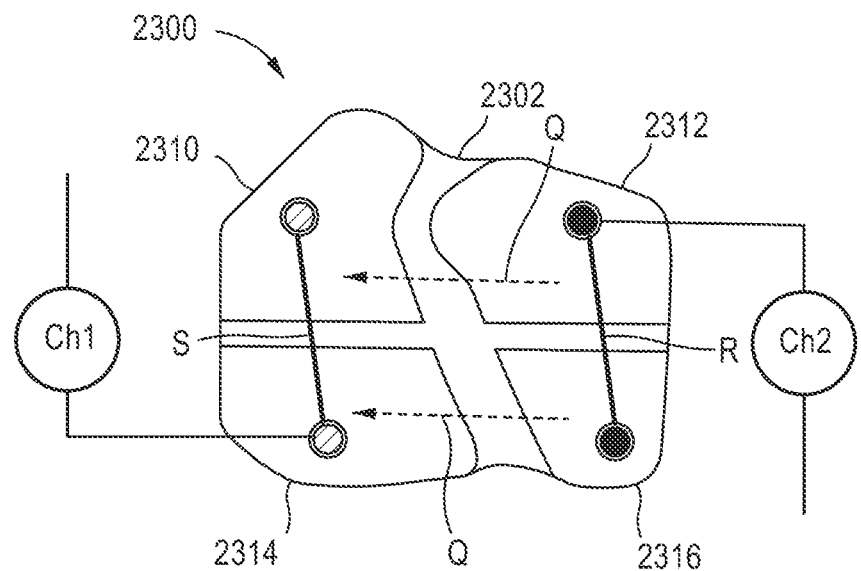

For example, referring to FIG. 31, an electrode assembly 2300 is configured for use with the FES system 1000 described herein. The electrode assembly 2300 includes four electrodes 2310, 2312, 2314, 2316 formed on, disposed on, or otherwise coupled to a panel 2302, of which two electrodes 2312, 2316 are cathodic electrodes disposed on substantially a first half of the panel 2302 such that the first cathodic electrode 2312 is proximal to the second cathodic electrode 2316 with respect to the patient's torso when the orthosis 1050 is donned on the patient's leg and the patient is standing. The other two electrodes 2310, 2314 of the electrode assembly 2300 are anodic electrodes disposed on substantially a second half of the panel 2302 such that the first anodic electrode 2310 is proximal to the second anodic electrode 2314 with respect to the patient's torso when the orthosis 1050 is donned on the patient's leg and the patient is standing.

The electric stimulator 1400 can be configured to provide stimulation during a time period via the second channel Ch2 such that an electrical current flows from the stimulator 1400 to the first cathodic electrode 2312 and the second cathodic electrode 2316 and from the cathodic electrodes 2312, 2316 into the neuromuscular system of the limb and through a portion of the neuromuscular system of the limb between the cathodic electrodes 2312, 2316 and the first and second anodic electrodes 2310, 2314, as generally represented by arrows Q in FIG. 31. The first cathodic electrode 2312 and the second cathodic electrode 2316 can be operable as a "common" cathode, for example, by including an electrical short (represented by line R in FIG. 31) between the first cathodic electrode 2312 and the second cathodic electrode 2316. The first anodic electrode 2310 and the second anodic electrode 2314 can be operable as a "common" anode, as described herein, which can be facilitated by an electrical short provided between the first and second anodic electrodes 2310, 2314, as represented by line S in FIG. 31.

At least a portion of the electrical current flowing into the tissue via the second channel Ch2 can be returned (or flow) from the tissue to the stimulator 1400 via the anodic electrodes 2310, 2314 and the first channel Ch1.

Figure 32:
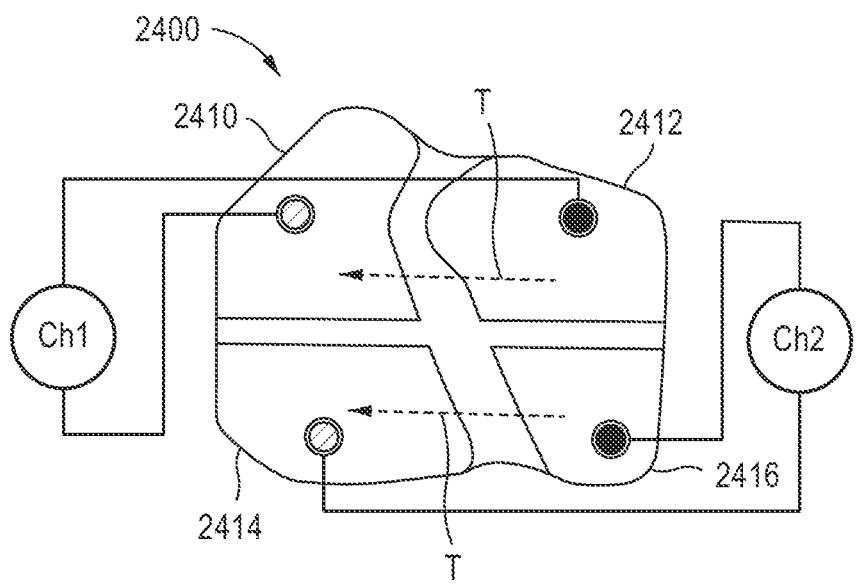

In another example, referring to FIG. 32, an electrode assembly 2400 is configured for use with the FES system 1000 described herein. The electrode assembly 2400 can be substantially similar in form to electrode assembly 2300 shown and described herein with respect to FIG. 31. The electrode assembly 2400 includes four electrodes 2410, 2412, 2414, 2416 formed on, disposed on, or otherwise coupled to a panel 2402, of which two electrodes 2412, 2416 are cathodic electrodes disposed on substantially a first half of the panel 2402 such that the first cathodic electrode 2412 is proximal to the second cathodic electrode 2416 with respect to the patient's torso when the orthosis 1050 is donned on the patient's leg and the patient is standing. The other two electrodes 2410, 2414 of the electrode assembly 2400 are anodic electrodes disposed on substantially a second half of the panel 2402 such that the first anodic electrode 2410 is proximal to the second anodic electrode 2414 with respect to the patient's torso when the orthosis is donned 1050 on the patient's leg and the patient is standing. Said another way, the cathodic electrodes 2412, 2416 are substantially vertically aligned with respect to the panel 2402 and the anodic electrodes 2410, 2414 are substantially vertically aligned with respect to the panel 2402 when the panel 2402 is coupled to the orthosis 1050, the orthosis 1050 is donned on the patient's leg, and the patient is standing.

The electric stimulator 1400 can be configured to provide stimulation during a time period via the first channel Ch1 such that an electrical current flows from the stimulator 1400 to at least one of the first cathodic electrode 2412 and the first anodic electrode 2410 and from the at least one of the first cathodic electrode 2412 and/or the first anodic electrode 2410 into a portion of the neuromuscular system of the limb and through a portion of the neuromuscular system of the limb between the first cathodic electrode 2412 and the first anodic electrode 2410. The electric stimulator can be configured to provide stimulation during the time period via the second channel Ch2 such that an electrical current flows from the stimulator 1400 to at least one of the second cathodic electrode 2416 and the second anodic electrode 2414 and from the at least one of the second cathodic electrode 2416 and/or the second anodic electrode 2414 into a portion of the neuromuscular system of the limb between the second cathodic electrode 2416 and the second anodic electrode 2414. The flow of electrical current from each of the first channel Ch1 and the second channel Ch2 can flow through the neuromuscular system of the limb as generally represented by arrows T in FIG. 32. Thus, in use, the electrode assembly 2400 can provide a current flow through the tissue that has a similar pattern and/or physiological effect on the neuromuscular system as that resulting from operation of the electrode assemblies 2200, 2300 shown and described herein with respect to FIGS. 30-31. At least a portion of the electrical current flowing into the tissue via the first channel Ch1 and/or the second channel Ch2 can be returned (or flow) from the tissue to the stimulator 1400 via the first anodic electrode the first channel Ch1 and/or via the second anodic electrode 2414 and the second channel Ch2. In some embodiments, the stimulation is monopolar. In some embodiments, the stimulation is bipolar.

Figure 33:
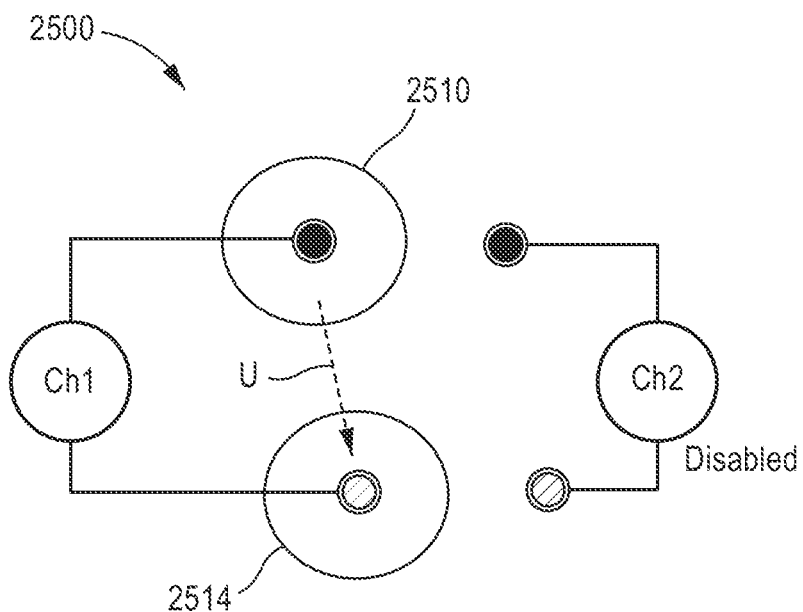

Although the FES system 1000 has been illustrated and described herein as including an electrode assembly (e.g., electrode assembly 120, 1200, 1201, 1203, 1205, 2200, 2300, 2400) having a plurality of electrodes fixedly coupled to a panel, in some embodiments, the system 1000 is configured for use with one or more conventional electrodes (e.g., a hydrogel electrode, a small cloth electrode, or the like). For example, referring to FIG. 33, in one embodiment, an electrode assembly 2500 includes a cathodic electrode 2510 and an anodic electrode 2514, each of which can be one of a hydrogel electrode, small cloth electrode, or the like. The cathodic electrode 2510 is removably coupled to the first electrode connector 1230 of the frame assembly 1100, and the anodic electrode 2514 is removably coupled to the third electrode connector 1234 of the frame assembly 1100. Thus, the cathodic electrode 2510 and the anodic electrode 2514 form at least a portion of a first channel Ch1. As shown, in this embodiment, the second stimulation channel is operably disabled or otherwise non-functional, and thus no stimulation is provided via the second stimulation channel Ch2. In some embodiments, no electrodes are coupled to the second stimulation channel Ch2, e.g., to the second electrode connector 1232 and/or the fourth electrode connector 1236. In such embodiments, the unused electrode connectors 1232, 1236 can optionally have one or more connector covers disposed thereon to prevent the inadvertent flow of electrical current therefrom during FES using the first channel Ch1.

The electric stimulator 1400 can be configured to provide stimulation during a time period via the first channel Ch1 such that an electrical current flows from the stimulator 1400 to at least one of the cathodic electrode 2510 and the anodic electrode 2514 and from the cathodic electrode 2510 and/or the anodic electrode 2514 into a portion of the neuromuscular system of the limb and through a portion of the neuromuscular system of the limb between the cathodic electrode 2510 and the anodic electrode 2514. For example, the electrical current can be caused to flow from the cathodic electrode 2510 towards the anodic electrode 2514, as generally represented by arrow U in FIG. 33. In this manner, although the system 1000 is configured for multi-channel stimulation, the system 1000, and stimulator 1400 particularly, can be configured to selectively provide single-channel stimulation of at least a portion of the neuromuscular system of the limb. In some embodiments, at least a portion of the electrical current can be returned to the stimulator 1400 from the tissue via the anodic electrode 2514 and the first channel Ch1. In some embodiments, the stimulation is monopolar. In some embodiments, the stimulation is bipolar.

Figure 34:
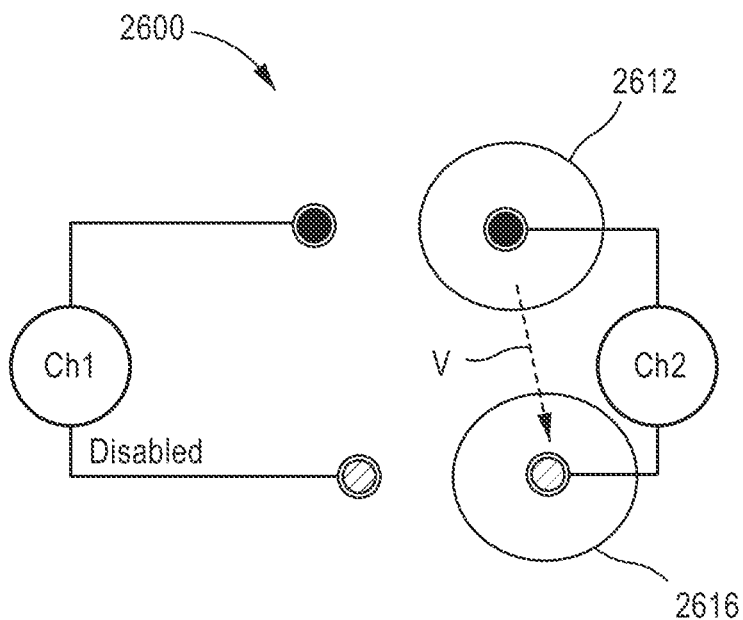

In another example, referring to FIG. 34, in one embodiment, an electrode assembly 2600 includes a cathodic electrode 2612 and an anodic electrode 2616. The cathodic electrode 2612 is removably coupled to the second electrode connector 1232 of the frame assembly 1100, and the anodic electrode 2616 is removably coupled to the fourth electrode connector 1236 of the frame assembly 1100. Thus, the cathodic electrode 2612 and the anodic electrode 2614 form at least a portion of the second channel Ch2. As shown, in this embodiment, the first stimulation channel Ch1 is operably disabled or otherwise non-functional, and thus no stimulation is provided via the first stimulation channel Ch1. In some embodiments, no electrodes are coupled to the first stimulation channel Ch1, e.g., to the first electrode connector 1230 and/or the third electrode connector 1234. In such embodiments, the unused electrode connectors 1230, 1234 can optionally have one or more connector covers disposed thereon.

The electric stimulator 1400 can be configured to provide stimulation during a time period via the second channel Ch2 such that an electrical current flows from the stimulator 1400 to at least one of the cathodic electrode 2612 and the anodic electrode 2616 and from the cathodic electrode 2612 and/or the anodic electrode 2616 into a portion of the neuromuscular system of the limb and through a portion of the neuromuscular system of the limb between the cathodic electrode 2612 and the anodic electrode 2616. For example, the electrical current can be caused to flow from the cathodic electrode 2612 towards the anodic electrode 2616, as generally represented by arrow V in FIG. 34. In this manner, although the system 1000 is configured for multi-channel stimulation, the system 1000, and stimulator 1400 particularly, can be configured to selectively provide single-channel stimulation of at least a portion of the neuromuscular system of the limb. In some embodiments, at least a portion of the electrical current can be returned to the stimulator 1400 from the tissue via the anodic electrode 2616 and the second channel Ch2. In some embodiments, the stimulation is monopolar. In some embodiments, the stimulation is bipolar.

Figure 35:
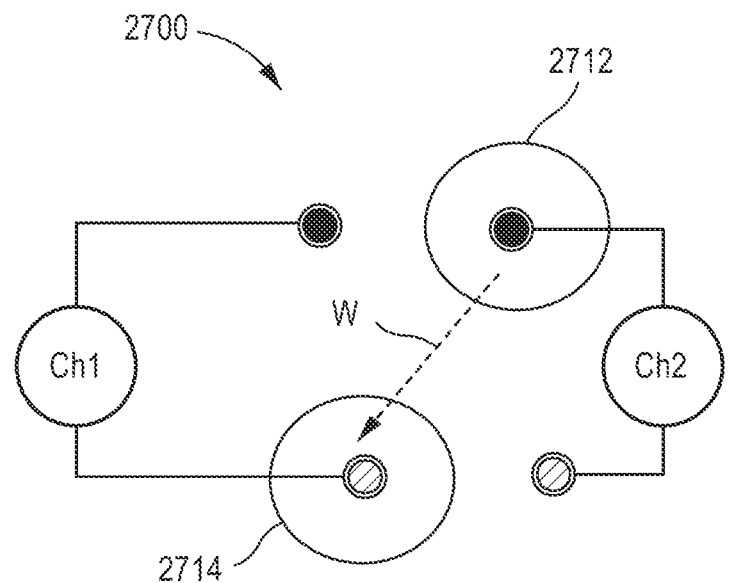

In still another example, referring to FIG. 35, in one embodiment, an electrode assembly 2700 includes a cathodic electrode 2712 and an anodic electrode 2714. The cathodic electrode 2712 is removably coupled to the second electrode connector 1232 of the frame assembly 1100, and the anodic electrode 2714 is removably coupled to the third electrode connector 1234 of the frame assembly 1100. Thus, the cathodic electrode 2510 forms at least a portion of the second channel Ch2, and the anodic electrode 2714 forms at least a portion of the first channel Ch1. The first electrode connector 1230 and fourth electrode connector 1236 are optionally not coupled to an electrode. As such, the unused electrode connectors 1230, 1236 can optionally have one or more connector covers disposed thereon to prevent the inadvertent flow of electrical current therethrough during FES with an orthosis 1050 including the electrode assembly 2700.

The electric stimulator 1400 can be configured to provide stimulation during a time period via the second channel Ch2 such that an electrical current flows from the stimulator 1400 to the cathodic electrode 2712 and/or via the first channel Ch1 such that an electrical current flows from the stimulator 1400 to the anodic electrode 2714. More particularly, the electric stimulator 1400 can be configured to provide a flow of electrical current via the second channel Ch2 to the cathodic electrode 2712 such that the cathodic electrode 2712 provides the flow of electrical current to at least a portion of a neuromuscular system of the limb such that the electrical current flows through a portion of the neuromuscular system of the limb between the cathodic electrode 2712 and the anodic electrode 2714, as generally represented by arrow W in FIG. 35. At least a portion of the electrical current can be returned to the stimulator 1400 from the tissue via the anodic electrode 2714 and the first channel Ch1. In this manner, the electric stimulator 1400 can be configured to provide cross-channel stimulation of the tissue of the neuromuscular system of the limb. In some embodiments, the stimulation is monopolar. In some embodiments, the stimulation is bipolar.

Although the orthosis 1050 has been shown and described herein with respect to FIG. 27 having a "common anode" configuration and as including the first channel Ch1 formed in part by the first cathodic electrode 1220, the anodic electrode 1224 and electrode connectors 1230, 1234 (and associated wiring), and the second channel Ch2 formed in part by the second cathodic electrode 1222, the anodic electrode and electrode connectors 1232, 1236 (and associated wiring), in other embodiments, the orthosis 1050 can have a different "common anode" configuration. For example, referring to FIG. 36, a system is configured for stimulation of at least a portion of a neuromuscular system of a limb (e.g., a leg) via a first channel Ch1 and a second channel Ch2. The first channel Ch1 is formed, at least in part, by a first cathodic electrode 2810, which is coupled to the first electrode connector 1230 of the frame assembly 1100, and the anodic electrode 2814, via the fourth electrode connector 1236 which is coupled to the anodic electrode 2814, as well as the stimulator 1400 and circuitry and/or additional connectors therebetween. The second channel Ch2 is formed, at least in part, by the second cathodic electrode 2812, which is coupled to the second electrode connector 1232 of the frame assembly 1100, and the anodic electrode 2814, via the third electrode connector 1234 which is coupled to the anodic electrode 2814, as well as the stimulator 1400 and circuitry and/or additional connectors therebetween. In some embodiments, the connection of wiring (e.g., wires 1244, 1246) associated with the electrode connectors 1234, 1236 to the electric stimulator 1400 is reversed. In some embodiments, such as when an orthosis including the electrode assembly 2800 is donned on the right leg of the patient or another limb on the right half of the patient's body, the first channel Ch1 can be considered a medial (stimulation) channel and the second channel Ch2 can be considered a lateral (stimulation) channel.

The electric stimulator 1400 is configured to provide stimulation during a time period via the first channel Ch1 such that an electrical current flows from the first cathodic electrode 1220 into the neuromuscular system of the limb and through a portion of the neuromuscular system of the limb between the first cathodic electrode 1220 and the anodic electrode 1224. In some embodiments, at least a portion of the electrical current flowing via the first channel Ch1 is returned to the electric stimulator 1400 via the anodic electrode 1224 and one or more of connectors 1234, 1236. In some embodiments, the stimulation is monopolar. In other embodiments, the stimulation is bipolar. The electric stimulator 1400 is configured to provide stimulation during the time period via the second channel Ch2 such that an electrical current flows from the second cathodic electrode 1222 into the neuromuscular system of the limb and through a portion of the neuromuscular system of the limb between the second cathodic electrode 1222 and the anodic electrode 1224. In some embodiments, at least a portion of the electrical current flowing via the second channel Ch2 is returned to the electric stimulator 1400 via the anodic electrode 1224 and one or more of connectors 1234, 1236. In some embodiments, the stimulation is monopolar. In other embodiments, the stimulation is bipolar.

Figure 36:
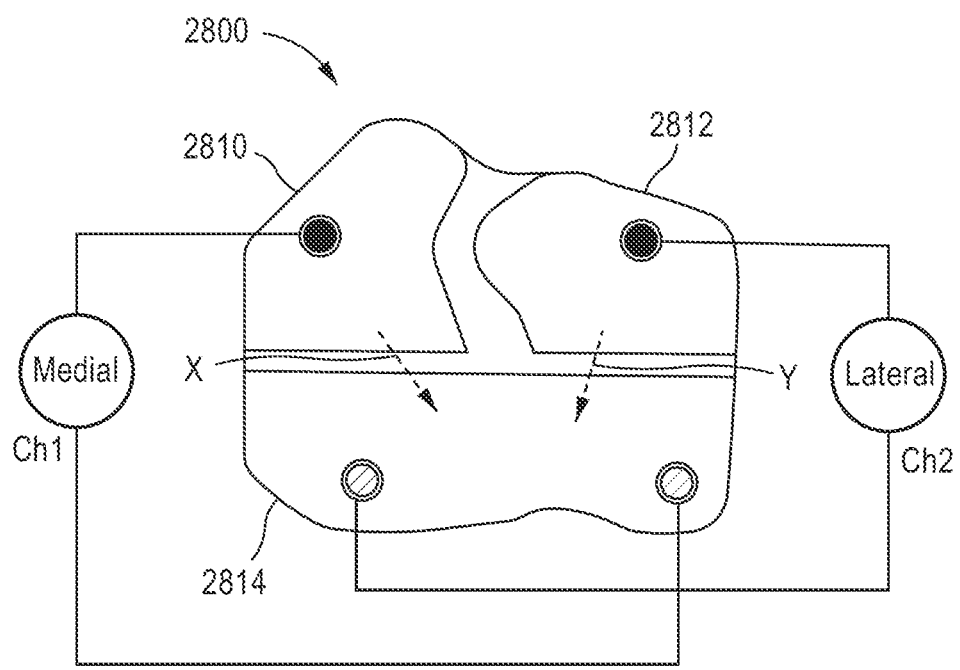

In this manner, the system 100 can be considered to be configured to provide two stimulation channels through the neuromuscular system using a common anode, with a current flow through the tissue generally represented by arrows X and Y in FIG. 36. An FES system implementing such a common anode configuration for providing FES to neuromuscular system can provide a greater disbursement of the flow of electrical current through the neuromuscular system than that provided by a single-channel stimulation system. Additionally, because one or more parameters of the current flow, such as the current's intensity, along each channel (i.e., the first channel Ch1 and the second channel Ch2) are independently programmed to or selected by the stimulator, the disbursement of the electrical current through the neuromuscular system can be targeted or otherwise manipulated by controlling the one or more parameters (e.g., increasing or decreasing a current's amplitude), thereby promoting a desired response by the neuromuscular system, such as dorsiflexion, plantarflexion, inversion or eversion of the foot.

Although the orthosis 1050 has been shown and described herein with respect to FIG. 30 as including an electrode assembly 2200 including two electrodes (i.e., electrodes 2212, 2214) coupled to the orthosis 1050 such that the first channel Ch1 is formed in part by the anodic electrode 2214 and electrode connector 1234 (and associated wiring), and the second channel Ch2 formed in part by the cathodic electrode 2212 and electrode connector 1236 (and associated wiring), in other embodiments, the orthosis 1050 can have a different configuration for use with an electrode assembly including two electrodes (e.g., a single cathodic electrode and a single anodic electrode).

Figure 37:
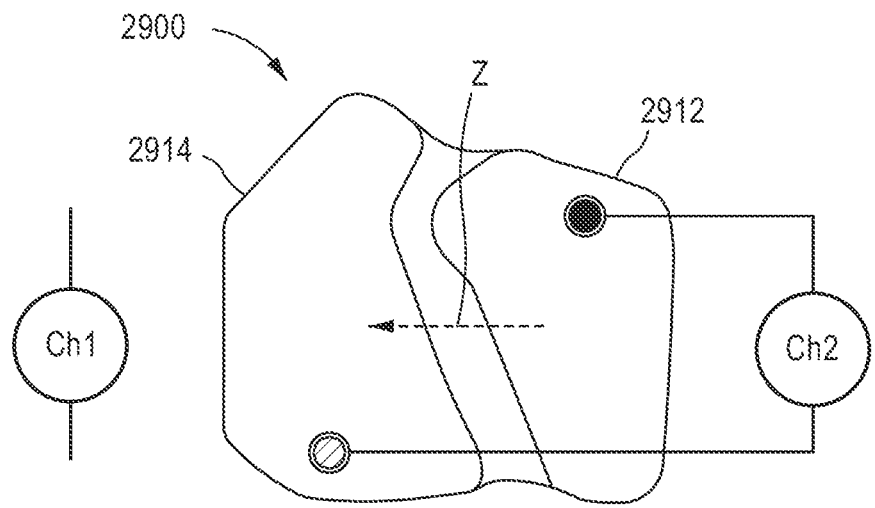

For example, referring to FIG. 37, a system according to an embodiment is configured for use with a "quick-fit" electrode assembly including two electrodes (e.g., a cathodic electrode 2912 and an anodic electrode 2914) having a different channel configuration than that shown in FIG. 30. A first male connector (not shown) of the electrode assembly 2900 is configured to be coupled to the electrode connector 1232 of the frame assembly 1100 to electrically couple the cathodic electrode 2912 to the electric stimulator 1400. The cathodic electrode 2912 has a size and shape such that the electrode 2912 overlies the connector 1236 of the frame assembly 1110, thereby being configured to prevent inadvertent stimulation of the tissue via the connector 1236. A second male connector (not shown) of the electrode assembly 2900 is configured to be coupled to the connector 1234 of the frame assembly 1100 to electrically couple the anodic electrode 2914 to the electric stimulator 1400. The anodic electrode 2914 has a size and shape such that the electrode 2914 overlies the connector 1230 of the frame assembly 1110, thereby being configured to prevent inadvertent stimulation of the tissue via the connector 1230.

The system 1000 includes a second stimulation channel Ch2 formed, at least in part, by the cathodic electrode 2912, electrode connector 1232, anodic electrode 2914 and electrode connector 1234. Although the system 1000 is configured to provide stimulation via a first stimulation channel Ch1, in the embodiment shown in FIG. 37, the first stimulation channel Ch1 is selectively unused or non-functional. In some embodiments, the connection of wiring (e.g., wires 1244, 1246) between the electrode connectors 1234, 1236 and the electric stimulator 1400 is reversed to facilitate functionality of the second channel Ch2. In some embodiments, such as when an orthosis including the electrode assembly 2800 is donned on the right leg of the patient or another limb on the right half of the patient's body, the first channel Ch1 can be considered a medial (stimulation) channel and the second channel Ch2 can be considered a lateral (stimulation) channel.

The electric stimulator 1400 is configured to provide stimulation during a time period via the second channel Ch2 such that an electrical current flows from the cathodic electrode 2912 into the neuromuscular system of the limb and through a portion of the neuromuscular system of the limb between the cathodic electrode 2912 and the anodic electrodes 2914, as represented by arrow Z in FIG. 37. At least a portion of the current flowing into the tissue via the second channel Ch2 can be returned (or flow) from the tissue to the stimulator 1400 via the anodic electrode 2914 and the second channel Ch2.

Although the system 1000 has been illustrated and described herein with respect to FIG. 35 as being configured for cross-channel stimulation utilizing an electrode assembly 2700 including a panel with a first electrode 2712 coupled to the second electrode connector 1232 and forming a portion of a second stimulation channel Ch2, and a second electrode 2714 coupled to the third electrode connector 1234 and forming a portion of a first stimulation channel Ch1, in other embodiments, a system can define such a channel arrangement using one or more conventional electrodes (e.g., hydrogel, cloth, small cloth, or the like).

Figure 38:
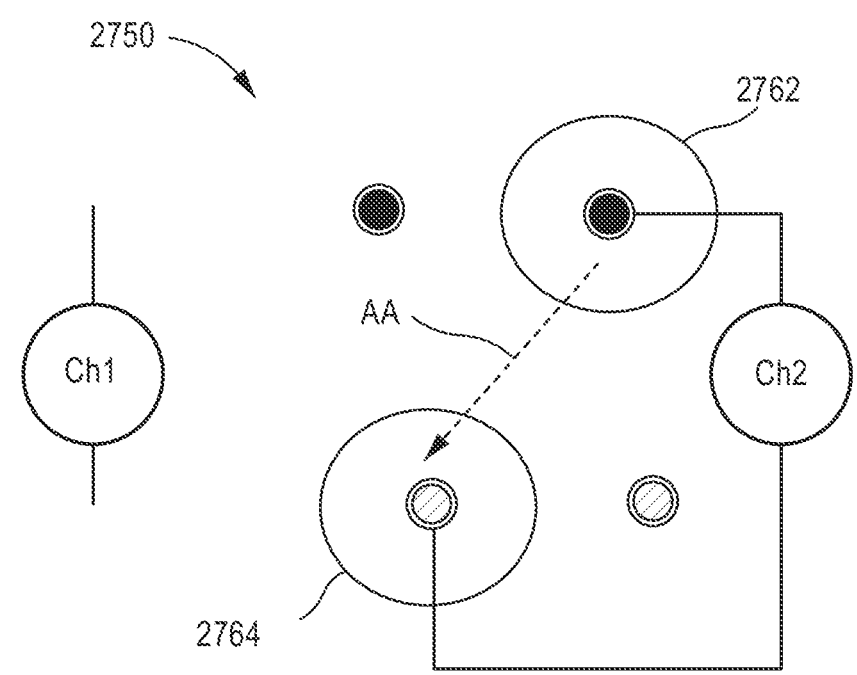

For example, referring to FIG. 38, an electrode assembly 2750 includes a cathodic electrode 2762 and an anodic electrode 2764. The cathodic electrode 2762 can be removably coupled to the second electrode connector 1232 of the frame assembly 1100, and the anodic electrode 2764 can be removably coupled to the third electrode connector 1234 of the frame assembly 1100, which collectively form at least a portion of the second channel Ch2. Although the system is configured to provide stimulation via a first stimulation channel Ch1, in the embodiment shown in FIG. 38, the first stimulation channel Ch1 is selectively disabled, unused or otherwise non-functional. In some embodiments, the connection of wiring (e.g., wires 1244, 1246) between the electrode connectors 1234, 1236 and the electric stimulator 1400 is reversed to facilitate functionality of the second channel Ch2. The first electrode connector 1230 and fourth electrode connector 1236 are optionally not coupled to an electrode. As such, the unused electrode connectors 1230, 1236 can optionally have one or more connector covers disposed thereon to prevent the inadvertent flow of electrical current therethrough during FES with an orthosis 1050 including the electrode assembly 2750.

The electric stimulator 1400 can be configured to provide stimulation during a time period via the second channel Ch2 such that an electrical current flows from the stimulator 1400 to the cathodic electrode 2762 to at least a portion of the neuromuscular system of the limb, such that the electrical current flows through a portion of the neuromuscular system of the limb between the cathodic electrode 2762 and the anodic electrode 2764, as generally represented by arrow AA in FIG. 38. In some embodiments, at least a portion of the electrical current can be returned to the stimulator 1400 from the tissue via the anodic electrode 2764 and the second channel Ch2. In some embodiments, the stimulation is monopolar. In some embodiments, the stimulation is bipolar.

Figure 47:
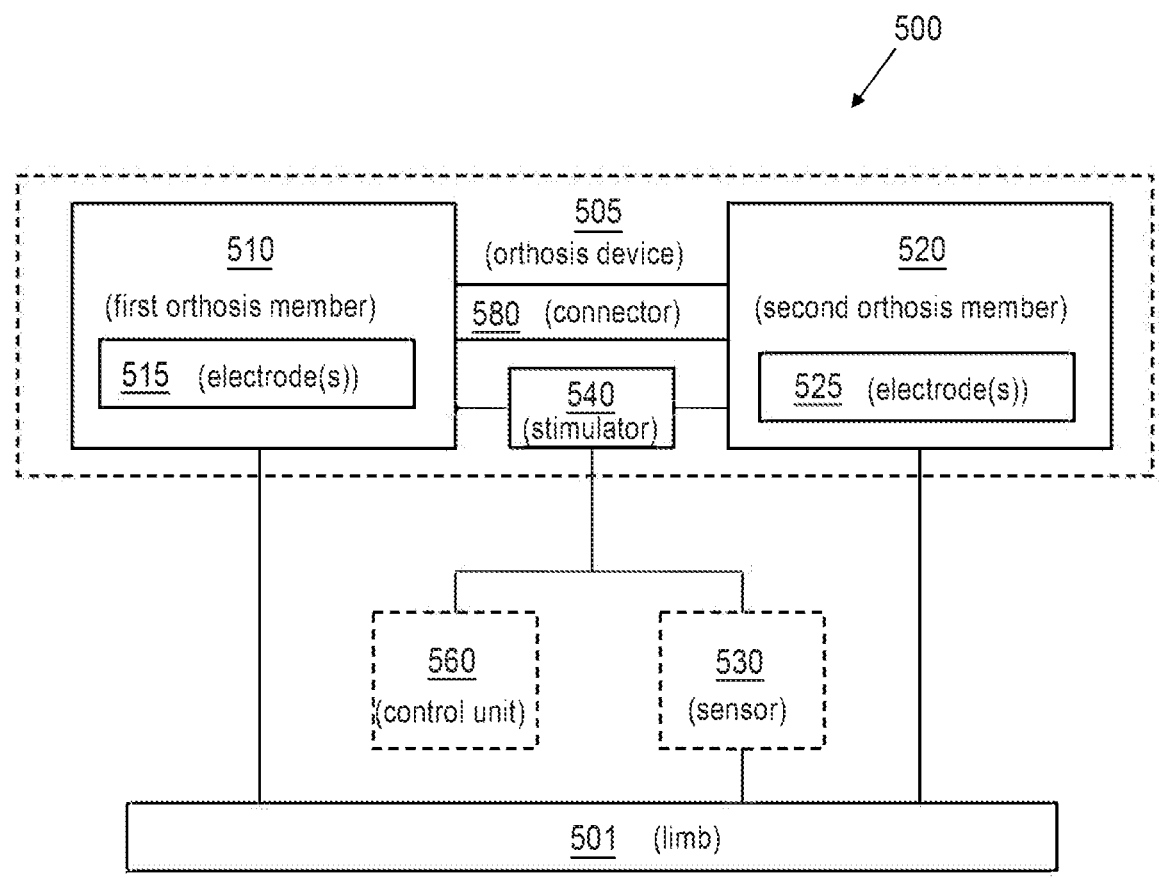
FIG. 47 is a schematic illustration of a system for functional electrical stimulation of a limb according to an embodiment.

Another embodiment of an orthosis system 500 that can be used for the functional electrical stimulation of a target body tissue (e.g., nerve, muscle, ligaments, etc.) is schematically illustrated in FIG. 47. The orthosis system 500 can include an orthosis device 505 and, optionally, a sensor 530 and/or a control unit 560. The orthosis device 505 includes a first orthosis member 510, a second orthosis member 520, a connector 580 and an electric stimulator 540.

The first orthosis member 510 includes one or more electrodes 515 removably couplable to the first orthosis member 512. The second orthosis member 520 includes one or more electrodes 525 removably couplable to the second orthosis member 522. The first orthosis member 510 and the second orthosis member 520 are each configured to be coupled to a limb 501 of a patient such that the one or more electrodes 515 and 525 contact the skin of the patient. For example, the first orthosis member 510 and the second orthosis member 520 can each be coupled to an arm or a leg of the patient. For example, the first orthosis member 510 can be coupled to a first portion of the limb and the second orthosis member 520 can be coupled to a second portion of the limb different from the first portion. The first portion of the limb and second portion of the limb can be spaced apart by a non-zero distance from the first orthosis member.

At least one of the first orthosis member 510 and the second orthosis member 520 can be configured to at least partially envelop the limb 501 of the patient. For example, one or both of the orthosis members 510, 520 can be curved or contoured to be disposed about a portion of the limb 501. In some embodiments, at least one of the orthosis members 510, 520 has a substantially C-shaped cross-sectional profile (e.g., when the cross-section is taken across a horizontal plane). The orthosis members 510, 520 can be formed from any suitable biocompatible materials. In some embodiments, at least one orthosis member 510, 520 is formed from a semi-rigid material such as, for example, a relatively thin metal, a thermoplastic, a polymer, and/or the like, which can enable the orthosis member to provide structural support for the orthosis device 505.

The first orthosis member 510 can be coupled to or otherwise joined with the second orthosis member 520, for example, by a bridge connector 580. In some embodiments, the bridge connector 580 can limit movement of the second orthosis member 522 relative to the first orthosis member 512 along a longitudinal axis of the limb on which the orthosis device 505 is coupled. In some embodiments, the connector 580 can limit movement of the second orthosis member 522 relative to the first orthosis member 512 in a direction along a longitudinal axis of the connector 580. In use, when the orthosis device 505 is donned on the limb of the patient, each of the first orthosis member 510 and the second orthosis member 520 can be extended about the limb of the patient along substantially parallel horizontal axes and the bridge connector 580 can be extended between the first orthosis member 510 and the second orthosis member 520 along a substantially vertical axis.

In some embodiments, the first orthosis member 510 and the second orthosis member 520 can each include a strap configured to secure the orthosis member to the limb of the patient. For the sake of clarity, the strap of the orthosis device 505 is described herein with respect to the first orthosis member 510, however, it should be understood that the strap of the second orthosis member 520 can be similarly configured and/or associated with the second orthosis member 520 in a similar manner. In some embodiments, the strap length is adjustable. In some embodiments, the strap has a fixed, non-adjustable length. The strap can include a first coupling mechanism to couple a first end portion of the strap to the first orthosis member 510. In some embodiments, the first end portion of the strap is releasably coupled to the first orthosis member 510. In some embodiments, the first end portion of the strap is releasably coupled to the first orthosis member 510, and includes a locking mechanism configured to prevent the inadvertent or unintentional release of the first end portion of the strap from the first orthosis member 510. In other embodiments, the first end portion of the strap is fixedly coupled to the first orthosis member 510. The strap can include a second coupling mechanism to releasably couple a second end portion of the strap to the first orthosis member 510.

The electrode(s) 515 and 525 can each be coupled to an interior surface of the panels 512 and 522, respectively, with for example, hook and loop (e.g., Velcro®) patches, press-studs, snaps, magnets, or specialized holders that press a conductive back of the electrode(s) 515 and 525 against a conductive stud or panel inside the orthosis members 510 and 520, or a combination thereof. The electrode(s) 515 and 525 can each make electrical contact with the skin and can include a conductive pad assembly that is held onto a part of the body with the orthosis members 510, 520. In some embodiments, the electrode(s) 515 and/or the electrode(s) 525 can be hydrogel electrodes. In some embodiments, the electrode(s) 515 and/or the electrode(s) 525 can be cloth electrodes. For example, in some embodiments, the electrode(s) 515 and/or electrode(s) 525 can include a metal mesh conductor and an absorbent pad, all of which can be soaked in water. For example, the electrode(s) 515 and/or the electrode(s) 525 can include a pad formed with an absorptive material, such as felt, cloth, velvet, viscose, etc., such that the pad can be saturated with liquid (e.g., water) prior to use. In some embodiments, the electrode(s) 515 and/or the electrode(s) 525 can include a base or panel portion that can be attached to an interior surface of the orthosis 505. In some embodiments, for example, the electrode(s) 515 and/or the electrode(s) 525 can be included in an electrode assembly such that the electrode(s) are fixedly coupled to a panel of the electrode assembly, and the electrode assembly is removably coupleable to the first and/or second orthosis 510, 520, respectively, in a similar manner as described herein with respect to orthosis 1050. The electrode(s) 515 and the electrode(s) 525 can be removably coupled to the first orthosis member 512 and the second orthosis member 522, respectively, such that the electrode(s) 515 and 525 can be easily removed and replaced as needed. The electrode(s) 515 and 525 can be, for example, disposable.

In some embodiments, the electrode(s) 515 can be selectively positioned on the first orthosis member 512 and/or the electrode(s) 525 can be selectively positioned on the second orthosis member 522. For example, the first orthosis member 512 and/or the second orthosis member 522 can include a marking ring indicating where an electrode 515 or 525 is to be positioned for a particular treatment and/or a particular patient. In some embodiments, one or more electrodes 515 and/or 525 can be positioned centered on the first orthosis member 512 and/or the second orthosis member 522. In some embodiments, one or more electrodes 515 and/or 525 can be positioned off-center on the first orthosis member 512 and/or the second orthosis member 522.

The orthosis device 505 can also include a locator (not shown in FIG. 47). At least a portion of the orthosis device 505 can include a locator configured to facilitate proper positioning of the orthosis device 505 with respect to the limb of the patient, as described in more detail herein with reference to embodiments. The locator can be tactile, visual, or any combination thereof. The visual can be for example, a mark, a cutout, a raised element, a recessed element, a separate element coupled to the orthosis device 505, etc. For example, at least one of the first orthosis member 510, second orthosis member 510 or the bridge connector 580 includes an elongate visual locator disposed on the orthosis device 505 along a centerline of the bridge connector 580. The visual locator can be configured, for example, to be substantially aligned with a midline or other predetermined location of the patient's quadriceps and/or hamstrings. In another example, at least one of the first orthosis member 510, second orthosis member 510 or the bridge connector 580 includes a tactile locator disposed on the orthosis device 505 along a centerline of the bridge connector 580. The tactile locator can be, for example, a recessed defined by the portion of the orthosis device 505 or a raised portion of the orthosis device 505. The tactile locator can be configured, for example, to be substantially aligned with a midline or other predetermined location of the patient's quadriceps and/or hamstrings.

The first orthosis member 510 and/or the second orthosis member 520 can include a cradle configured to receive the electric stimulator 540. The electric stimulator 540 can be similar in many respects, or identical to, any electric stimulator described herein (e.g., electric stimulator 140, 1400). In some embodiments, the electric stimulator 540 can be coupled to the cradle with a snap-fit coupling such that the electric stimulator 540 can be removed from the orthosis member as needed. The electric stimulator 540 can be used to generate and send a signal to the electrode(s) 515 and/or the electrode(s) 525 to stimulate a portion of the patient's body. In some embodiments, the electric stimulator 540 can send a signal to the electrode(s) 515 and/or the electrode(s) 525 with a wired connection. For example, the electric stimulator 540 can be operatively connected to the first electrode(s) 515 on the first orthosis member 510 and the connector 580 can include an electrical conductor operatively coupling the first electrode(s) 515 and/or the electric stimulator 540 to the electrode(s) 525 on the second orthosis member 520. In some embodiments, the electric stimulator 540 can communicate with the electrode(s) 515 and/or the electrode(s) 525 with a radio frequency (RF) signal.

The electric stimulator 540 can receive a signal from the control unit 560, the sensor 530, and/or an electric stimulator of a different orthosis device (e.g., a lower leg orthosis device, such as orthosis 105, 1050, described herein) to turn the stimulation on and off. The electric stimulator 540 can receive a signal from the control unit 560, the sensor 530, and/or an electric stimulator of a different orthosis device (e.g., a lower leg orthosis device, such as orthosis 105, 1050, described herein) to indicating a predetermined stimulation program that should be initiated and applied to the electrodes 515, 525. The stimulator 540 can include a rechargeable battery and indicator lights (each not shown in FIG. 47), such as a status light and a stimulation light. The electric stimulator 540 can include a port to receive a charging unit (not shown), such as an AC adapter, to charge a rechargeable battery. The electric stimulator 540 can be configured to emit both visual and audio alerts.

The sensor 530 can be similar in many respects, or identical to, any sensor described herein (e.g., sensor 130, sensor 1300). In some embodiments, the sensor 530 is a gait sensor. The gait sensor 530 can include, for example, a pressure or motion sensor (not shown in FIG. 47) and a transmitter (not shown in FIG. 47) that can communicate wirelessly with the electric stimulator 540. The pressure sensor can detect a heel-off event and a heel-on event. The transmitter can send a signal to the electric stimulator 540 in response to the detecting the heel-off event or heel-on event such that, upon receipt of such signal, the electric stimulator 540 provides an electrical current to the electrodes to provide FES to move the limb (e.g., thigh, knee, foot) accordingly. The sensor 530 can be positioned under the insole of the shoe to be worn by the patient on the affected leg to be treated, and can be attached to a gait sensor pad (not shown in FIG. 47). In some embodiments, the sensor 530 can be positioned under the insole of the shoe on the unaffected leg. The transmitter can be worn clamped to an inner rim of the patient's shoe. The gait sensor 530 can be transferred between different shoes (e.g., different styles, right or left). The gait sensor 530 can be powered with, for example, a non-rechargeable or disposable battery. Other examples of a gait sensor that can be used with the orthosis system 100 are described, for example, in U.S. Pat. No. 7,632,239, which is incorporated herein by reference in its entirety.

In one example use, the orthosis device 505 can be disposed about a first portion of a thigh of a patient such that the electrode(s) 515 on the first orthosis member 510 and the electrode(s) 525 on the second orthosis member 520 can each stimulate a different portion of a hamstring muscle of the patient. The patient can reposition the orthosis 120 on the thigh such that the electrode(s) 515 on the first orthosis member 510 and the electrode(s) 525 on the second orthosis member 520 can each stimulate a different portion of the thigh. For example, the orthosis 120 can be disposed about a first portion of a thigh of a patient such that the electrode(s) 515 on the first orthosis member 510 and the electrode(s) 525 on the second orthosis member 520 can each stimulate a different portion of a quadriceps muscle or quadriceps muscle group and/or the nerves associated with those muscles of the patient. In another example, both the first orthosis member 510 and the second orthosis member 520 can both be configured to stimulate different portions of a hamstring muscle or the nerves associated with the hamstring muscle.

FIGS. 48-65 illustrate a system 5000 including an orthosis device 5050 according to an embodiment. The orthosis device 5050 includes a first orthosis member 5100, a second orthosis member 5200, a bridge connector 5800 and a stimulator unit 5400. The first orthosis member 5100, the second orthosis member 5200 and the bridge connector 5800 collectively form a frame assembly 5055 of the orthosis 5050. As described herein with respect to other orthosis devices (e.g., orthosis 105, 1050, orthosis device 500), the orthosis device 5050 can be used to provide electrical stimulation to a portion of a limb of a patient, such as for example, an arm or a leg of the patient. For example, the orthosis 5050 can be configured to provide electrical stimulation to the leg of the patient resulting in knee flexion and/or knee extension. In some embodiments, the orthosis device 5050 can be disposed on a thigh of a patient such that the first orthosis member 5100 is disposed at a first distance from the knee of the patient and the second orthosis member 5200 is disposed at a second distance from the knee that is greater than the first distance.

Figure 48:
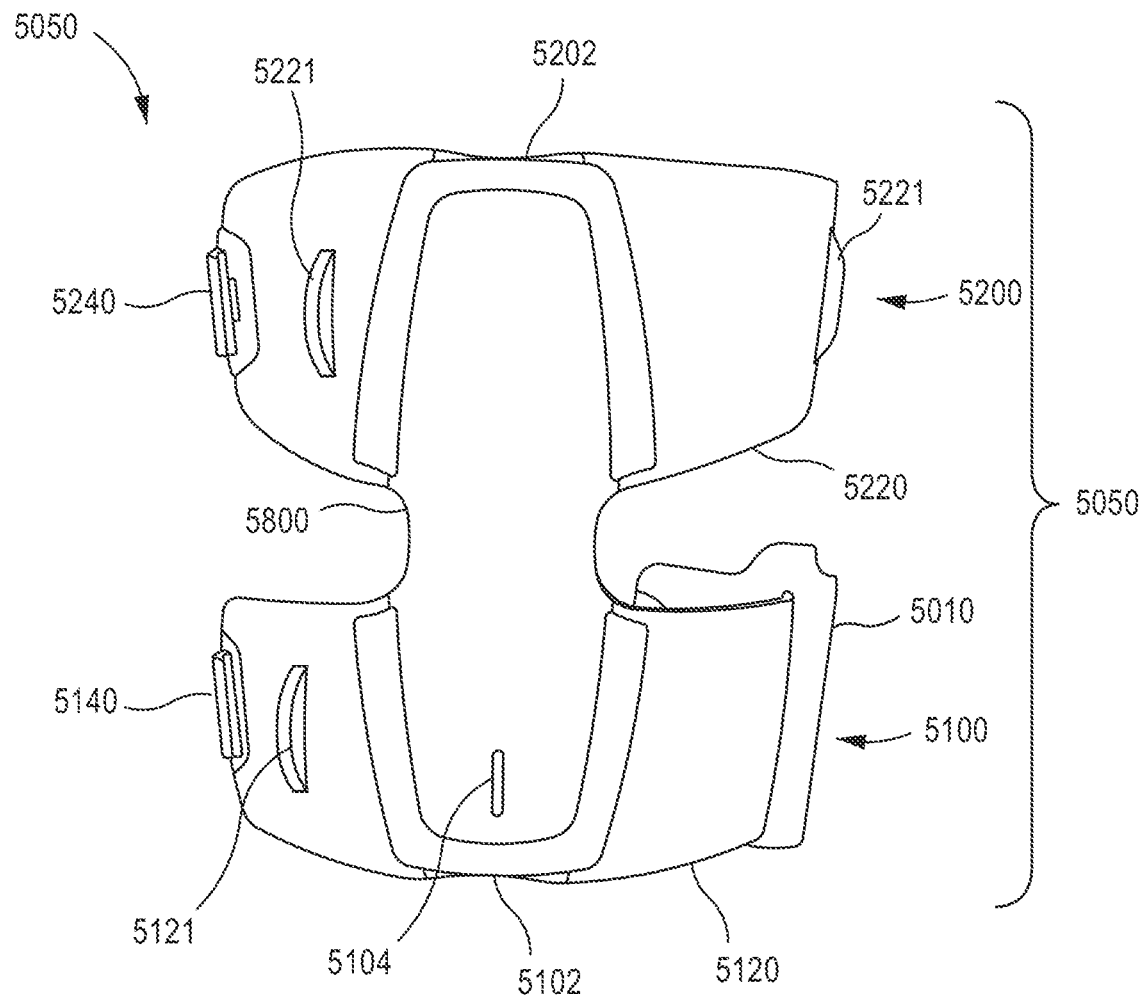
FIG. 48 is a front view of a portion of an orthosis according to an embodiment.
Figure 50:
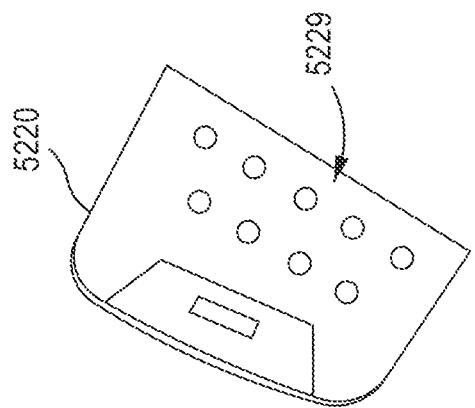
FIG. 50 is an enlarged view of a portion of the orthosis of FIG. 49.
Figure 49:
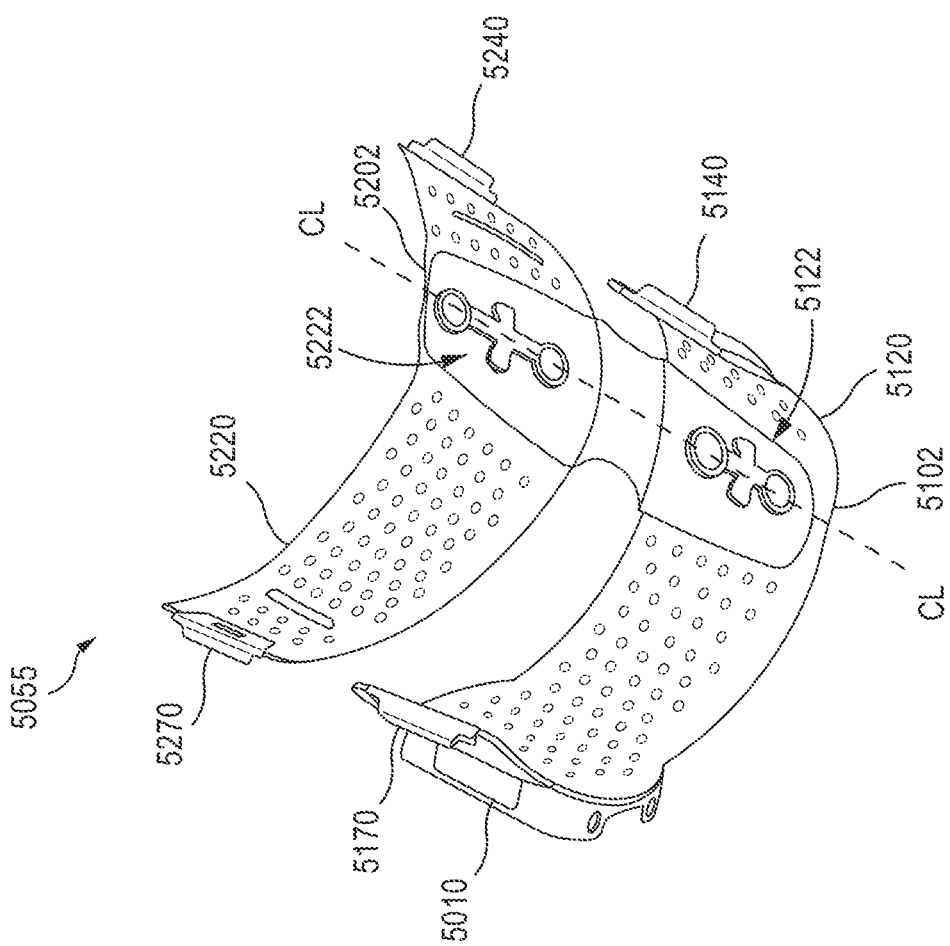
FIG. 49 is a perspective rear view of the orthosis of FIG. 48.

The first orthosis member 5100 includes a first panel or cuff 5120 and the second orthosis member 5200 includes a second panel or cuff 5220. The bridge connector 5800 couples the first orthosis member 5100 to the second orthosis member 5200, and more specifically couples the first cuff 5120 to the second cuff 5220. As shown in FIGS. 48-50, the bridge connector 5800 is fixedly coupled to each of the first orthosis member 5100 and the second orthosis member 5200. As such, a distance between the first orthosis member 5100 and the second orthosis member 5200 is fixed. In other words, the first orthosis member 5100 is spaced apart from the second orthosis member 5200 by a predetermined distance, and thus a first electrode 5150 associated with the first orthosis member 5100 and a second electrode 5250 associated with the second orthosis member are spaced apparat by a predetermined (or fixed) distance. In some embodiments, an inner surface of at least one of the first cuff 5120 or the second cuff 5220 includes a textured or contoured portion configured to prevent movement of the orthosis device 5050 with respect to the limb of the patient. For example, as shown in FIG. 50, the second cuff 5220 defines a set of concave recesses or pores 5229. The pores 5229 help to create friction between the second cuff 5220 and the skin of the patient, and thus help to prevent movement of the orthosis device 5050 with respect to the patient's limb (e.g., to prevent slippage of the orthosis 5050 during use).

Figure 52:
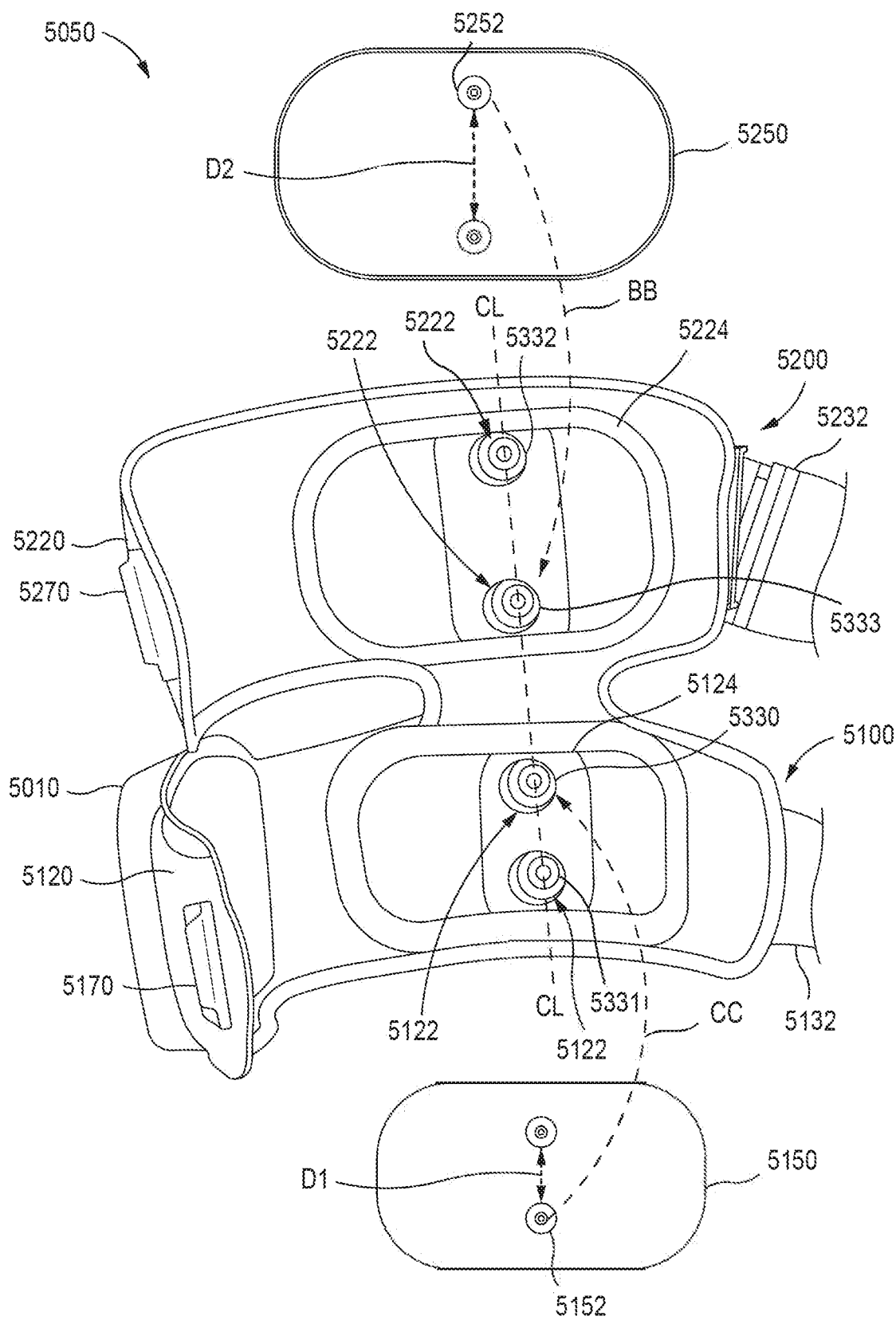
FIG. 52 is a rear view of a portion of an FES system according to an embodiment including the orthosis of FIG. 48, a housing, and electrodes according to an embodiment.

The first orthosis member 5100 includes a first set of electrode connectors 5122 which can include connectors 5330, 5331, and the second orthosis member 5200 includes a second set of electrode connectors 5222, which can include connectors 5332, 5333. Each set of electrode connectors 5122, 5222 is substantially aligned or centered with a centerline CL of the bridge connector 5800, as shown in FIG. 50. In other embodiments, however, at least one electrode connector can be offset from the centerline of the bridge connector. As shown in FIG. 52, a first electrode 5150 can be removably coupled to an inner surface of the first cuff 5120 via the first set of electrode connectors 5122 (e.g., by turning over the first electrode 5150 in the direction of arrow CC shown in FIG. 52 to connect the connectors 5152 of the first electrode 5150 with the connectors 5330, 5331, respectively, of the first orthosis member 5100) and a second electrode 5250 can be removably coupled to an inner surface of the second cuff 5220 via the second set of electrode connectors 5222 (e.g., by turning over the second electrode 5250 in the direction of arrow BB shown in FIG. 52 to connect the connectors 5252 of the second electrode 5250 with the connectors 5332, 5333 of the second orthosis member 5200). In some embodiments, the orthosis members 5100, 5200 and the bridge member 5800 define one or more inner or recessed channels (not shown) between the electrode connectors 5122, 5222 and the connectors of the cradle 5010, such that wires or the like can be disposed in the channels for electronically coupling the electrode connectors 5122, 5222 to the stimulator 5400 via the cradle.

The first orthosis member 5100 and the second orthosis member 5200 are each configured to be coupled to a limb of a patient such that the first electrode 5150 and the second electrode 5250 can each contact the skin of the patient. The first electrode 5150 and the second electrode 5250 can each be any suitable electrode described herein. For example, For example, at least one of the electrodes 5150, 5250 can include a metal mesh conductor and an absorbent pad, all of which can be soaked in water. For example, at least one of the electrodes 5150, 5250 can include a pad formed with an absorptive material, such as felt, cloth, velvet, viscose, etc., such that the pad can be saturated with liquid (e.g., water) prior to use. In another example, at least one of the first electrode 5150 or the second electrode 5250 can be a hydrogel electrode.

Figure 53:
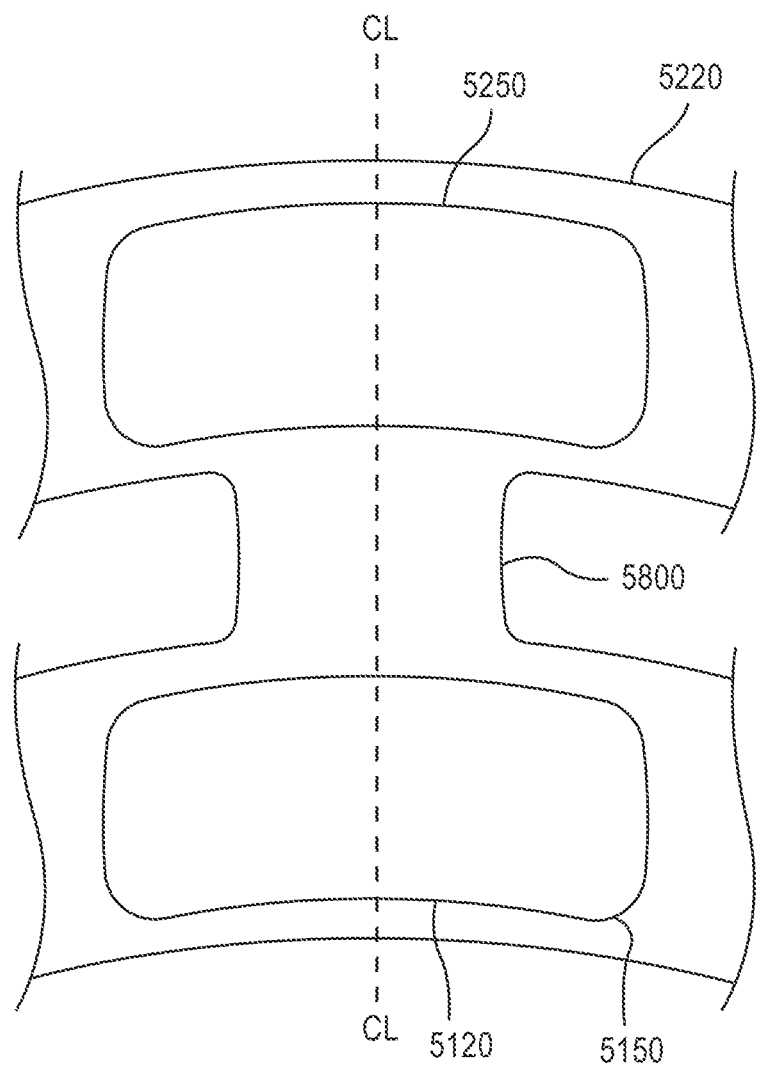
FIG. 53 is a perspective view of the portion of the FES system of FIG. 52 with the electrodes coupled to the orthosis according to an embodiment.

The first electrode 5150 and the second electrode 5250 are each substantially aligned or centered with a centerline CL of the bridge connector 5800 as shown in FIG. 53 when coupled to the sets of electrode connectors 5122, 5222, respectively. Each electrode 5150, 5250 has a width greater than a length of the electrode and defines a centerline that can be substantially aligned or centered with the centerline CL of the bridge connector 5800 when coupled to the respective cuff 5120, 5220. The first electrode 5150 and the second electrode 5250 can each be removably coupled to the first cuff 5120 and the second cuff 5220, respectively, with a snap-fit connection, as shown in FIGS. 52-53. The snap-fit connectors (also referred to herein as "snaps") 5152, 5252 of the electrodes 5150, 5250 are centered with respect to the width of the electrode and vertically arranged with respect to the height of the electrode such that the snap-fit connectors are substantially aligned or centered with the centerline CL of the bridge connector 5800, thus enabling the electrode 5150, 5250 alignment with respect to the bridge connector 5800 described above.

In some embodiments, the snap-fit connectors 5152, 5252 are sized to enhance the stability of the snap-fit connection. For example, one or more of the snap-fit connectors 5152, 5252 can have a diameter of 4.2 mm, which provides for greater stability of the snap-fit connection, than, for example, that provided by a snap-fit connector having a diameter of 3.96 mm.

Figures 54, 55:
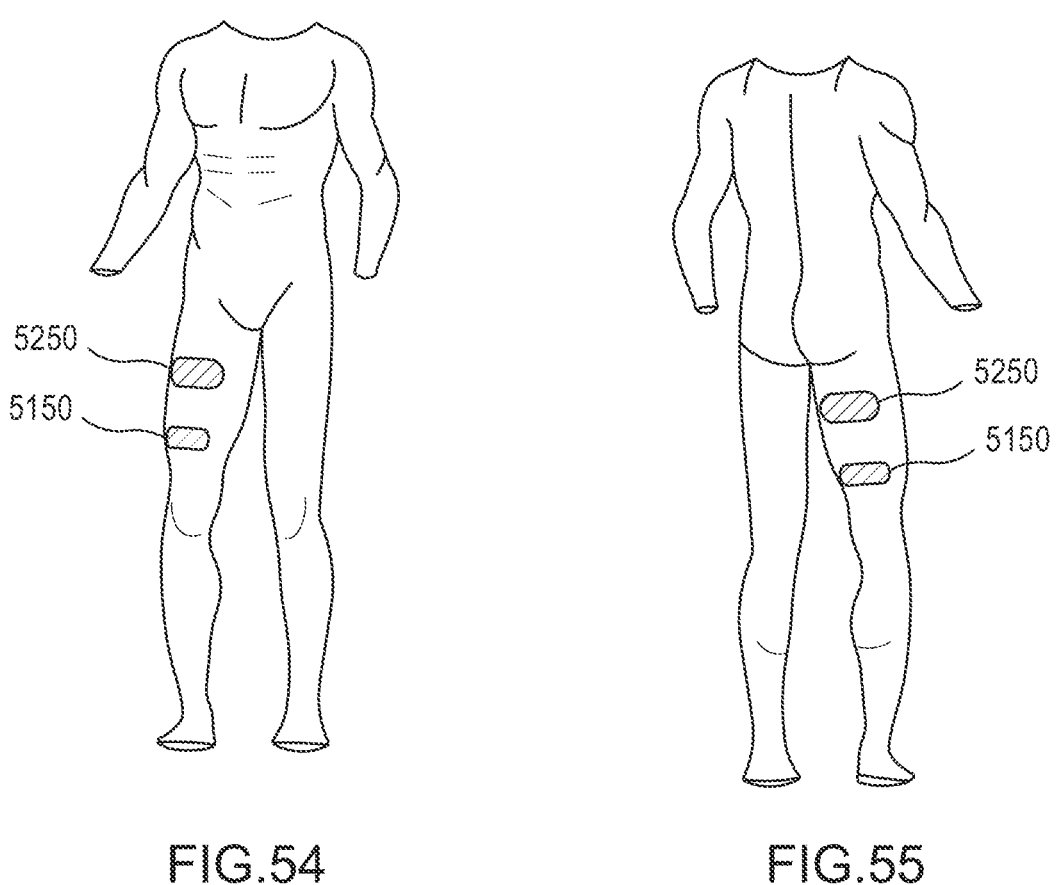
FIGS. 54-55 are front and rear views of a patient with electrodes disposed in a first configuration and a second configuration, respectively.

In some embodiments, the snap-fit connections may be uniquely shaped or sized to ensure the use of the appropriate electrodes. For example, as shown in FIG. 52, the male snap connectors 5152 of the first electrode 5150 are spaced apart by a predetermined distance D1, and the male snap connectors 5252 of the second electrode 5250 are spaced apart by a predetermined distance D2 different than the predetermined distance D1. For example, the distance D1 between the snap connectors 5152 of the first electrode 5150 is less than the distance between the snap connectors 5252 of the second electrode 5250. The female snap connectors of the corresponding set of electrode connectors 5122, 5222, respectively, are spaced apart by corresponding predetermined distances. In this manner, the electrode connectors 5122, 5222 of orthosis 5050 are configured to ensure the correct electrode 5150, 5250, respectively, is placed on the correct cuff 5120, 5220, respectively. As discussed herein, the orthosis 5050 is configured to be coupled to the limb of the patient in at least two positions, such as for stimulation of the quadriceps muscles or the hamstring muscles. As such, coupling of the electrodes 5150, 5250 to the cuffs 5120, 5220, respectively, helps to ensure proper placement of the electrodes with respect to the target tissue, for example, as shown in FIG. 54 (for the quadriceps muscles) and FIG. 55 (for the hamstring muscles).

In some embodiments, each of the snap-fit connectors can be different shapes to ensure the correct electrode is placed on the correct cuff. In some embodiments, at least one of the first cuff 5120 or the second cuff 5220 can include a locator marking (not shown) on one of the electrode connectors 5122, 5222, and the corresponding electrode 5150, 5250 can include a corresponding marking (not shown) disposed on the snap connector 5152, 5252, which collectively indicate to the user the correct electrode placement with respect to the correct cuff.

Although the electrodes 5150, 5250 are shown and described herein as being substantially centered with respect to the centerline CL of the bridge connector 5800, in other embodiments at least one of the first electrode 5150 or the second electrode 5250 can be disposed offset from the centerline CL defined by the bridge connector 5800. Said another way, although the electrode connectors 5122, 5222 are shown and described with respect to FIG. 52 as being are centered, and thus the electrodes 5150, 5250 can only be oriented in a centered position, it should be understood that in some embodiments, at least one of the electrode connectors or the snap connectors on the corresponding electrodes can be differently configured or positioned to allow for different or offset positioning of the at least one electrode with respect to its corresponding cuff and/or the bride connector 5800. In some embodiments, multiple electrode connectors may be provided on each of the cuffs 5120, 5220 to provide for multiple possible orientations of the electrodes 5150, 5250.

The orthosis device 5050 can also include a set of locators configured to facilitate proper positioning of the orthosis device 5050 with respect to the limb of the patient, as described in more detail herein. Referring to FIGS. 48-51, the first orthosis member 5100 includes a first locator 5102 configured to provide a tactile indication to the user indicative of the centerline CL of the bridge connector 5800. As shown, the first locator 5102 is formed by a recess or concavity along an edge (e.g., a distal edge) of the first cuff 5120. The first locator 5102 is configured to be aligned with a predetermined location of the patient's anatomy (e.g., a midline of the limb with respect to the quadriceps and/or hamstrings, proximally about a portion of the patella, or the like). The second orthosis member 5200 includes a second locator 5202 that substantially mirrors the first locator 5102, and is configured to provide a tactile indication to the user indicative of the centerline of the bridge connector 5800. The second locator 5202 is formed by a recess or concavity along an edge (e.g., a proximal edge) of the second cuff 5220. The second locator 5202 is configured to be aligned with a predetermined location of the patient's anatomy (e.g., a midline of the limb with respect to the quadriceps and/or hamstrings). A third locator 5104 is disposed along the centerline CL of the bridge member 5800. As shown in FIG. 48, the third locator 5104 is configured to provide a visual indication of the position of the orthosis 5050. The third locator 5104 is an elongate marking substantially aligned with the centerline CL of the bridge member 5800, however, in other embodiments, the visual locator can have a different shape or be differently positioned with respect to the orthosis 5050.

The first orthosis member 5100 includes a first strap assembly 5130 and the second orthosis member 5200 includes a second strap assembly 5230. The first strap assembly 5130 includes a strap member 5132 and the second strap assembly 5230 includes a strap member 5232 as shown, for example, in FIG. 57. Coupling members 5134, 5234 are coupled to first end portions of the first strap member 5132 and the second strap member 5232, respectively, and are configured to couple the strap members 5132, 5232 to the cuffs 5120, 5220, respectively, as described herein. The coupling member 5134, 5234 and its respective strap member 5132, 5134 can be coupled via any suitable mechanism including, for example, an adhesive, a weld, a resistance fit, or the like, or any combination thereof.

A retaining member 5140 is coupled to the first end of the first cuff 5120. The retaining member 5140 includes a protrusion 5141 defining a channel 5142 that is open towards the first cuff 5120 (or in a direction away from the strap member 5132). The channel 5142 of the retaining member 5140 is configured to matingly receive at least a portion of the coupling member 5134 of the first strap assembly 5130 therein. The retaining member 5140 of the first cuff 5120 defines an elongate aperture or slot 5143 in fluid communication with the channel 5142. In some embodiments, the slot 5143 extends through the retaining member 5140 to an inner surface (e.g., a surface facing the patient's body when the orthosis 5050 is donned on the limb) of the retaining member 5140 of the first cuff 5120. The slot 5143 is configured to receive a nub 5135 of the coupling member 5134 such that the nub 5135 engages a portion of the retaining member 5140 defining the slot 5143.

In use, the coupling member 5134 of the first strap assembly 5130 is disposed about the retaining member 5140 of the first cuff 5120 such that the protrusion 5142 of the retaining member 5140 is received in an opening 5136 defined by the coupling member 5134, such that a portion of the coupling member 5134 is received in the channel 5142 of the retaining member 5140, and such that the nub 5135 is received in the slot 5143. The foregoing configuration is configured to couple the strap member 5132 of the first strap assembly 5130 to the first end of the first cuff 5120 such that the coupling member 5134 of the first strap assembly can be selectively uncoupled from the retaining member 5140, but such that inadvertent decoupling therebetween is substantially prevented. In other words, the coupling between the coupling member 5134 of the first strap assembly 5130 and the retaining member 5140 of the first cuff 5120 must be overcome by an amount of force and/or angle of movement that is greater than that encountered during normal use of the orthosis (e.g., greater than shear forces encountered during a gait event). As such, while the coupling member 5134 of the first strap assembly 5130 is configured to be releasable from the retaining member 5140 of the first cuff 5120, it is also configured to not be unintentionally disconnected therefrom. In other embodiments, however, the coupling member 5134 of the first strap assembly 5130 can be fixedly coupled to the retaining member 5140 of the first cuff 5120.

Similarly, a retaining member 5240 is coupled to a first end of the second cuff 5220. The retaining member 5240 includes a protrusion 5241 defining a channel (not shown) that is open towards the second cuff 5220. The channel 5242 is configured to matingly receive at least a portion of the coupling member 5234 of the strap member 5232 of the second strap assembly 5230 therein. The retaining member 5240 defines an elongate aperture or slot (not shown) in fluid communication with the channel. In some embodiments, the slot extends through the retaining member 5240 to an inner surface (e.g., a surface facing the patient's body when the orthosis 5050 is donned on the limb) of the retaining member 5240. The slot is configured to receive a nub (not shown) of the coupling member 5234 such that the nub engages a portion of the retaining member 5240 defining the slot.

In use, the coupling member 5234 of the strap member 5232 of the second strap assembly 5230 is disposed about the retaining member 5240 of the second cuff 5220 such that the protrusion 5242 of the retaining member 5240 is received in an opening 5236 defined by the coupling member 5234, such that a portion of the coupling member 5234 is received in the channel 5242 of the retaining member 5240, and such that the nub is received in the slot. The foregoing configuration is configured to couple the strap member 5232 of the second strap assembly 5230 to the first end of the second cuff 5220 such that the coupling member 5234 can be selectively uncoupled from the retaining member 5240, but such that inadvertent uncoupling is substantially prevented. In other words, the coupling between the coupling member 5234 of the strap member 5232 and the retaining member 5240 of the first cuff 5220 must be overcome by an amount of force and/or angle of movement that is greater than that encountered during normal use of the orthosis 5050 (e.g., greater than shear forces encountered during a gait event). As such, while the coupling member 5234 is configured to be releasable from the retaining member 5240, it is also configured to not be unintentionally disconnected therefrom. In other embodiments, however, the coupling member 5234 can be fixedly coupled to the retaining member 5240.

Figure 57:
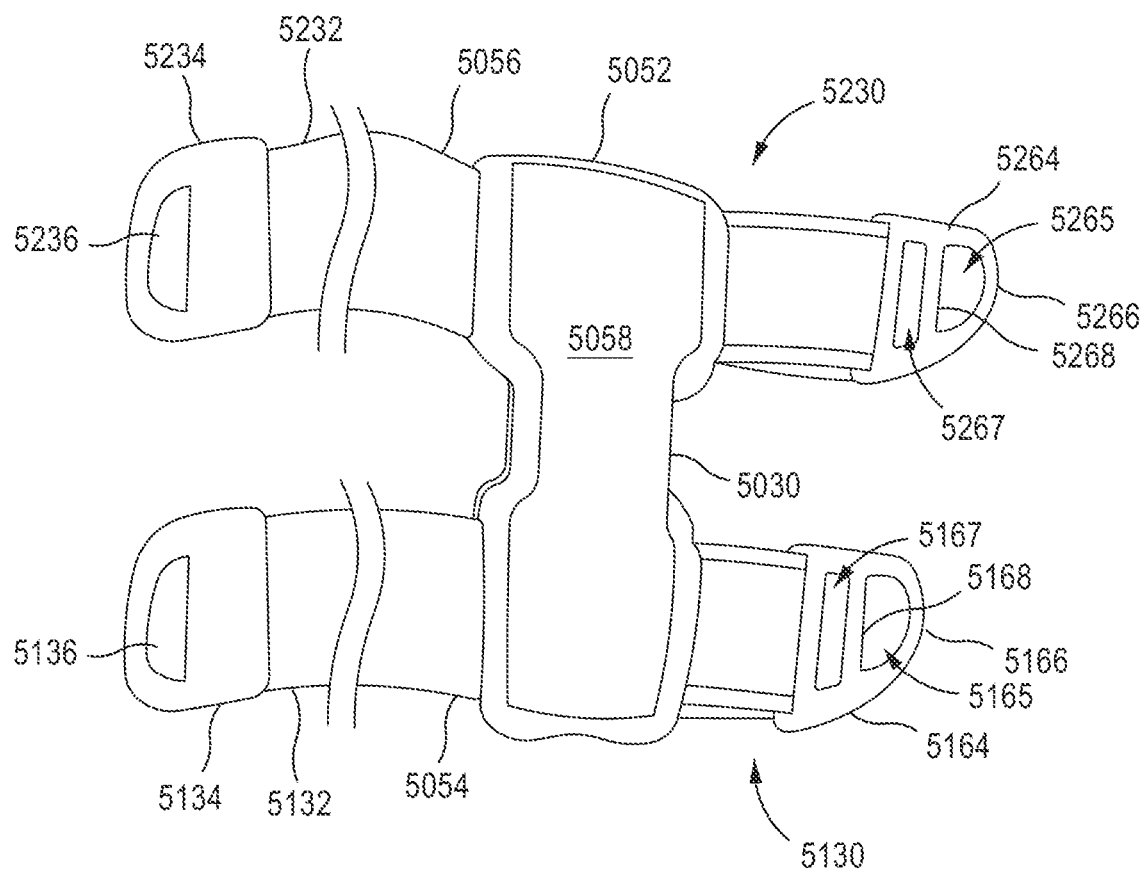
Figure 58:
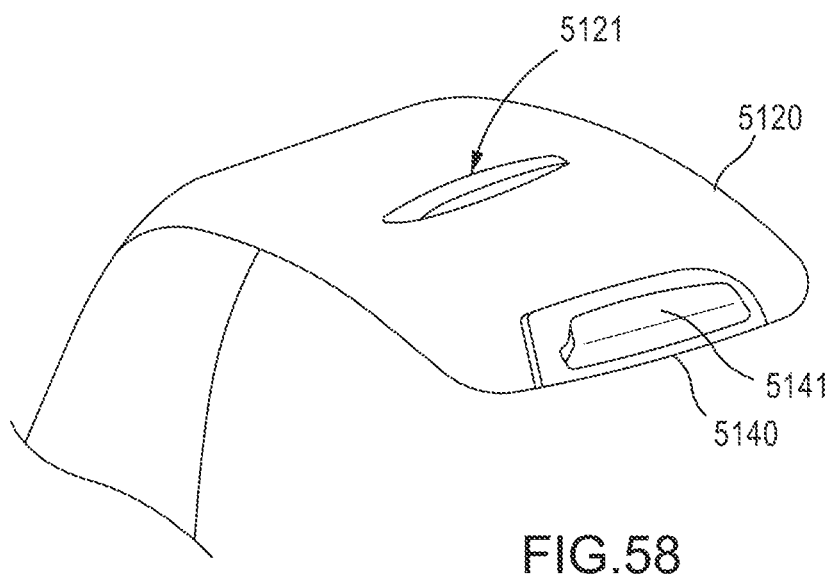
Figure 59:
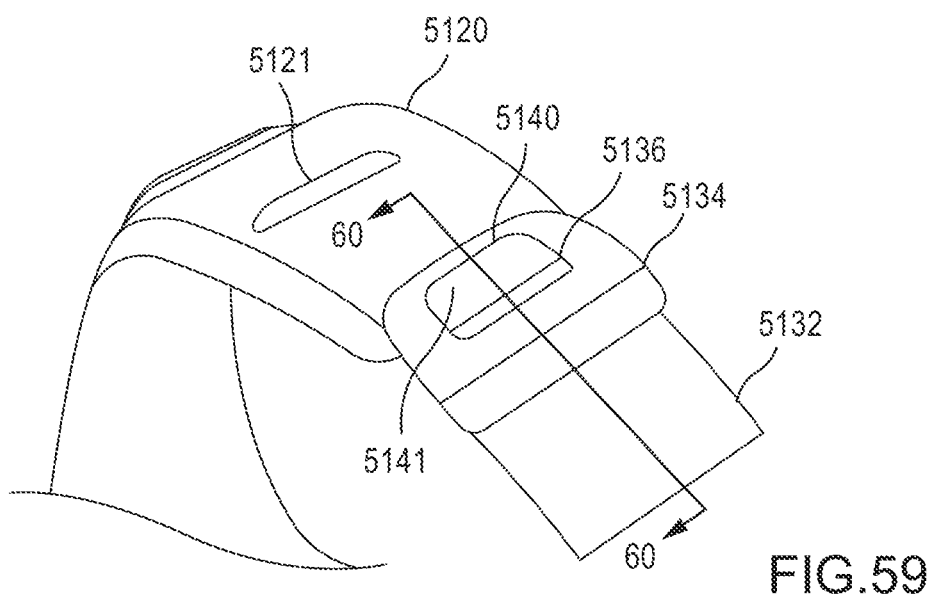
Figure 60:
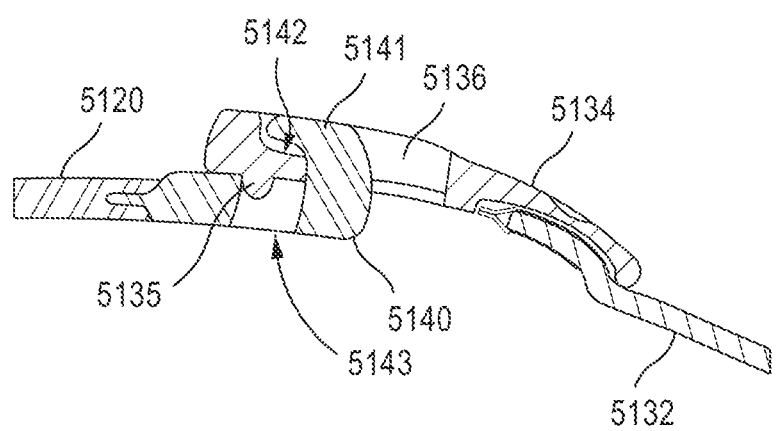
Figure 61:
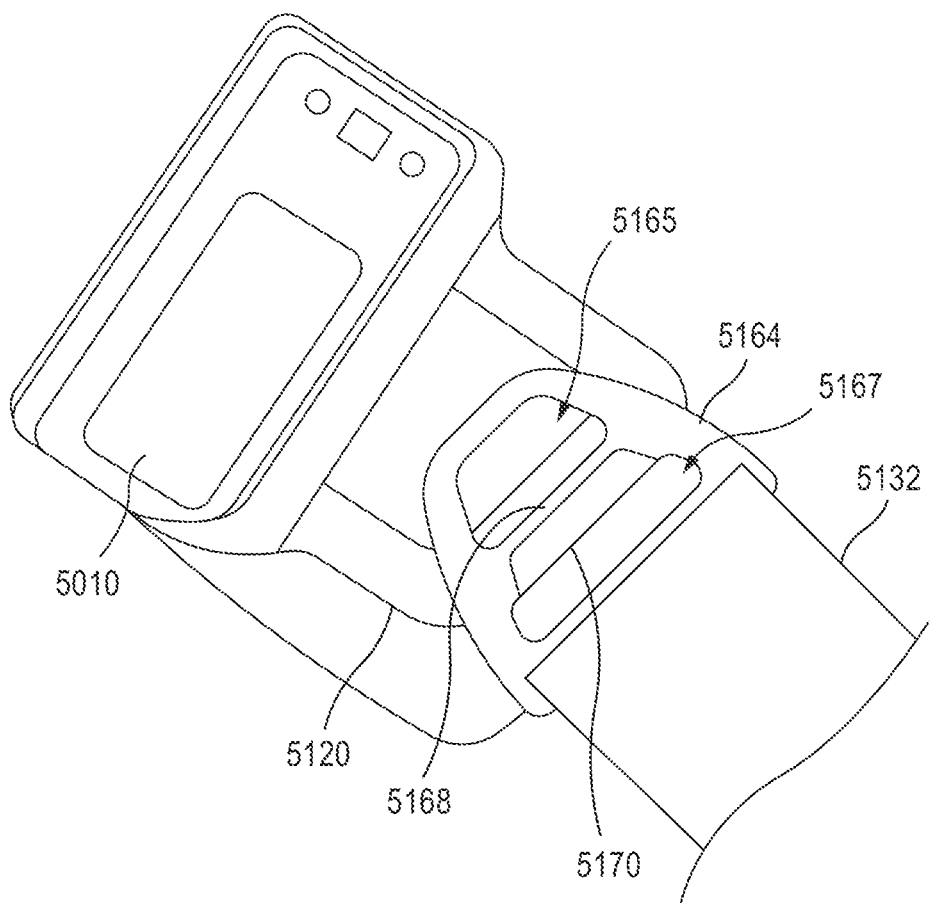

As shown in FIG. 57, buckles 5164, 5264 are coupled to second end portions of the first strap member 5132 and the second strap member 5232, respectively, and are configured to couple the strap members 5132, 5232 to second end portions of the first cuff 5120 and second cuff 5220, respectively, as described herein. Each buckle 5164, 5264 and its respective strap member 5132, 5134 can be coupled via any suitable mechanism including, for example, an adhesive, a weld, a resistance fit, or the like, or any combination thereof.

Figure 62:
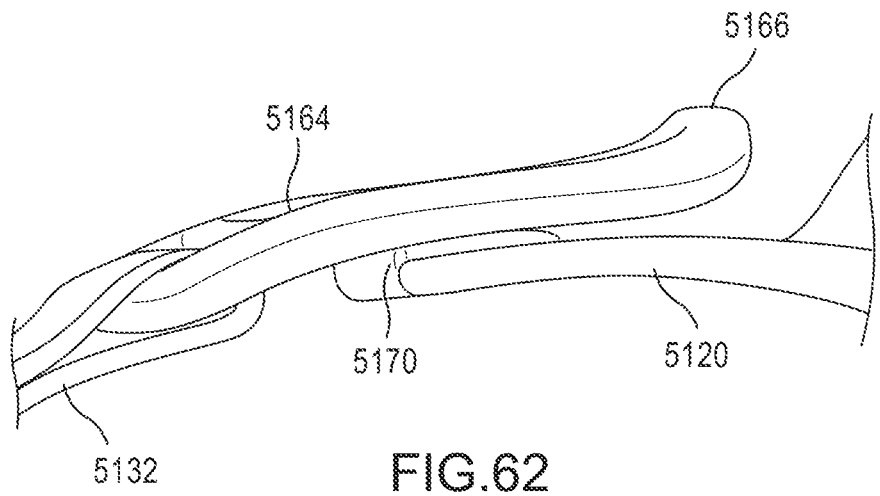

Retaining members 5170, 5270 are coupled to second end portions of the first cuff 5120 and the second cuff 5220, respectively (see, e.g., FIG. 50). The retaining members 5170, 5270 can have similar features and/or function as the retaining member 5140, 5240 described above. The retaining member 5170 of the first cuff 5120 defines a channel (not shown) that is open towards the cuff 5120 (or in a direction away from the strap member 5132 coupled thereto). The channel of the retaining member 5170 is configured to matingly receive at least a portion of the buckle 5164 therein. For example, the buckle 5164 can include an elongate member 5168 disposed across the buckle 5164 between a first opening 5165 defined by the buckle 5164 and a second opening 5167 defined by the buckle. Referring to FIG. 57, the first opening 5165 is shown as being defined between the elongate member 5168 and an end portion 5166 of the buckle 5164. The buckle 5164 can be at least partially disposed about the retaining member 5170 such that at least a portion of the retaining member 5170 is disposed within the second opening 5167 of the buckle 5164 and such that the elongate member 5168 is at least partially disposed in the channel defined by the retaining member 5170 of the second end of the first cuff 5120 (see, e.g., FIG. 61). In this manner, the buckle 5164 is configured to be coupled to the retaining member 5170, and thus the first strap member 5130 can be coupled to the second end of the first cuff 5120. In some embodiments, as shown in FIG. 62, the buckle 5164 and the retaining member 5170 collectively define a low profile, which helps to prevent the inadvertent decoupling of the buckle 5164 during use. The buckle 5264 associated with the second strap member 5230 and its respectively retaining member 5270 can similarly define a low profile.

Similarly, the retaining member 5270 of the second cuff 5220 defines a channel (not shown) that is open towards the cuff 5220 (or in a direction away from the strap member 5232 coupled thereto). The channel of the retaining member 5270 is configured to matingly receive at least a portion of the buckle 5264 therein. For example, the buckle 5264 can include an elongate member 5268 disposed across the buckle 5264 between a first opening 5265 defined by the buckle 5264 and a second opening 5267 defined by the buckle. Referring to FIG. 57, the first opening 5265 is shown as being defined between the elongate member 5268 and an end portion 5266 of the buckle 5264. The buckle 5264 can be at least partially disposed about the retaining member 5270 such that at least a portion of the retaining member 5270 is disposed within the second opening 5267 of the buckle 5264 and such that the elongate member 5268 is at least partially disposed in the channel defined by the retaining member 5270 of the second end of the first cuff 5220. In this manner, the buckle 5264 is configured to be coupled to the retaining member 5270, and thus the second strap member 5230 can be coupled to the second end of the second cuff 5220. In some embodiments, the buckle 5264 and the retaining member 5270 collectively define a low profile, which helps to prevent the inadvertent decoupling of the buckle 5264 during use, in a similar manner as that described above with respect to buckle 5164. In this manner, the buckles 5164, 5264 are configured to reversibly couple the strap members 5130, 5230 to the second end portions of the cuffs 5110, 5120.

In some embodiments, the first cuff 5120 includes a grip feature 5121 disposed proximate at least one of the retaining members 5140, 5170 to facilitate coupling of the coupling member 5134 and/or the buckle 5164, respectively, to its respective retaining member 5140, 5170. Similarly, in some embodiments, the second cuff 5220 includes a grip feature 5221 disposed proximate at least one of the retaining member 5240, 5270 to facilitate coupling of the coupling member 5234 and/or the buckle 5264, respectively, to its respective retaining member 5240, 5270.

Figure 63:
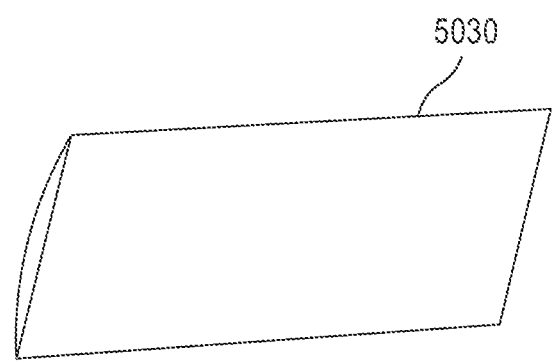

At least one of the first strap assembly 5130 and the second strap assembly 5230 can be adjustable such that the orthosis device 5050 can be adjustably sized to fit a particular limb and/or particular patient. For example, in some embodiments, a length of the strap member 5132 is adjustable with respect to the buckle 5164 of the first strap assembly 5130 and/or a length of the strap member 5232 is adjustable with respect to the buckle 5264 of the second strap assembly 5230. In some embodiments, the length of at least one strap member 5132, 5232 is fixed. In some embodiments, strap assemblies are available in various lengths, and one or more strap assemblies are chosen based on the anatomy of a particular patient. For example, a kit can include one, two, three, four or more strap assemblies each having a different length, such that one of the strap assemblies of the kit can be selected for use with a particular patient. In some embodiments, at least one strap assembly 5130, 5230 includes a strap cover, as shown in FIG. 63. The strap cover 5030 is configured to be disposed about at least a portion of a strap member 5132, 5232. The strap cover 5030 can be made of any suitable material. In some embodiments, the strap cover 5030 has a length that is greater than its width. In some embodiments, the strap cover 5030 has a width of about 60 mm.

Figure 56:
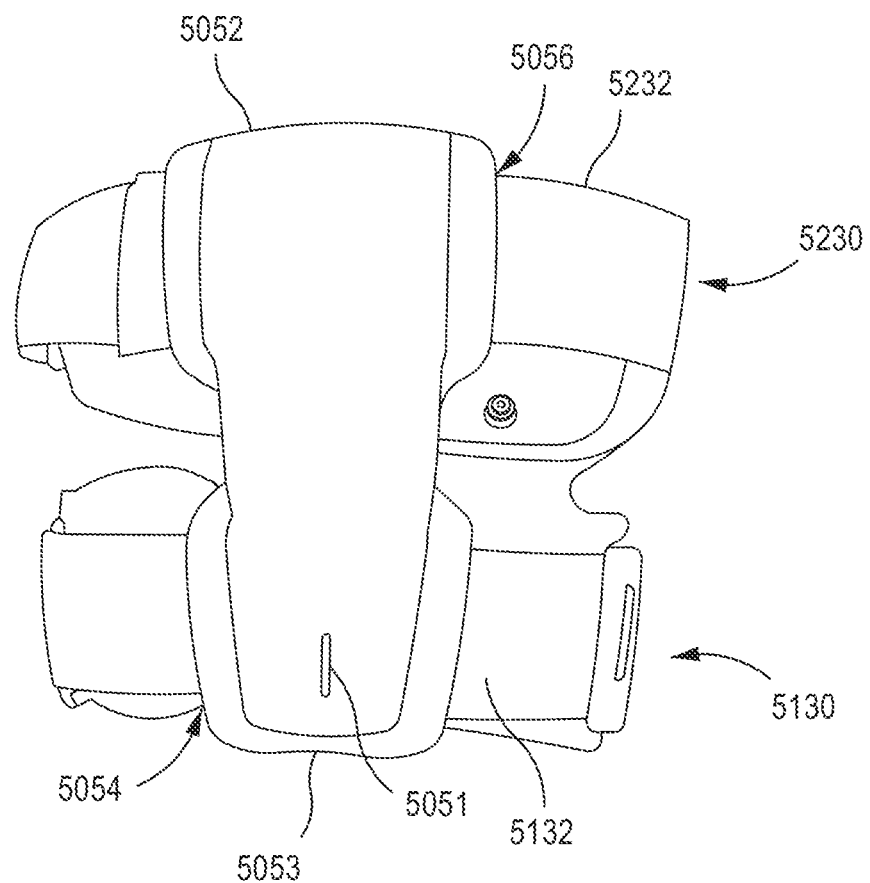
FIGS. 56-63 are various views of portions of strap assemblies of the orthosis of FIG. 48 according to embodiments.

As shown in FIGS. 56 and 57, the orthosis 5050 can include a strap holder 5052. The strap holder 5052 defines a first passageway 5054 through which at least a portion of the first strap member 5132 can be disposed, and a second passageway 5056 through which at least a portion of the second strap member 5232 can be disposed. As such, the strap holder 5052 is configured to maintain the portion of the first strap member 5132 spaced apart from the portion of the second strap member 5232. Said another way, the strap holder 5052 is configured to maintain a minimum distance between portions of the strap members 5132, 5232 of the first and second cuffs 5120, 5220, respectively, and a maximum distance between the portions of the strap members 5132, 5232 of the first and second cuffs 5120, 5220, respectively. The strap holder 5052 is configured to disburse a pressure applied by the strap members 5132, 5232 across the surface area of the strap holder 5052, and thus reduces the amount of direct pressure produced by the strap members 5132, 5232 on the limb. An inner surface 5058 of the strap holder 5052 can be configured to help resist movement (e.g., slipping or sliding) of the strap members 5132, 5232 with respect to the limb of the patient. For example, in some embodiments, the inner surface 5058 includes silicone disposed thereon to help maintain the position of the strap holder 5052, and thus the strap members 5132, 5232, with respect to the limb. In some embodiments, the strap holder 5052 can include a locator (e.g., visual and/or tactile) to facilitate proper placement of the orthosis 5050 with respect to the limb. For example, the strap holder 5052 can include a visual locator 5051 in the form of an elongate marking, or any other suitable visual element, indicative of a centerline of the strap holder 5052. In another example, the strap holder 5052 can include a tactile locator 5053 in the form of a contour or recess, or any other suitable tactile element, indicative of a centerline of the strap holder.

Figure 64:
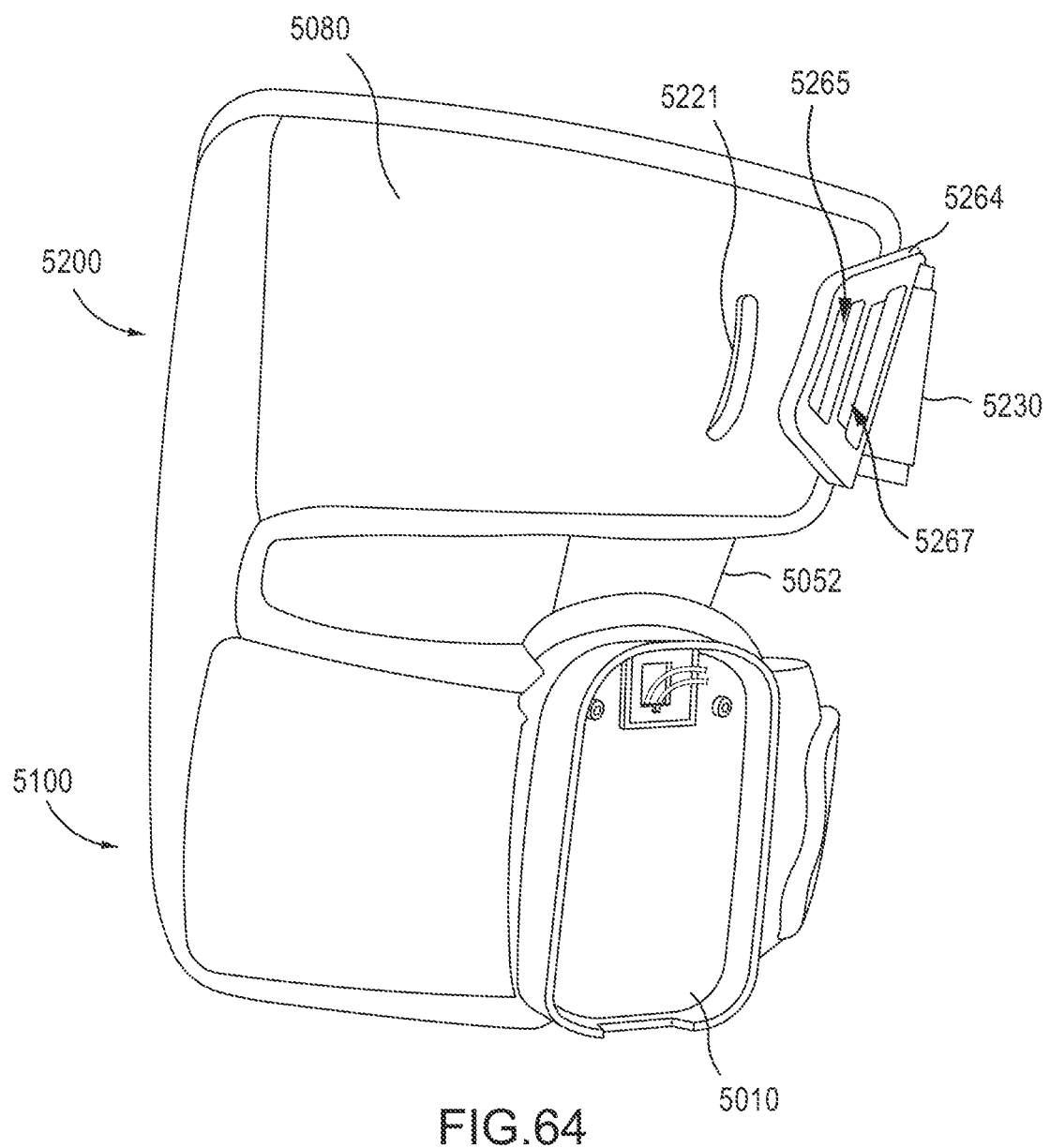
FIG. 64 is a side view of the orthosis of FIG. 48 with a housing disposed thereon.

In some embodiments, as shown in FIG. 64, the orthosis 5050 includes a housing 5080 configured to be disposed on at least a portion of the first orthosis member 5100, the second orthosis member 5200 and/or the bridge connector 5800. For example, at least a portion of each of the first cuff 5120 and the second cuff 5130 can be disposed within the housing 5080, such as between a first layer of the housing and a second layer of the housing. The housing 5080 can be configured to improve patient comfort when wearing the orthosis 5050. For example, the housing 5080 can be constructed of a soft and/or flexible material. In some embodiments, the inner layer of the housing 5080 can be constructed, for example, of biocompatible nylon, spandex, or the like, or any combination thereof. In some embodiments, the inner layer of the housing includes one or more pores configured to help prevent movement (e.g., slipping or sliding) of the orthosis 5050 with respect to the limb of the patient. In some embodiments, the housing 5080 includes an outer layer having a design scheme configured to coordinate with a design scheme of one or more different orthoses. In some embodiments, the housing 5080 defines an opening through which one or more grip features 5121, 5221 can be disposed (see, e.g., FIG. 64).

As shown in FIG. 52, non-conductive material 5124, 5224 can be included on an inner surface of the housing 5080 with respect to the first cuff 5120 and/or the second cuff 5220 proximate to and/or about the sets of electrode connectors 5122, 5222, respectively. For example, a silicone material can be disposed on (e.g., printed onto) the inner layer of the housing 5080. The material 5122, 5224 can have a shape that substantially corresponds to, or is slightly larger than, an outer perimeter of the first electrode 5150 and second electrode 5250, respectively. The non-conductive material 5124, 5224 is configured to overlap with the edges of its respective electrode 5150, 5250 to prevent current leakage from about the perimeter of the electrode. In some embodiments, the non-conductive material 5124, 5224 is also configured to provide additional stability to its respective cuff 5120, 5220. In some embodiments, however, such non-conductive material is disposed directly onto the first cuff 5120 and/or the second cuff 5220.

Referring to FIG. 51, in some embodiments, the orthosis 5050 includes a removable layer or panel 5500 that is removably coupleable to the orthosis. More specifically, the panel 5500 can be couplable to at least a portion of at least one of the first orthosis member 5100, the second orthosis member 5200 and the bridge connector 5800. The panel 5500 can, for example, provide a hygienic barrier between the frame assembly 5050 and the patient's body during use, thus facilitating sharing or reuse of the orthosis 5050 with an additional and/or subsequent user in a more sanitary manner. The removable panel 5500 can have a perimeter profile or shape that is substantially similar to the perimeter profile or shape of the inner surface of the frame assembly 5055.

The panel 5500 has a first side 5502 (FIG. 51A) and a second side 5504 (FIG. 51B) opposite the first side 5502. The first side 5502 of the panel 5500 is configured to face away from the limb segment (e.g., the thigh) and the second side 5504 is configured to face towards the limb segment, when the panel 5500 is coupled to the frame assembly 5055 and the orthosis 5050 is donned on the limb segment. In some embodiments, the panel 5500 includes a first layer 5506 coupled to a second layer 5508. At a first portion 5501 of the panel 5500, which is configured to be associated with the first orthosis member 5100, the first layer 5506 and second layer 5508 define sleeves 5510, 5512. Each sleeve 5510, 5512 defines an opening or lumen therethrough that is configured to receive opposing portions of the first orthosis member 5100. At a second portion 5503 of the panel 5500, which is configured to be associated with the second orthosis member 5200, the first layer 5506 and second layer 5508 define sleeves 5520, 5522. Each sleeve 5520, 5522 defines an opening or lumen therethrough that is configured to receive opposing portions of the second orthosis member 5200. The panel 5500 can be constructed of a flexible material, which can facilitate disposing opposing portions of the first and second orthosis members 5100, 5200 in the sleeves 5510, 5512 and sleeves 5520, 5522, respectively.

An end portion of each sleeve 5510, 5512 disposed at opposing end portions of the panel 5500 define openings 5511, 5513, respectively, configured to permit the retaining members 5140, 5170, respectively, of the first orthosis member 5100 to extend therethrough. Similarly, sleeves 5520, 5522 define openings 5521, 5523, respectively, at opposing end portions of the panel 5500 configured to permit the retaining members 5240, 5270, respectively, of the second orthosis member 5200 to extend therethrough.

A portion of sleeve 5510 associated with the first side 5502 of the panel 5500 and that is associated with the first orthosis member 5100 can define an opening or aperture, 5514 through which the grip feature 5121 of the first orthosis member 5100 can extend. A portion of sleeve 5512 associated with the first side 5502 of the panel 5500 and that is associated with the first orthosis member 5100 can define an opening or aperture 5516 within which a cradle 5010, described in more detail herein, can be disposed when the panel 5500 is coupled to the frame assembly 5055.

A portion of each sleeve 5520, 5522 associated with the first side 5502 of the panel 5500 and that is associated with the second orthosis member 5200 can define an opening or aperture, 5524, 5526, through which the grip feature 5221 of the second orthosis member 5200 can extend.

Figure 51A:
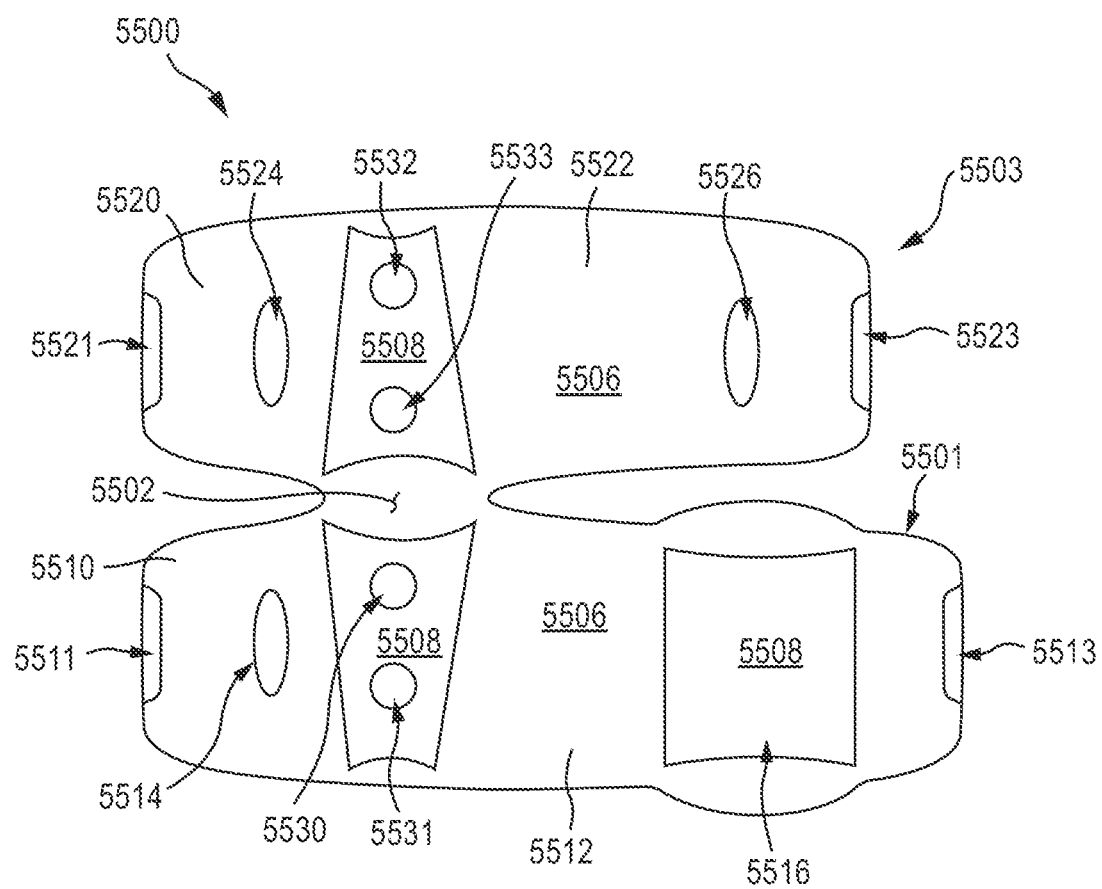
FIGS. 51A-51B are front and rear views of a portion of a frame assembly of the FES orthosis of FIG. 48, in an uncoupled configuration.
Figure 51B:
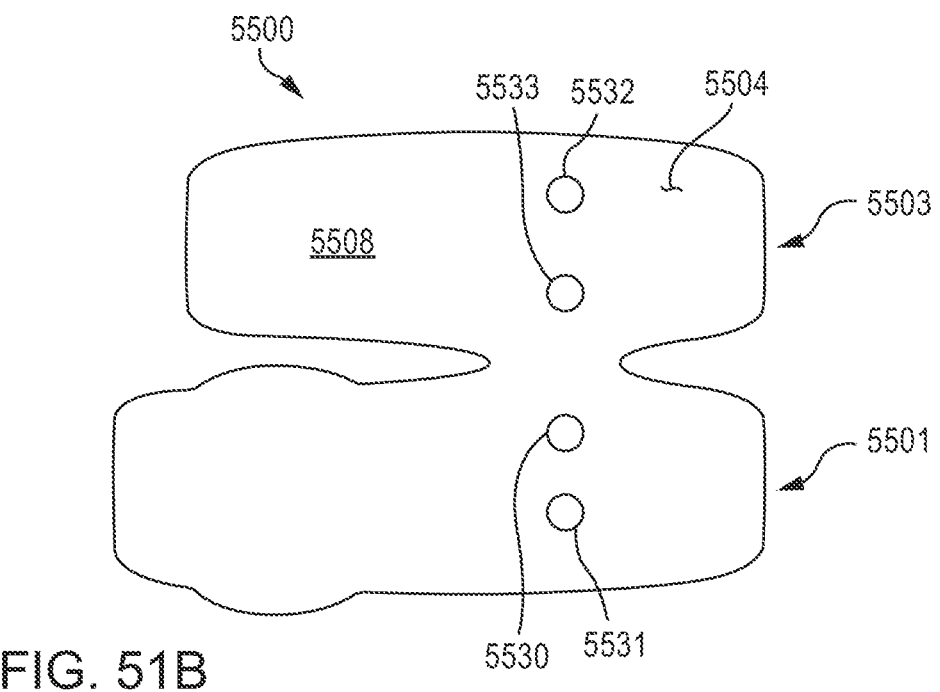

The removable panel 5500 defines openings 5530, 5531 through which at least a portion of at least one of the electrode connectors 5122 or electrode snaps 5152 can be disposed. The panel 5500 also defines openings 5532, 5533 through which at least a portion of at least one of the electrode connectors 5222 or electrode snaps 5252 can be disposed. Although the openings 5530, 5531, 5532, 5533 are shown in FIGS. 51A-51B as being substantially circular in shape, in other embodiments, the openings can be any suitable shape or dimension. In some embodiments, a polypropylene layer (or layer of another suitable material) is circumferentially disposed about one or more of the openings 5530, 5531, 5532, 5533 on the first side of the removable panel 5500, in a similar manner as described herein with respect to panel 1180.

The orthosis member 5100 also includes a cradle 5010 or receiving portion configured to couple the electric stimulator 5400 thereto. The cradle 5010 can be exposed even when the housing 5080 is coupled to the orthosis 5050. The stimulator unit 5400 can be removably coupled to the cradle 5010 in any suitable manner described herein (e.g., with respect to electric stimulator 140, 1400, 540). For example, the electric stimulator 5400 can be removably coupled to the cradle 5010 with a snap-fit connection. The cradle 5010 can include a snap connector configured to receive a mating snap-fit connector (not shown) on the electric stimulator 5400. In another example, the electric stimulator 5400 can be removably coupled to the cradle 5010 with a resistance fit connection between a housing of the stimulator and the cradle. The electric stimulator 5400 can include any of the features and functions as described above for stimulator 140. The electric stimulator 5400 can be used to generate and send a signal to the electrode 5150 and the electrode 5250 to stimulate a portion of the patient's body. The stimulator 5400 can be similar in form and function to any stimulator described herein (e.g., stimulator 140, 1400, 540), and thus is not described in detail herein.

Figure 65:
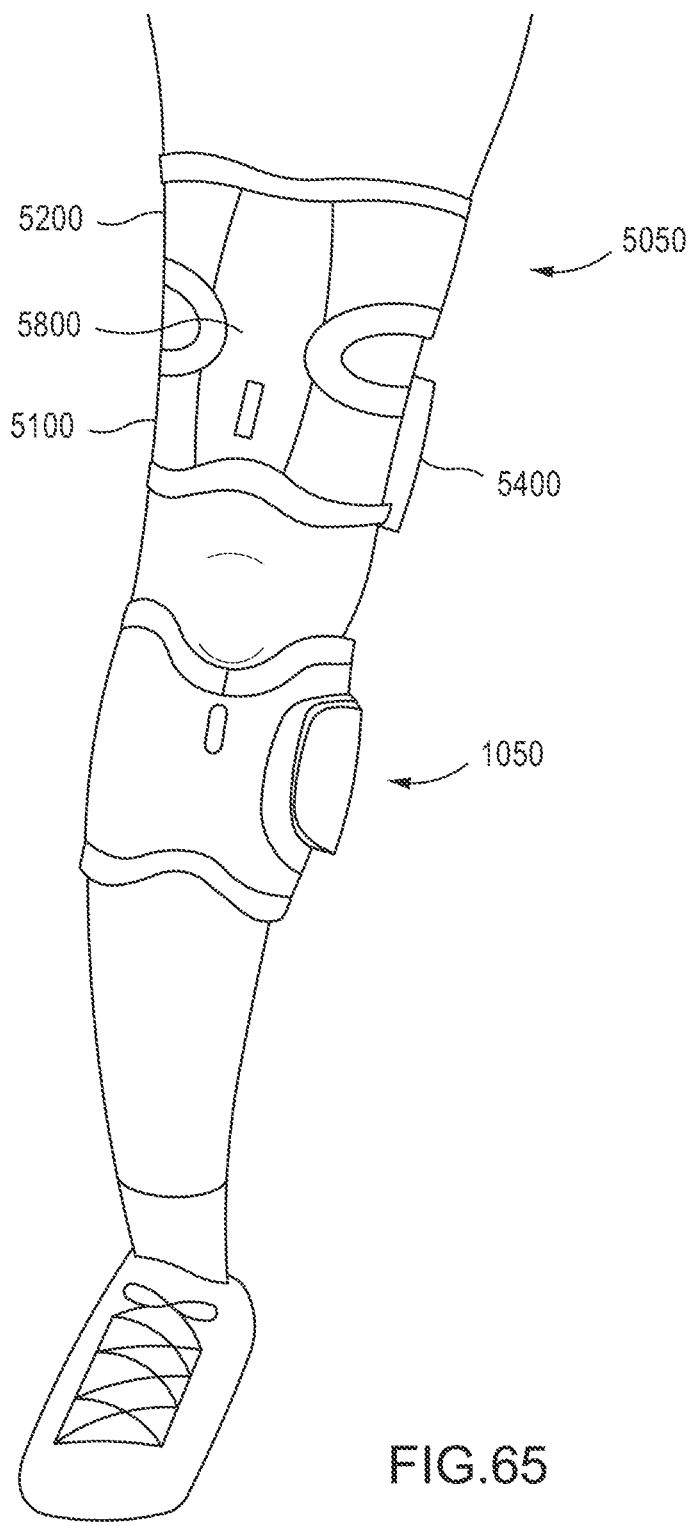
FIG. 65 is a front view of a limb of a patient with the orthoses of FIGS. 4 and 48 disposed thereon.

The orthosis device 5050 can be used in the functional electrical stimulation treatment of various locations on a patient's body, such as for example, a leg, foot, arm or hand. The orthosis device 5050 can be used for the functional electrical stimulation treatment of various muscles or muscle groups on a particular limb. FIG. 65 illustrates the positioning and use of the orthosis device 5050 on a leg of a patient and in particular a thigh or upper leg of the patient. It should be understood, however, that the orthosis device 5050 can be configured for use on other portions of a patient's body. As described herein, although not necessary, the orthosis device 5050 can be used in conjunction with another orthosis device (e.g., orthosis 1050).

In one embodiment, the orthosis device 5050 can be used to treat various muscles on a thigh of a patient. The orthosis device 5050 can be disposed about a first portion of a thigh of a patient such that the electrode 5150 of the first orthosis member 5100 contacts the first portion of the thigh and the second electrode 5250 of the second orthosis member 5200 contacts a second portion of the thigh. The orthosis device 5050 can then be repositioned on the thigh of the patient such that the electrode 5150 of the first orthosis member 5100 contacts the third portion of the thigh and the second electrode 5250 of the second orthosis member 5200 contacts a fourth portion of the thigh.

For example, in one use of the orthosis device 5050, the first orthosis member 5100 is positioned on the thigh of a patient such that the electrode 5150 can stimulate a first portion of a hamstring muscle of the patient and the second orthosis member 5200 is positioned on the thigh of the patient such that the electrode 5250 can stimulate a second portion of the hamstring muscle of the patient. With the buckles 5164, 5264 of the strap assemblies 5130, 5230 decoupled from their respective retaining members 5170, 5270, and with the coupling members 5134, 5234 coupled to their respective retaining members 5140, 5240, a patient can place the orthosis device 5050 on a thigh of the patient with the aide of one more of locators 5102, 5104, 5202, 5051, 5053, e.g., such that locator 502 is disposed a predetermined distance above the back of the patient's knee. The buckle 5164, 5264 of each strap member 5132, 5232 can be coupled to its respective retaining member 5170, 5270, thereby coupling the orthosis 5050 to the thigh. In this position, the first electrode 5150 can be actuated to stimulate a first portion of a hamstring muscle and the second electrode 5250 can be actuated to stimulate a second portion of the hamstring muscle (see, e.g., FIG. 55).

The orthosis device 5050 can be repositioned for use in treating the quadriceps muscle of the patient. To position the orthosis device 5050 to stimulate the quadriceps muscle, the patient can again use one or more locators 5102, 5104, 5202, 5051, 5053. Specifically, with buckles 5164, 5264 the strap assemblies 5130, 5230 decoupled from the retaining members 5170, 5270 and the coupling members 5134, 5234 of the strap assemblies 5130, 5230 coupled to retaining members 5140, 5240 the cuffs 5120, 5220, as described above, the orthosis device 5050 can be placed on the thigh of the patient a predetermined distance from a top of the patient's knee. In this position the first electrode 5150 can be actuated to stimulate a first portion of a quadriceps muscle and the second electrode 5250 can be actuated to stimulate a second portion of the quadriceps muscle (see, e.g., FIG. 54).

The electric stimulator 5400 can be configured to apply stimulation having any suitable intensity and/or according to any suitable stimulation pattern or program, for example such as an intensity and/or stimulation pattern or program described herein (e.g., with respect to orthosis 1050). The electric stimulator 5400 can be in communication with a sensor, such as any sensor described herein (e.g., sensor 130, 530, 1300, 3300). In some embodiments, the electric stimulator 5400 is configured to apply stimulation to one or more of the electrodes 5150, 5250 in response to a signal received from the sensor, such as a signal associated with a gait event, as described herein.

The orthosis device 5050 can also be used when the patient is not walking. For example, the orthosis device 5050 can be used in a training mode without the gait sensor. The training mode can be designed, for example, to facilitate muscle re-education, prevent or retard disuse atrophy of the lower leg and thigh muscles, maintain or improve range of motion of the ankle and knee joints and/or improve blood circulation.

An FES system 3000 according to an embodiment is shown in FIG. 66. As shown in FIG. 66, in some embodiments, the electric stimulator 1400 of orthosis 1050 and/or the electric stimulator 5400 of orthosis 5050 can be in communication with one or more control devices 3500 and 3550. The control device 3500 can be any suitable electronic device that can provide an interface for a user (e.g., the patient and/or a health care professional) to manipulate one or more characteristics and/or parameters associated with the FES. For example, in some embodiments, the control device 3500 can be, for example, a smart phone or the like that can be manipulated to run and/or execute a set of instructions associated with controlling the electric stimulator 1400, 5400, such as via a mobile application stored on the smart phone. In some instances, the control device 3500 can be in wireless communication with the electric stimulator 1400, e.g., via a wireless modality, format, and/or the like associated with WiFi®, Bluetooth®, near field communication (NFC), cellular communication such as, short message service (SMS) or multimedia message service (MMS), and/or the like. In some embodiments, the control device 3500 is any suitable electronic device (e.g., a smart phone) that can receive data (wired and/or wirelessly) from the electric stimulator 5400 and that can be manipulated to run and/or execute a set of instructions associated with analyzing, storing, parsing, or otherwise monitoring the received data. In this manner, the application executed on the smart phone can be used to monitor the patient's usage data (e.g., a log of FES provided via one or more orthoses, including the set(s) of parameters associated with FES provided to the patient, the frequency of use of the system to provide FES, the duration of use of the system to provide FES on a daily, weekly and/or monthly basis), data associated with the patient's gait on a daily, weekly and/or monthly basis, data associated with the patient's number of daily steps taken, data associated with a distance traveled by the patient during gait or other physical activity (e.g., cycling, rowing, paddling, or the like), data associated with the patient's daily range of motion for the impaired limb, data indicative of the frame assembly or assemblies to which the electric stimulator has been coupled to (or attempted to be coupled to) and the duration of such coupling, or the like. In this manner, the control device (e.g., the application on the smart phone) can be configured to detect changes in the patient's gait, usage, or the like, over time. In such embodiments utilizing a control device, the electric stimulator 5400 can optionally be dedicated to the single orthosis 1050 during a predetermined period of time (e.g., instead of being shareable amongst different orthoses, such as orthosis 3050 and/or 5050 described herein).

Similarly, the control device 3550 can be a personal computer (PC), a laptop, a tablet PC, a server device, a workstation, and/or the like that can be manipulated to run and/or execute a set of instructions associated with controlling the electric stimulator 1400, 5400. Although shown in FIG. 66 as being in communication with one or more control devices, in other embodiments, the electric stimulator 1400, 5400 can include any suitable hardware and/or software that can, for example, enable to the electric stimulator 1400, 5400 to function as the control device. For example, in some embodiments, the electric stimulator 1400, 5400 can include a user interface and/or the like that can be manipulated by a user to control at least a portion of the electric stimulator 1400, 5400.

Figure 67:
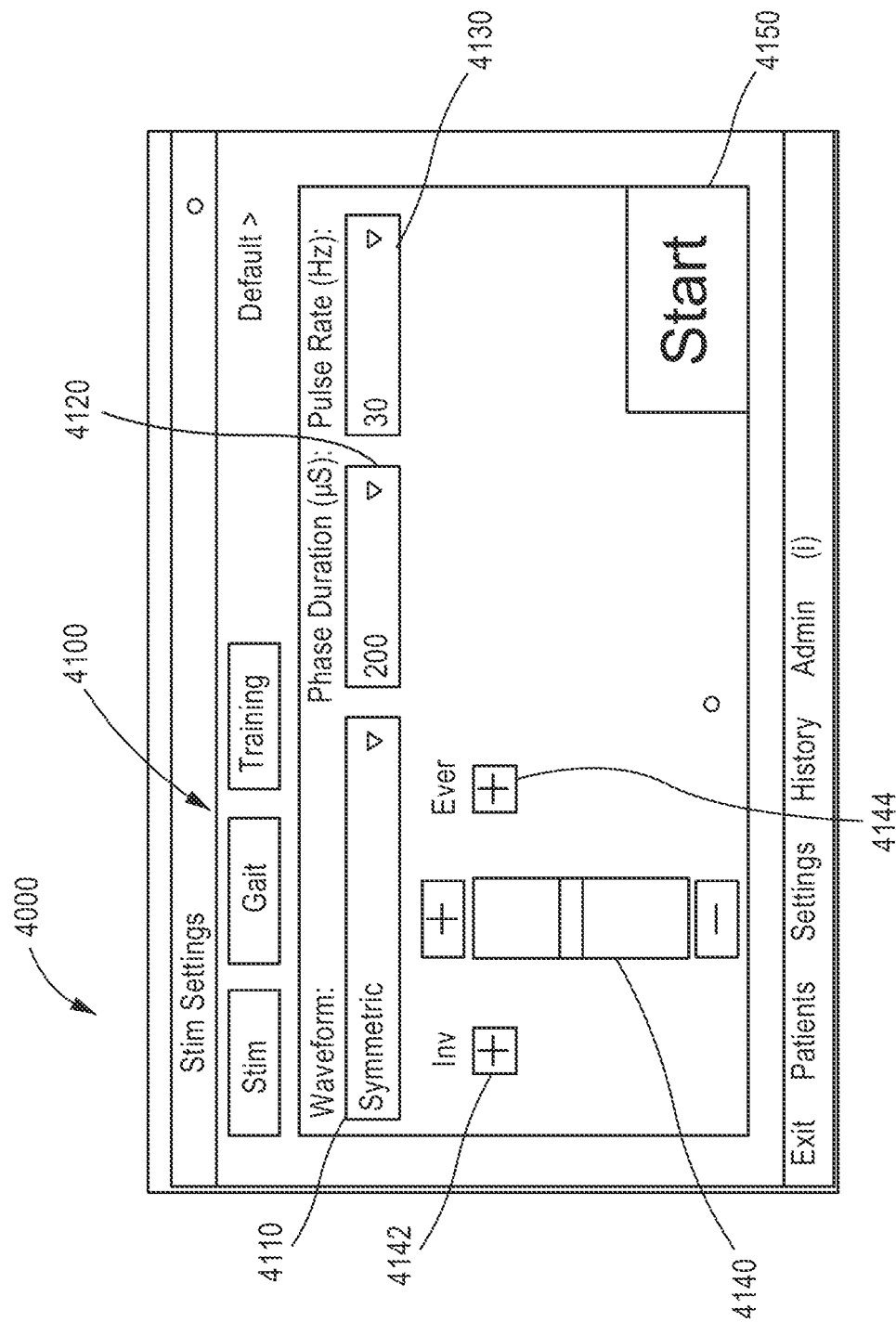
FIGS. 67-68 are schematic illustrations of user interfaces of a control device according to an embodiment.
Figure 68:
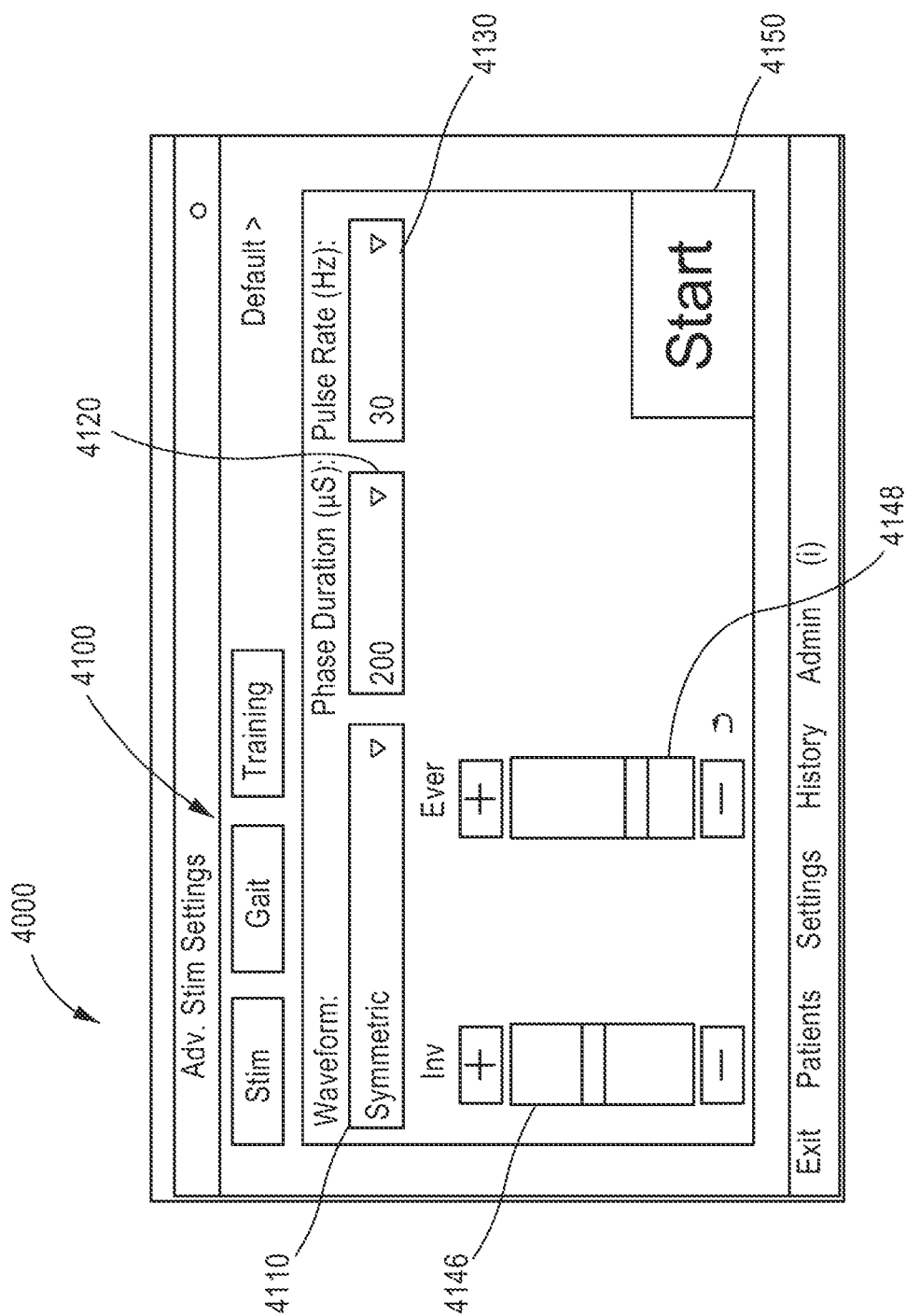

User interfaces 4000 for a control device according to an embodiment is shown in FIGS. 67-68. As shown, the user interface can include a first screen with one or more stimulation parameter input fields (FIG. 67), and a second screen with one or more stimulation parameter input fields (FIG. 68). The user interface 4000 can be configured to permit the user to select an operation mode, such as a stimulation mode, gait mode, or training mode, as indicated by 4100. The user interface 4000 can be configured to permit the user to input or otherwise select values for one or more parameters. As shown in FIG. 67, for example, the user interface 4000 can include an input field 4110 configured to permit the user to select or specify a type of waveform for the stimulation to be output from or otherwise applied by the electric stimulator 1400. The waveform can be selected via any suitable input mechanism, including but not limited to, a selectable drop-down menu as shown in FIG. 67. A symmetric waveform has been selected in FIGS. 67-68, however, a different waveform may be selected or specified in other embodiments.

In another example, the user interface 4000 can include an input field 4120 configured to permit the user to select or specify a phase duration for the stimulation to be output from or otherwise applied by the electric stimulator 1400. The phase duration can be selected or specified via any suitable input mechanism, including but not limited to a selectable drop-down menu as shown in FIG. 67. A phase duration of 200 μs is shown as having been selected in the user interface shown in FIGS. 67-68, however, a different phase duration may be selected or specified in other embodiments.

In still another example, the user interface 4000 can include an input field 4130 configured to permit the user to select or specify a pulse rate for the stimulation to be output from or otherwise applied by the electric stimulator 1400. The pulse rate can be selected or specified via any suitable input mechanism, including, but not limited to, a selectable drop-down menu as shown in FIG. 67. A pulse rate of 30 Hz is shown as having been selected in the user interface 4000 shown in FIGS. 67-68, however, a different pulse rate can be selected or specified in other embodiments. Although the foregoing parameters are shown in FIGS. 67-68 as being selected via a drop-down menu input mechanism, in other embodiments, one or more of the foregoing parameters, or another parameter, can be selected or identified via a different input mechanism (e.g. radio buttons, checkboxes, list boxes, buttons, toggles, or the like) or can be entered into a text field (e.g., via a keyboard, voice command, or the like).

The user interface 4000 can include an input field 4140 configured to permit the user to select or specify an amplitude for the stimulation to be output from or otherwise applied by the electric stimulator 1400, as shown in FIG. 67. As shown, the user can selectively increase or decrease the amplitude (e.g., via plus or minus buttons) within a predetermined range of selectable amplitudes. As shown, the input field 4140 can be used to select or specify the amplitude for the stimulation to be output from the electric stimulator 1400 via two or more channels. In other words, the input field 4140 can be configured to concurrently control the stimulation amplitude for two or more stimulation channels.

The user interface 4000 can include buttons 4142, 4144 configured to permit the user to separately select or specify one or more parameters for the stimulation to be output from or otherwise applied by the electric stimulator 1400 via two or more channels, as shown in FIG. 67. Selection of one or more of buttons 4142, 4144 can, for example, produce a user interface (e.g., a second screen) including one or more additional input fields. For example, as shown in FIG. 68, the user interface 4000 can include an input field 4146 configured to permit the user to select or specify a parameter (e.g., an amplitude) for the stimulation to be output from or otherwise applied by the electric stimulator 1400 via a first channel. As shown, for example, the user can selectively increase or decrease (e.g., via plus or minus buttons) a parameter (e.g., an amplitude) configured to result in inversion of a foot. In another example, as shown in FIG. 68, the user interface 4000 can include an input field 4148 configured to permit the user to select or specify a parameter for the stimulation to be output from or otherwise applied by the electric stimulator 1400 via a second channel. As shown, the user can selectively increase or decrease (e.g., via plus or minus buttons) a parameter (e.g., an amplitude) configured to result in eversion of the foot. Any one or more of the foregoing parameters can be selectively controlled by the user via the user interface 4000 such that the electric stimulator 1400 produces stimulation configured to result in a desired movement or position of a portion of the limb (e.g., the foot).

Although certain parameters (e.g., waveform, phase duration, pulse rate) are shown in FIGS. 67-68 as being concurrently controlled with respect to each stimulation channel by a single input field of the user interface 4000, in other embodiments, each parameter can be independently controlled, with respect to each stimulation channel, via one or more input fields of a user interface. Similarly, although the user interface 4000 is shown and described as including an input field 4140 configured to concurrently control a parameter for two or more stimulation channels, in other embodiments, a user interface can include two or more input fields such that the parameter can be independently controlled for each stimulation channel. For example, such a user interface can be devoid of input field 4140, and the parameter can be controlled by input fields 4146, 4148. The user interface 4000 can optionally include a button 4150 configured to be selectively controlled by a user to initiate and/or stop the output of stimulation (via one, two, three, or more channels, independently or concurrently) via the electric stimulator 1400.

As discussed above, the control device can be used to program or select one or more parameters of the electrical current flowing via the first channel Ch1, the second channel Ch2, or both the first channel Ch1 and the second channel Ch2, based on the effect of such parameter on the flow or distribution of the electrical current through the portion of the neuromuscular system of the limb. Similarly, the control device can be used to program or select one or more parameters associated with an electrical current to be transmitted in a third channel (not shown) instead of or in addition to the first channel Ch1 and/or the second channel Ch2. In some embodiments, the control device can be used to select one or more channels by which the electronic stimulator 1400 sends a stimulation signal. In this manner, during a session with a health care provider to program the stimulator for a unique patient with parameters for the electrical current flow, for example, the health care provider can modify (e.g., increase or decrease) at least one parameter to promote a flow of electrical current through the neuromuscular system of the limb that results in a desired position of a portion of the limb; for example, that results in a desired position (e.g., via dorsiflexion, plantarflexion, inversion, eversion) of the foot or (via extension or flexion) of the hand.

In some instances, at least one of the electric stimulators 1400, 5400 can be configured to communication with any number of electronic devices. For example, in some embodiments, the electric stimulator 1400 can be in electrical communication with the control devices 3500 and 3550, a physically distinct sensor 3300, and, optionally, the orthosis device 5050 and/or a third orthosis 3050. Although the sensor 3300 is shown in FIG. 66 as including a heel sensor (or pressure sensor), in other embodiments, the sensor 3300 includes a motion sensor (e.g., a tilt sensor, an accelerometer, a gyroscope, a speedometer, magnetometer, another suitable sensor described herein, and/or the like).

At least one electric stimulator 1400, 5400 can be configured to communicate with the electronic devices via, for example, unique communication channels. Thus, the control devices 3500 and 3550, the physically distinct sensor 3300, and one or more orthosis 1050, 3050, 5050 can collectively provide FES to a patient that can, for example, enhance the patient's gait or the like. More specifically, in some embodiments, the orthosis 5050 can be configured to be disposed, for example, about the thigh of the patient donning the orthosis 5050 (i.e., the thigh of the impaired leg). The electrodes (not shown) of the orthosis 5050 can be, for example, in electrical communication with one or more portions of the neuromuscular system associated with, for example, the hamstring and/or the quadriceps, as described above. In some embodiments, the orthosis 5050 can be similar in form and/or function to the devices described in U.S. Pat. No. 9,095,417 entitled, "Adjustable Orthosis for Electrical Stimulation of a Limb," filed Feb. 7, 2011, the disclosure of which is incorporated herein by reference in its entirety. In some embodiments, the electric stimulator 1400 can be configured to communicate with the upper leg orthosis 5050 to provide FES to substantially the entirety of an impaired limb of the patient. For example, the electric stimulator 1400 can be coupled to the orthosis 5050, when not coupled to orthosis 1050. Similarly, in some embodiments, the electric stimulator 1400 can be configured to be coupled to an orthosis 3050 disposed about a lower portion of a contralateral leg, as shown in FIG. 66. The orthosis 3050, in some embodiments, is structurally a mirror image of the orthosis 1050, described herein, which can facilitate improved placement of orthosis 3050 on the contralateral leg. Also similarly, the electric stimulator 5400 can be configured for use with an orthosis (e.g., orthosis 1050, 3050), when not in use with orthosis 5050. As described herein, the electric stimulator 1400, 5400 can include a sensor or other mechanism configured to detect and identify to which orthosis 1050, 3050, 5050 the stimulator is coupled, and to determine which stimulation signal(s) to send based on the detected or identified orthosis 1050, 3050, 5050.

While various embodiments have been described above, it should be understood that they have been presented by way of example only, and not limitation. Where schematics and/or embodiments described above indicate certain components arranged in certain orientations or positions, the arrangement of components may be modified. While the embodiments have been particularly shown and described, it will be understood that various changes in form and details may be made. Although various embodiments have been described as having particular features and/or combinations of components, other embodiments are possible having any combination or sub-combination of any features and/or components from any of the embodiments described herein.

For example, the sensor 130 of system 100 can be included in any FES system described herein, which sensor can be configured to send a signal such that the electric stimulator 1400 initiates or sends any stimulation or stimulation signal described herein. Although certain electrodes have been described herein as being a cathodic electrode, in other embodiments, the electrode can be an anodic electrode, or vice versa. Although certain embodiments have been described herein as including an electric stimulator configured to provide monopolar stimulation, in other embodiments, the electric stimulator can provide bipolar stimulation, or vice versa.

Although, in some embodiments, the external stimulator 1400 has been shown and described as being configured to send a first stimulation signal via one channel during a first time period and a second (or third or fourth) stimulation signal via a different channel during the first time period, in other embodiments, the second (or third or fourth) stimulation signal can be sent during a different time period (e.g., an earlier time period, a subsequent time period). In some embodiments, the electric stimulator 1400 is configured to send stimulation signals via two or more channels in alternation or sequential time periods.

Although, in some embodiments, the external stimulator 1400 has been shown and described herein as being configured to send one or more stimulation signals during different time periods, in other embodiments, such stimulation signals can be sent during the same time period.

Although, in some embodiments, a channel is shown or described herein as being a "first channel", in other embodiments, such a channel may be referred to as a second channel, and vice versa.

Although, in some embodiments, a connector (e.g., of the electrode assembly) has been shown and/or described as being a male connector configured to matingly engage with a complementary (e.g., female) connector (e.g., of a frame assembly), in other embodiments, the placement of the male and female connectors can be reversed or switched between the system components.

Although the orthosis 1050 has been shown and described herein as including a frame 1110 disposed between an inner layer 1160 and an outer layer 1170, in other embodiments, an orthosis can be devoid of a semi-rigid frame 1110. For example, such an orthosis can include one or more of an inner layer (e.g., inner layer 1160), outer layer (e.g., outer layer 1170), and optionally one or more additional flexible layers.

Although the FES systems (e.g., system 100, 500, 1000, 3000) have been shown and described herein as being particularly useful for providing FES to a lower limb segment (e.g., the upper and/or lower leg) of the patient during gait, in some embodiments, the system is configured to provide FES to a different body portion, such as a portion of the arm, for example for grasping, and/or during a different physical activity, such as cycling, rowing, paddling, or any other suitable activity. For example, in some embodiments, a user can select one of multiple activity mode options from a menu (e.g., on a user interface) of the system (e.g., gait, cycling, rowing, paddling, or the like). The stimulator 140 includes a set of stimulation parameters stored therein associated with each activity mode. The stimulation parameters for a first activity mode (e.g., gait) are different from the stimulation parameters for a second activity mode (e.g., cycling) different from the first activity mode. In the cycling mode, for example, the FES system uses the same stimulation platform as that used during the gait mode to provide FES to the limb (e.g., leg), however, the FES system provides stimulation based on parameters associated with the cycling mode and in response to signal(s) received from one or more motion and/or position sensors associated with the leg. In the rowing or paddling mode, in another example, the FES system can use the same stimulation platform as that used for restoring arm and/or hand function during typical daily activities to provide FES to the limb (e.g., the arm and/or hand), however the FES system provides stimulation based on parameters associated with the respective rowing or paddling mode and in response to signal(s) received from one or more motion and/or position sensors associated with the arm and/or hand. Such an FES system enables a patient to use the FES systems described herein in lieu of activity-dedicated FES equipment (e.g., a dedicated FES bicycle).

An FES system according to some embodiments can include both an upper limb FES system and a lower limb FES system as described herein, that are configured for use in combination to facilitate FES of the patient's upper limb and lower limb so that the patient can perform one or more predetermined activities. In such an embodiment, the FES system includes an upper limb (e.g., upper and/or lower arm) orthosis and a lower limb (e.g., upper and/or lower limb) orthosis, each of which can be similar to any orthosis described herein. The system can include a stimulator similar in many respects or identical to any stimulator described herein (e.g., stimulator 140, 1400, 540, 5400). In some embodiments, the system includes a stimulator that is configured to be physically and electrically coupled to one of the upper limb orthosis or the lower limb orthosis. The stimulator is also configured to be electrically coupled to (e.g., wirelessly coupled to), but physically separate and distinct from, the other of the upper limb orthosis or the lower limb orthosis. The stimulator can be programmed to transmit electrical stimulation according to a first set of parameters with respect to the upper limb orthosis and electrical stimulation according to a second set of parameters with respect to the lower limb orthosis. The stimulation according to the first set of parameters configured to be output to the upper limb orthosis and the stimulation according to the second set of parameters configured to be output to the lower limb orthosis can be configured to facilitate functional movement of the patient's upper and lower limbs, respectively, so that the patient can functionally utilize both the upper and lower limb during a predetermined or desired activity. In other words, the upper limb orthosis and the lower limb orthosis are configured to work together in providing FES to the patient so that the patient can participate in one or more activities, including, but not limited to, tennis (e.g., in which the arm can be stimulated in a manner to enable grasping of a tennis racquet and/or intentional arm movement to swing the tennis racquet and in which the leg can be stimulated in a manner to facilitate the patient's gait while moving about a tennis court), rowing (e.g., in which the arm can be stimulated to facilitate grasping of an oar and/or arm movement during a rowing stroke and in which the leg can be stimulated to facilitate leg movement including leg press and/or hip extension during the rowing stroke), cycling, hiking, paddleboarding, skiing, or any other activity. In some embodiments, the user can select a mode of operation (e.g., an activity mode) for the stimulator (e.g., via a user interface of the stimulator or a control unit or device, as described herein). The stimulator can selectively output stimulation based at least in part on the mode of operation and one or more signals received from one of more sensors associated with the upper limb orthosis and the lower limb orthosis, respectively. In other embodiments, the system includes a first stimulator associated with the upper limb orthosis and a second stimulator associated with the lower limb orthosis, such that the stimulation according to the first set of parameters is output by the first stimulator and the stimulation according to the second set of parameters is output by the second stimulator. In such a system, the first and second stimulators can optionally be in electrical communication.

In another embodiment, any of the FES systems described herein (e.g., system 100, 500, 1000, 3000) can be configured to detect a fall incurred by the patient or other physical events, for example, based on signal(s) received from one or more motion and/or position sensors. The stimulator can be configured to send a signal to a control device (e.g., a smart phone) in the event such a fall or other event is detected.

Although the FES systems (e.g., system 100, 500, 1000, 3000) shown and described herein include for providing FES to a limb include an orthosis configured to be disposed about and or substantially envelope a limb segment, in other embodiments, one or more components of the systems described herein can be included in an exoskeleton, such as a lower extremity exoskeleton or an upper extremity exoskeleton, configured to substantially an entirety of a limb or a full body exoskeleton. For example, in such an embodiment, a full or partial body exoskeleton can include at least a portion of one or more of an electrode assembly, such as one of the electrode assemblies described herein, a sensor (such as one of the sensors described herein), a frame assembly (such as one of the frame assemblies described herein) and an electric stimulator (such as an electric stimulator described herein. Such a partial body exoskeleton can be configured to substantially contain a patient's leg, lower body from below about the waist to the foot/feet, arm, upper body including the torso and one or both arms. Such a full body exoskeleton can be configured to contain or be disposed about substantially an entirety of the patient's body, optionally except for portions of the patient's head and/or tips of the patient's hand(s) or foot/feet.

The specific configurations of the various components described herein can also be varied. For example, the size and specific shape of the various components can be different from the embodiments shown, while still providing the functions as described herein. Additionally, the relative size of various components of the devices shown and described herein with respect to the size of other components of the devices are not necessarily to scale.

Similarly, where methods and/or events described above indicate certain events and/or procedures occurring in certain order, the ordering of certain events and/or procedures may be modified. While the embodiments have been particularly shown and described, it will be understood that various changes in form and details may be made.

The invention claimed is:

1. An apparatus, comprising:
    an electrode assembly configured to be in electrical communication with a portion of a neuromuscular system of the limb, the electrode assembly including a panel of flexible material and a plurality of surface electrodes coupled to the panel, the plurality of surface electrodes including a set of cathodic electrodes and a set of anodic electrodes;
    a connector assembly including a first connector, a second connector and a third connector, the first connector disposed within a first opening of the panel, the second connector disposed within a second opening of the panel and the third connector disposed within a third opening of the panel, each of the first connector, the second connector and the third connector being configured to be selectively coupled to the electrode assembly; and
    an electric stimulator electrically coupled to the first connector, the second connector and the third connector, the electric stimulator coupled to the electrode assembly, the electric stimulator configured to apply a first electric current via a first channel to the electrode assembly so that the first electric current is transmitted through bodily tissue between a first cathodic electrode from the set of cathodic electrodes and a first anodic electrode from the set of anodic electrodes, the electric stimulator configured to apply a second electric current via a second channel to the electrode assembly so that the second electric current is transmitted through bodily tissue between a second cathodic electrode from the set of cathodic electrodes and at least one of the first anodic electrode or a second anodic electrode from the set of anodic electrodes, the electric stimulator being selectively operable in a first activity mode and a second activity mode different from the first activity mode, the electric stimulator, in the first activity mode, configured to send the first electric current and the second electric current based on a first set of stimulation parameters associated with the first activity mode, the electric stimulator, in the second activity mode, configured to send the first electric current and the second electric current based on a second set of stimulation parameters associated with the second activity mode, the second set of stimulation parameters different from the first set of stimulation parameters.

2. The apparatus of claim 1, wherein:
    the connector assembly includes a fourth connector disposed within a fourth opening of the panel, the fourth connector configured to be selectively coupled to the electrode assembly, the electric stimulator electrically coupled to the fourth connector, the electric stimulator is configured to apply the second electric current so that the second electric current is transmitted through bodily tissue between the second cathodic electrode and the first anodic electrode, and the first anodic electrode is coupled to the third connector and overlying, but electrically uncoupled to, the fourth connector.

3. The apparatus of claim 1, wherein the electric stimulator is configured to apply the second electric current so that the second electric current is transmitted through bodily tissue between the second cathodic electrode and the second anodic electrode.

4. The apparatus of claim 1, wherein the first anodic electrode has a surface area greater than or equal to the combined surface areas of the set of cathodic electrodes.

5. The apparatus of claim 1, wherein at least one of the first electric current and the second electric current is monopolar.

6. The apparatus of claim 5, wherein:
    the connector assembly includes a fourth connector disposed within a fourth opening of the panel, the fourth connector configured to be selectively coupled to the electrode assembly, the electric stimulator electrically coupled to the fourth connector, the first connector is removably coupled to the first cathodic electrode from the set of cathodic electrodes, the second connector is removably coupled to a second cathodic electrode from the set of cathodic electrodes, the third connector is removably coupled to the first anodic electrode from the set of anodic electrodes and the fourth connector is removably coupled to the first anodic electrode.

7. The apparatus of claim 1, wherein:
    the first electric current and the second electric current collectively result in the concurrent dorsiflexion of a foot and movement of the foot from one of an everted position or an inverted position towards a neutral position.

8. A method, comprising:
    sending a first signal via a first channel from an electric stimulator operating in a first activity mode to an electrode assembly to cause a first set of electrodes from the electrode assembly to provide an electric stimulation based on a first set of parameters associated with the first activity mode substantially during a time period to a neuromuscular system of a limb, the first set of electrodes including a first cathodic electrode and a first anodic electrode, the first cathodic electrode and the first anodic electrode being coupled to the electric stimulator via a first connector and a third connector, respectively, of a frame assembly, the first connector and the third connector being disposed within a first opening and a third opening, respectively, of the frame assembly;
    sending a second signal via a second channel from the electric stimulator operating in the first activity mode to the electrode assembly to cause a second set of electrodes from the electrode assembly to provide an electric stimulation based on the first set of stimulation parameters associated with the first activity mode to the neuromuscular system of a limb, the electric stimulation being provided substantially during at least one of the first time period or a second time period subsequent the first time period, the second set of electrodes including a second cathodic electrode and at least one of the first anodic electrode or a second anodic electrode, the second cathodic electrode being coupled to the electric stimulator via a second connector of the frame assembly, the second connector being disposed within a second opening of the frame assembly;

sending the first signal via the first channel from the electric stimulator to the electrode assembly operating in a second activity mode different from the first activity mode to cause the first set of electrodes from the electrode assembly to provide an electric stimulation based on a second set of parameters associated with the second activity mode substantially during a time period to a neuromuscular system of a limb; and sending the second signal via the second channel from the electric stimulator operating in the second activity mode to the electrode assembly to cause the second set of electrodes from the electrode assembly to provide an electric stimulation based on the second set of parameters associated with the second activity mode to the neuromuscular system of a limb.

9. The method of claim 8, wherein the second set of electrodes includes the first anodic electrode, the first anodic electrode is coupled to the third connector of the frame assembly and a fourth connector of the frame assembly, the fourth connector disposed within a fourth opening of the frame assembly, the method further comprising:

returning, from the limb, a portion of the electric stimulation provided by the first set of electrodes via the first anodic electrode; and returning, from the limb, a portion of the electric stimulation provided by the second set of electrodes via the first anodic electrode.

10. The method of claim 8, wherein the first cathodic electrode, the second cathodic electrode, and the first anodic electrode are each fixedly coupled to a flexible panel of the electrode assembly, the electrode assembly being removably coupled to an inner surface of the frame assembly, the frame assembly being removably coupled to a portion of the limb so that the portion of the limb is substantially enveloped by the frame assembly.

11. The method of claim 10, wherein the second anodic electrode is disposed on the flexible panel.

12. The method of claim 10, wherein a non-conductive region of the flexible panel separates the first cathodic electrode, the second cathodic electrode and the first anodic electrode, at least a portion of the non-conductive region is curved or non-linear.

13. The method of claim 8, wherein the electric stimulation provided by the first set of electrodes based on the first set of parameters includes a first amplitude, and the electric stimulation provided by the second set of electrodes based on the first set of parameters includes a second amplitude different from the first amplitude.

14. The method of claim 13, wherein the first amplitude is within the range of about 10 milliamperes (mA) to about 60 mA, and the second amplitude is within the range of about 10 mA to about 40 mA.

15. The method of claim 13, wherein the first amplitude is about 30 mA and the second amplitude is about 25 mA.

16. The method of claim 8, wherein:

the electric stimulation provided from the first set of electrodes and the electric stimulation provided from the second set of electrodes collectively, when the electric stimulator is operating in one of the first activity mode or the second activity mode, results in concurrent dorsiflexion of a foot and movement of the foot from one of an everted position or an inverted position towards a neutral position.

\* \* \* \* \*